(12) United States Patent
Loetscher et al.

(10) Patent No.: US 7,407,655 B2
(45) Date of Patent: Aug. 5, 2008

(54) METHOD OF INHIBITING LEUKOCYTES WITH HUMAN CXC CHEMOKINE RECEPTOR 3 ANTIBODY

(75) Inventors: Marcel Loetscher, Maennedorf (CH); Bernhard Moser, Utzenstorf (CH); Shixin Qin, Lexington, MA (US); Charles R. Mackay, Vancluse (AU)

(73) Assignees: Millennium Pharmaceuticals, Inc., Cambridge, MA (US); Theodor-Kocher Institute, Bern (CH)

( * ) Notice: Subject to any disclaimer, the term of this patent is extended or adjusted under 35 U.S.C. 154(b) by 63 days.

(21) Appl. No.: 10/251,686

(22) Filed: Sep. 20, 2002

(65) Prior Publication Data

US 2003/0158392 A1 Aug. 21, 2003

Related U.S. Application Data

(60) Division of application No. 09/663,702, filed on Sep. 15, 2000, now abandoned, which is a continuation of application No. 08/829,839, filed on Mar. 31, 1997, now Pat. No. 6,184,358, and a continuation-in-part of application No. 09/663,799, filed on Sep. 15, 2000, now abandoned, which is a continuation of application No. 08/709,838, filed on Sep. 10, 1996, now Pat. No. 6,140,064.

(51) Int. Cl.
*A61K 39/395* (2006.01)

(52) U.S. Cl. .............. 424/130.1; 424/133.1; 424/139.1; 424/143.1; 424/141.1

(58) Field of Classification Search ...................... 514/2
See application file for complete search history.

(56) References Cited

U.S. PATENT DOCUMENTS

| | | | |
|---|---|---|---|
| 5,094,941 A | 3/1992 | Hart | |
| 5,532,136 A | 7/1996 | Carlson et al. | |
| 5,543,503 A | 8/1996 | Chuntharapai et al. | |
| 5,545,616 A | 8/1996 | Woodruff | |
| 5,629,283 A | 5/1997 | Nicola et al. | |
| 5,648,219 A | 7/1997 | MacKay et al. | |
| 5,672,694 A | 9/1997 | Campbell et al. | |
| 5,695,945 A | 12/1997 | Tsuji | |
| 6,140,064 A | 10/2000 | Loetscher et al. | |
| 6,171,590 B1 | 1/2001 | Howard et al. | |
| 6,184,358 B1 | 2/2001 | Loetscher et al. | |
| 2001/0006942 A1 | 7/2001 | Howard et al. | |
| 2005/0112119 A1* | 5/2005 | Qin et al. .................. | 424/143.1 |

FOREIGN PATENT DOCUMENTS

| | | |
|---|---|---|
| DE | 4332256 C1 | 3/1995 |
| WO | WO91/02063 | 2/1991 |
| WO | WO94/12635 | 6/1994 |
| WO | WO94/24282 | 10/1994 |
| WO | WO95/08576 | 3/1995 |
| WO | WO97/25340 | 7/1997 |
| WO | WO98/32858 | 7/1998 |
| WO | WO 01/72334 A2 | 10/2001 |

OTHER PUBLICATIONS

Strieter et al., Semin Cancer Biol. 2004, vol. 14(3): 195-200, esp. p. 197: column 2, paragraph 3.*
Miller G., Science 2002, vol. 297(5584): pp. 1116-1118, esp. p. 116: column 2, lines 1-3.*
Murphy, P.M., "The Molecular Biology of Leukocyte Chemoattractant Receptors," *Annu. Rev. Immunol.*, 12:593-633 (1994).
Marchese, A. et al., "Cloning and Chromosomal Mapping of Three Novel Genes, GPR9, GPR10, and GPR14, Encoding Receptors Related to Interleukin 8, Neuropeptide Y, and Somatostatin Receptors," *Genomics*, 29:335-344 (1995).
GenBank Accession No. U32674, submitted by Marchese, A. et al., first released Oct. 2, 1995 according to personnel at the National Center for Biotechnology Information.
Taub, D.D., et al., "Recombinant Human Interferon-inducible Protein 10 is a Chemoattractant for Human Monocytes and T Lymphocytes and Promotes T Cell Adhesion to Endothelial Cells," *J. Exp. Med.*, 177:1809-1814 (1993).
Sarris, A.H., et al., "Human Interferon-inducible Protein 10: Expression and Purification of Recombinant Protein Demonstrate Inhibition of Early Human Hematopoietic Progenitors," *J. Exp. Med.*, 178:1127-1132 (1993).
Luster, A.D. and Leder, P., "IP-10, a -C-X-C- Chemokine, Elicits a Potent Thymus-dependent Antitumor Response In Vivo," *J. Exp. Med.*, 178:1057-1065 (1993).
Angiolillo, A.L., et al., "Human Interferon-inducible Protein 10 is a Potent Inhibitor of Angiogenesis In Vivo," *J. Exp. Med.*, 182:155-162 (1995).
Luster, A.D., et al., "The IP-10 Chemokine Binds to a Specific Cell Surface Heparan Sulfate Site Shared with Platelet Factor 4 and Inhibits Endothelial Cell Proliferation," *J. Exp. Med.*, 182:219-231 (1995).
Taub, D.D., et al., "$\alpha$ and $\beta$ Chemokines Induce NK Cell Migration and Enhance NK-Mediated Cytolysis," *J. Immunol.*, 155:3877-3888 (1995).
Luster, A.D., et al., "$\gamma$-Interferon Transcriptionally Regulates an Early-Response Gene Containing Homology to Platelet Proteins," *Nature*, 315:672-676 (1985).

(Continued)

*Primary Examiner*—Michael Pak
(74) *Attorney, Agent, or Firm*—Hamilton, Brook, Smith and Reynolds, P.C.

(57) ABSTRACT

The present invention relates to proteins or polypeptides, referred to herein as isolated and/or recombinant mammalian (e.g., human) IP-10/Mig receptor proteins designated CXC Chemokine Receptor 3 (CXCR3) and variants thereof, including those characterized by selective binding of one or more chemokines (e.g., IP-10 and/or Mig), and/or the ability to induce a cellular response (e.g., chemotaxis, exocytosis). Antibodies reactive with CXCR3 receptors can be produced using the proteins or variants thereof or host cells comprising same as immunogen.

77 Claims, 17 Drawing Sheets

OTHER PUBLICATIONS

Farber, J.M., "A Macrophage mRNA Selectively Induced by γ-Interferon Encodes a Member of the Platelet Factor 4 Family of Cytokines," *Proc. Natl. Acad. Sci. USA*, 87:5238-5242 (1990).

Farber, J.M., "HuMIG: A New Human Member of the Chemokine Family of Cytokines," *Biochem. Biophys. Res. Commun.*, 192:(1):223-230 (1993).

Liao, F., et al., "Human Mig Chemokine: Biochemical and Functional Characterization," *J. Exp. Med.* 182:1301-1314 (1995).

Förster, R., et al., "A General Method for Screening mAbs Specific for G-protein Coupled Receptors as Exemplified by Using Epitope Tagged BLR1-Transfected 293 Cells and Solid-Phase Cell ELISA," *Biochem. Biophys. Res. Commun.*, 196(3):1496-1503 (1993).

Loetscher, M., et al., "Chemokine Receptor Specific for IP10 and Mig: Strcuture, Function, and Expression in Activated T-Lymphocytes," *J. Exp. Med.*, 184:963-969 (1996).

Miller, M.D. and Krangel, M.S., "Biology and Biochemistry of the Chemokines: A Family of Chemotactic and Inflammatory Cytokines," *Critical Reviews in Immunology*, 12 (1,2):17-46 (1992).

Gayle III, R.B., et al., "Importance of the Amino Terminus of the Interleukin-8 Receptor in Ligand Interactions," *J. Biol. Chem.*, 268(10):7283-7289 (1993).

Sprenger, H., et al., "Structure, Genomic Organization, and Expression of the Human Interleukin-8 Receptor B Gene," *J. Biol. Chem.*, 269(15):11065-11072 (1994).

Oliveira, L., et al., "A Common Motif in G-Protein-Coupled Seven Transmembrane Helix Receptors," *J. Computer-Aided Molecular Design*, 7:649-658 (1993).

Dewald, B., et al., "IP-10, a γ-interferon-inducible Protein Related to Interleukin-8, Lacks Neutrophil Activating Properties," *Immunol. Let.*, 32:81-84 (1992).

Chuntharapai, A. and Kim, K.J., "Generation of Monoclonal Antibodies to Chemokine Receptors," *Methods in Enzymology*, 288:15-27 (1997).

Kaplan, G., et al., "The Expression of γ Interferon-induced Protein (IP-10) in Delayed Immune Responses in Human Skin," *J. Exp. Med.*, 166:1098-1108 (1987).

Gottlieb, A.B., et al., "Detection of a γ Interferon-induced Protein IP-10 in Psoriatic Plaques," *J. Exp. Med.*, 168:941-948 (1988).

George, D.G., et al., "Current Methods in Sequence Comparison and Analysis," *Macromolecular Sequencing and Synthesis Selected Methods and Applications*, (Alan R. Liss, Inc.) pp. 127-149 (1988).

Cunningham, B.C., and Wells, J.A., "High-Resolution Epitope Mapping of hGH-Receptor Interactions by Alanine-Scanning Mutagenesis," *Science*, 244:1081-1085 (1989).

Belperio, John A., et al., "Critical Role for CXCR3 Chemokine Biology in the Pathogenesis of Bronchiolitis Obliterans Syndrome," *The Journal of Immunology*, 169:1037-1049 (2002).

Brown, K.A., "Factors Modifying the Migration of Lymphocytes Across the Blood-Brain Barrier," *International Immunopharmacology*, 1:2043-2062 (2001).

Kawai et al., "Intrathecal Adminstration of Antibodies Against LFA-1 and Against ICAM-1 Suppresses Experimental Allergic Encephalomyelitis in Rats," *Cell. Immunol.*, 171(2):262-268 (1996).

Lu, B., et al., "Structure and Function of the Murine Chemokine Receptor CXCR3," *Eur. J. Immunol.*, 29:3804-3812 (1999).

Soto, H., et al., "The CC Chemokine 6Ckine Binds the CXC Chemokine Receptor CXCR3," *Proc. Natl. Acad. Sci. USA*, 95:8205-8210 (1998).

Holst, B., et al., "Steric Hindrance Mutagenesis Versus Alanine Scan in Mapping of Ligand Binding Sites in the Tachykinin NK$_1$ Receptor," *Mol. Pharmacol.*, 53:166-175 (1998).

Ausubel, F.M., et al., "Hybridization Analysis of DNA Blots," In *Current Protocols In Molecular Biology*, John Wiley & Sons, Inc., (New York, NY), pp. 2.10.1-2.10.16 (1993).

Murphy, P.M. and Tiffany, H.L., "Cloning of Complementary DNA Encoding a Functional Human Interleukin-8 Receptor," *Science*, 253:1280-1283 (1991).

Gerard, C. and Gerard, N.P., "The Pro-Inflammatory Seven-Transmembrane Segment Receptors of the Leukocyte," *Curr. Opin. Immunol.*, 6:140-145 (1994).

Higgins, D.G. and Sharp, P.M., "CLUSTAL: A Package for Performing Multiple Sequence Alignment on a Microcomputer," *Gene*, 73:237-244 (1988).

Qin, S., et al., "The Chemokine Receptors CXCR3 and CCR5 Mark Subsets of T Cells Associated with Certain Inflammatory Reactions," *J. Clin. Invest.*, 101:746-754 (1998).

Mikayama, T., et al., "Molecular Cloning and Functional Expression of a cDNA Encoding Glycosylation-inhibiting Factor," *Proc. Natl. Acad. Sci. USA*, 90:10056-10060 (1993).

Abaza, M.-S. I. and Atassi, M.Z., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin," *J. Protein Chem.*, 11(5): 433-444 (1992).

Li, C.H., et al., "β-Endorphin Omission Analogs: Dissociation of Immunoreactivity from Other Biological Activities," *Proc. Natl. Acad. Sci. USA*, 77(6):3211-3214 (1980).

Goldstein. A., et al., *Principles of Drug Action: The Basis of Pharmacology*, 2$^{nd}$ ed.: (NY: John Wiley & Sons) pp. 98-100 (1974).

Hollenberg, M.D. and Severson, D.L. "Pharmacodynamics: Drug Receptors and Receptors/Mechanisms," In *Principles of Pharmacology*, P.L. Munson, et al.,eds (NY: Chapman and Hall), pp. 7-10 (1995).

Tsicopoulos, A., et al., "Delayed-type Hypersensitivity Reactions to Nominal Protein Antigens and to Environmental Allergens: Similarities and Differences," *Eur. J. Dermatol.*, 9: 261-268 (1999).

Kappel, C.A., et al., "Regulating Gene Expression in Transgenic Animals," *Curr. Opin. Biotechnol.*, 3:548-553 (1992).

Mullins, J.J. and Mullins, L.J., "Transgenesis in Nonmurine Species," *Hypertension*, 22(4): 630-633, (1993).

Houdebine, L.-M., "Production of pharmaceutical proteins from transgenic animals," *J. Biotechnol.*, 34:269-287, (1994).

Wall, R.J., "Transgenic Livestock: Progress and Prospects for the Future", *Theriogenology*, 45:57-68, (1996).

Mullins, L.J. and Mullins, J.J., "Perspectives Series: Molecular Medicine in Genetically Engineered Animals—Transgenesis in the Rat and Larger Mammals," *J. Clin. Invest.*, 97(7):1557-1560, (1996).

Cameron, E.R., "Recent Advances in Transgenic Technology," *Mol. Biotechnol.*, 7:253-265, (1997).

Sigmund, C.D., "Viewpoint: Are Studies in Genetically Altered Mice Out of Control?," *Arterioscler. Thromb. Vasc. Biol.*, 20(6):1425-1429, (2000).

Niemann, H., "Transgenic Farm Animals Get Off the Ground," *Transgenic Res.*, 7:73-75 (1998).

Moreadith, R.W. and Radford, N.B., "Gene Targeting in Embryonic Stem Cells: The New Physiology and Metabolism," *J. Mol. Med.*, 75:208-216 (1997).

Seamark, R.F., "Progress and Emerging Problems in Livestock Transgenesis: A Summary Perspective," *Reprod. Fertil. Dev.*, 6: 653-657 (1994).

Sambrook, J., et al., "Expression of Cloned Genes in *Escherichia coli*" and "Detection and Analysis of Proteins Expressed from Coned Genes," In *Molecular Cloning*, A Laboratory Manual, 2$^{nd}$ ed., (NY: Cold Spring Harbor Laboratory Press), pp. 17.2 and 18.26 (1989).

Mickle, J.E., et al., "Genotype-phenotype Relationships in Cystic Fibrosis," *Med Clin North Am.*, 84(3):597-607 (2000).

Yan, et al., "Two-amino Acid Molecular Switch in an Epithelial Morphogen That Regulates Binding to Two Distinct Receptors," *Science*, 290:523-527 (2000).

Voet, D., et al., *Biochemistry*, John Wiley & Sons, Inc. (New York, NY), pp. 126-128 and 228-234 (1990).

\* cited by examiner

```
CCAACCACAA GCACCAAAGC AGAGGGGCAG GCAGCACACC ACCCAGCAGC CAGAGCACCA      60
GCCCAGCCAT GGTCCTTGAG GTGAGTGACC ACCAAGTGCT AAATGACGCC GAGGTTGCCG     120
CCCTCCTGGA GAACTTCAGC TCTTCCTATG ACTATGGAGA AAACGAGAGT GACTCGTGCT     180
GTACCTCCCC GCCCTGCCCA CAGGACTTCA GCCTGAACTT CGACCGGGCC TTCCTGCCAG     240
CCCTCTACAG CCTCCTCTTT CTGCTGGGGC TGCTGGGCAA CGGCGCGGTG GCAGCCGTGC     300
TGCTGAGCCG GCGGACAGCC CTGAGCAGCA CCGACACCTT CCTGCTCCAC CTAGCTGTAG     360
CAGACACGCT GCTGGTGCTG ACACTGCCGC TCTGGGCAGT GGACGCTGCC GTCCAGTGGG     420
TCTTTGGCTC TGGCCTCTGC AAAGTGGCAG GTGCCCTCTT CAACATCAAC TTCTACGCAG     480
GAGCCCTCCT GCTGGCCTGC ATCAGCTTTG ACCGCTACCT GAACATAGTT CATGCCACCC     540
AGCTCTACCG CCGGGGGCCC CCGGCCCGCG TGACCCTCAC CTGCCTGGCT GTCTGGGGGC     600
TCTGCCTGCT TTTCGCCCTC CCAGACTTCA TCTTCCTGTC GGCCCACCAC GACGAGCGCC     660
TCAACGCCAC CCACTGCCAA TACAACTTCC CACAGGTGGG CCGCACGGCT CTGCGGGTGC     720
TGCAGCTGGT GGCTGGCTTT CTGCTGCCCC TGCTGGTCAT GGCCTACTGC TATGCCCACA     780
TCCTGGCCGT GCTGCTGGTT CCAGGGGCC AGCGGCGCCT GCGGGCCATG CGGCTGGTGG     840
TGGTGGTCGT GGTGGCCTTT GCCCTCTGCT GGACCCCCTA TCACCTGGTG GTGCTGGTGG     900
ACATCCTCAT GGACCTGGGC GCTTTGGCCC GCAACTGTGG CCGAGAAAGC AGGGTAGACG     960
TGGCCAAGTC GGTCACCTCA GGCCTGGGCT ACATGCACTG CTGCCTCAAC CCGCTGCTCT    1020
ATGCCTTTGT AGGGGTCAAG TTCCGGGAGC GGATGTGGAT GCTGCTCTTG CGCCTGGGCT    1080
GCCCCAACCA GAGAGGGCTC CAGAGGCAGC CATCGTCTTC CCGCCGGGAT TCATCCTGGT    1140
CTGAGACCTC AGAGGCCTCC TACTCGGGCT TGTGAGGCCG GAATCCGGGC TCCCCTTTCG    1200
CCCACAGTCT GACTTCCCCG CATTCCAGGC TCCTCCCTCC CTCTGCCGGC TCTGGCTCTC    1260
CCCAATATCC TCGCTCCCGG GACTCACTGG CAGCCCCAGC ACCACCAGGT CTCCCGGGAA    1320
GCCACCCTCC CAGCTCTGAG GACTGCACCA TTGCTGCTCC TTAGCTGCCA AGCCCCATCC    1380
TGCCGCCCGA GGTGGCTGCC TGGAGCCCCA CTGCCCTTCT CATTTGGAAA CTAAAACTTC    1440
ATCTTCCCCA AGTGCGGGGA GTACAAGGCA TGGCGTAGAG GGTGCTGCCC CATGAAGCCA    1500
CAGCCCAGGC CTCCAGCTCA GCAGTGACTG TGGCCATGGT CCCCAAGACC TCTATATTTG    1560
CTCTTTTATT TTTATGTCTA AAATCCTGCT TAAAACTTTT CAATAACAA GATCGTCAGG    1620
ACCTTTTTTT TTTTTTTTTT TTTTTTTTTT TTTTTTTTTT TTTTTTTTT              1670
```

FIG. 1

```
                                                                                                           TM1
MVLEVSDHQVLNDAEVAALLENFSSSYDYGENESDSCCTSPPCPQDFSLNFDRAFLPALYSLLFLLGLLGNGAVAAVLLSRRTALSSTDT    90

TM2                                                   TM3                                 TM4
FLLLILAVADTLLVLTLPLNAV-DAAVQWFGSGLCKVAGALFNINFYAGALLLACISFDRYLNIVIHATQLYRRGPPARVTLTCLAVWGLC   179

TM5                                          TM6
LLFALPDFIFLSAHHDERLNATHCQYNFPQVG-----RTALRVLQLVAGFLLPLLVMAYCYAHILAVLLVSRGQRRL-RAMRLVVVVV    262

TM7
AFALCWTPYHIVVLVDILMDIGALARNCGRESRVDVAKSVTSGLGYMICCLNPLLYAFVGVKFRERMWMLLLR---LGCPNQRGLQRQPS   349

SSRRDSSWSETSEASYSGL    368
```

FIG. 2

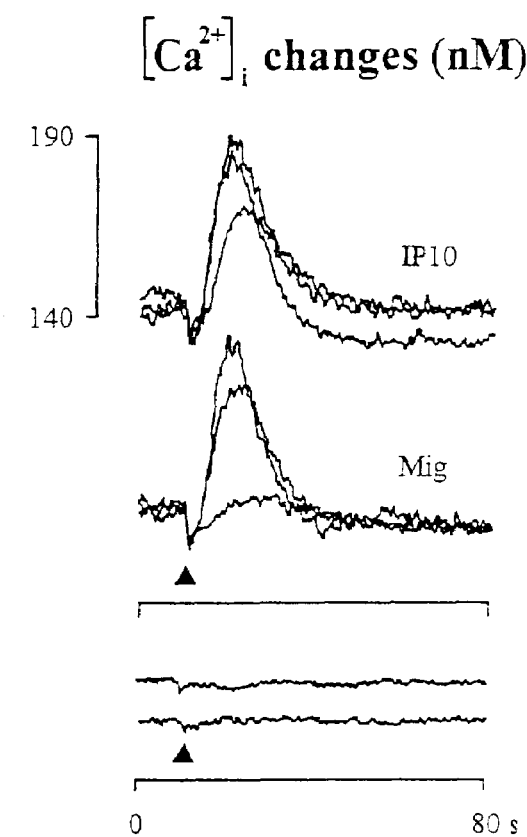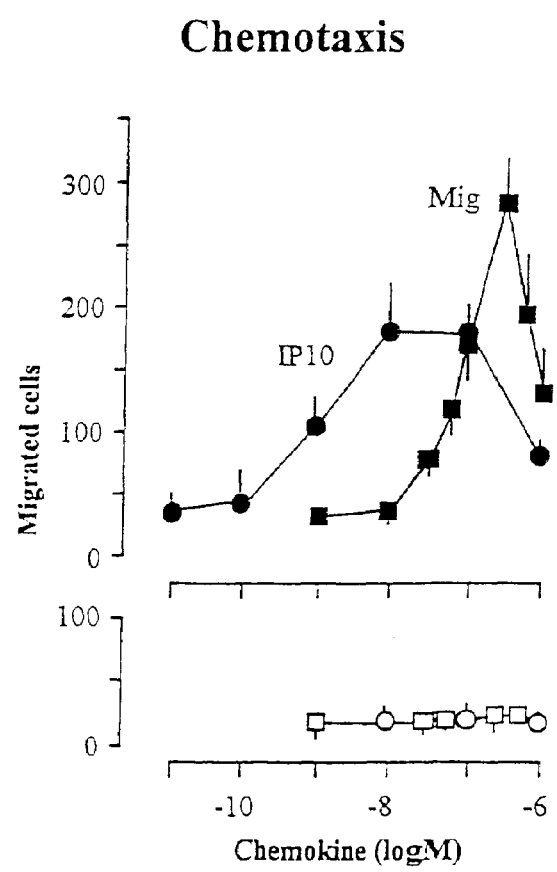
FIG. 4A
FIG. 4B

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 1670 base pairs
      (B) TYPE: nucleic acid
      (C) STRANDEDNESS: double
      (D) TOPOLOGY: unknown (ix) FEATURE:
      (A) NAME/KEY: CDS
      (B) LOCATION: 69..1172

(xi) SEQUENCE DESCRIPTION: SEQ ID NO: 1:

```
CCAACCACAA GCACCAAAGC AGAGGGGCAG GCAGCACACC ACCCAGCAGC CAGAGCACCA          60

GCCCAGCC ATG GTC CTT GAG GTG AGT GAC CAC CAA GTG CTA AAT GAC GCC         110
         Met Val Leu Glu Val Ser Asp His Gln Val Leu Asn Asp Ala
           1               5                  10

GAG GTT GCC GCC CTC CTG GAG AAC TTC AGC TCT TCC TAT GAC TAT GGA          158
Glu Val Ala Ala Leu Leu Glu Asn Phe Ser Ser Ser Tyr Asp Tyr Gly
 15                  20                  25                  30

GAA AAC GAG AGT GAC TCG TGC TGT ACC TCC CCG CCC TGC CCA CAG GAC          206
Glu Asn Glu Ser Asp Ser Cys Cys Thr Ser Pro Pro Cys Pro Gln Asp
                 35                  40                  45

TTC AGC CTG AAC TTC GAC CGG GCC TTC CTG CCA GCC CTC TAC AGC CTC          254
Phe Ser Leu Asn Phe Asp Arg Ala Phe Leu Pro Ala Leu Tyr Ser Leu
             50                  55                  60

CTC TTT CTG CTG GGG CTG CTG GGC AAC GGC GCG GTG GCA GCC GTG CTG          302
Leu Phe Leu Leu Gly Leu Leu Gly Asn Gly Ala Val Ala Ala Val Leu
         65                  70                  75

CTG AGC CGG CGG ACA GCC CTG AGC AGC ACC GAC ACC TTC CTG CTC CAC          350
Leu Ser Arg Arg Thr Ala Leu Ser Ser Thr Asp Thr Phe Leu Leu His
     80                  85                  90

CTA GCT GTA GCA GAC ACG CTG CTG GTG CTG ACA CTG CCG CTC TGG GCA          398
Leu Ala Val Ala Asp Thr Leu Leu Val Leu Thr Leu Pro Leu Trp Ala
 95                 100                 105                 110

GTG GAC GCT GCC GTC CAG TGG GTC TTT GGC TCT GGC CTC TGC AAA GTG          446
Val Asp Ala Ala Val Gln Trp Val Phe Gly Ser Gly Leu Cys Lys Val
                115                 120                 125

GCA GGT GCC CTC TTC AAC ATC AAC TTC TAC GCA GGA GCC CTC CTG CTG          494
Ala Gly Ala Leu Phe Asn Ile Asn Phe Tyr Ala Gly Ala Leu Leu Leu
            130                 135                 140

GCC TGC ATC AGC TTT GAC CGC TAC CTG AAC ATA GTT CAT GCC ACC CAG          542
Ala Cys Ile Ser Phe Asp Arg Tyr Leu Asn Ile Val His Ala Thr Gln
        145                 150                 155

CTC TAC CGC CGG GGG CCC CCG GCC CGC GTG ACC CTC ACC TGC CTG GCT          590
```

```
Leu Tyr Arg Arg Gly Pro Pro Ala Arg Val Thr Leu Thr Cys Leu Ala
    160             165                 170

GTC TGG GGG CTC TGC CTG CTT TTC GCC CTC CCA GAC TTC ATC TTC CTG         638
Val Trp Gly Leu Cys Leu Leu Phe Ala Leu Pro Asp Phe Ile Phe Leu
175                 180                 185                 190

TCG GCC CAC CAC GAC GAG CGC CTC AAC GCC ACC CAC TGC CAA TAC AAC         686
Ser Ala His His Asp Glu Arg Leu Asn Ala Thr His Cys Gln Tyr Asn
                195                 200                 205

TTC CCA CAG GTG GGC CGC ACG GCT CTG CGG GTG CTG CAG CTG GTG GCT         734
Phe Pro Gln Val Gly Arg Thr Ala Leu Arg Val Leu Gln Leu Val Ala
                210                 215                 220

GGC TTT CTG CTG CCC CTG CTG GTC ATG GCC TAC TGC TAT GCC CAC ATC         782
Gly Phe Leu Leu Pro Leu Leu Val Met Ala Tyr Cys Tyr Ala His Ile
            225                 230                 235

CTG GCC GTG CTG CTG GTT TCC AGG GGC CAG CGG CGC CTG CGG GCC ATG         830
Leu Ala Val Leu Leu Val Ser Arg Gly Gln Arg Arg Leu Arg Ala Met
    240                 245                 250

CGG CTG GTG GTG GTG GTC GTG GTG GCC TTT GCC CTC TGC TGG ACC CCC         878
Arg Leu Val Val Val Val Val Val Ala Phe Ala Leu Cys Trp Thr Pro
255                 260                 265                 270

TAT CAC CTG GTG GTG CTG GTG GAC ATC CTC ATG GAC CTG GGC GCT TTG         926
Tyr His Leu Val Val Leu Val Asp Ile Leu Met Asp Leu Gly Ala Leu
                275                 280                 285

GCC CGC AAC TGT GGC CGA GAA AGC AGG GTA GAC GTG GCC AAG TCG GTC         974
Ala Arg Asn Cys Gly Arg Glu Ser Arg Val Asp Val Ala Lys Ser Val
                290                 295                 300

ACC TCA GGC CTG GGC TAC ATG CAC TGC TGC CTC AAC CCG CTG CTC TAT        1022
Thr Ser Gly Leu Gly Tyr Met His Cys Cys Leu Asn Pro Leu Leu Tyr
            305                 310                 315

GCC TTT GTA GGG GTC AAG TTC CGG GAG CGG ATG TGG ATG CTG CTC TTG        1070
Ala Phe Val Gly Val Lys Phe Arg Glu Arg Met Trp Met Leu Leu Leu
    320                 325                 330

CGC CTG GGC TGC CCC AAC CAG AGA GGG CTC CAG AGG CAG CCA TCG TCT        1118
Arg Leu Gly Cys Pro Asn Gln Arg Gly Leu Gln Arg Gln Pro Ser Ser
335                 340                 345                 350

TCC CGC CGG GAT TCA TCC TGG TCT GAG ACC TCA GAG GCC TCC TAC TCG        1166
Ser Arg Arg Asp Ser Ser Trp Ser Glu Thr Ser Glu Ala Ser Tyr Ser
                355                 360                 365

GGC TTG TGAGGCCGGA ATCCGGGCTC CCCTTTCGCC ACAGTCTGA CTTCCCCGCA          1222
Gly Leu

TTCCAGGCTC CTCCCTCCCT CTGCCGGCTC TGGCTCTCCC CAATATCCTC GCTCCCGGGA      1282

CTCACTGGCA GCCCCAGCAC CACCAGGTCT CCCGGGAAGC CACCCTCCCA GCTCTGAGGA      1342

CTGCACCATT GCTGCTCCTT AGCTGCCAAG CCCCATCCTG CCGCCCGAGG TGGCTGCCTG      1402

GAGCCCCACT GCCCTTCTCA TTTGGAAACT AAAACTTCAT CTTCCCCAAG TGCGGGGAGT      1462

ACAAGGCATG GCGTAGAGGG TGCTGCCCCA TGAAGCCACA GCCCAGGCCT CCAGCTCAGC      1522

AGTGACTGTG GCCATGGTCC CCAAGACCTC TATATTTGCT CTTTTATTTT TATGTCTAAA      1582

ATCCTGCTTA AACTTTTCA ATAAACAAGA TCGTCAGGAC CTTTTTTTTT TTTTTTTTT        1642

TTTTTTTTTT TTTTTTTTT TTTTTTTT                                          1670

(2) INFORMATION FOR SEQ ID NO: 2:

(i) SEQUENCE CHARACTERISTICS:
        (A) LENGTH: 368 amino acids
        (B) TYPE: amino acid
        (D) TOPOLOGY: linear (ii) MOLECULE TYPE: protein
```

(xi) SEQUENCE DESCRIPTION: SEQ ID NO: 2:

```
Met Val Leu Glu Val Ser Asp His Gln Val Leu Asn Asp Ala Glu Val
  1               5                  10                  15

Ala Ala Leu Leu Glu Asn Phe Ser Ser Ser Tyr Asp Tyr Gly Glu Asn
                 20                  25                  30

Glu Ser Asp Ser Cys Cys Thr Ser Pro Pro Cys Pro Gln Asp Phe Ser
             35                  40                  45

Leu Asn Phe Asp Arg Ala Phe Leu Pro Ala Leu Tyr Ser Leu Leu Phe
         50                  55                  60

Leu Leu Gly Leu Leu Gly Asn Gly Ala Val Ala Ala Val Leu Leu Ser
 65                  70                  75                  80

Arg Arg Thr Ala Leu Ser Ser Thr Asp Thr Phe Leu Leu His Leu Ala
                 85                  90                  95

Val Ala Asp Thr Leu Leu Val Leu Thr Leu Pro Leu Trp Ala Val Asp
                100                 105                 110

Ala Ala Val Gln Trp Val Phe Gly Ser Gly Leu Cys Lys Val Ala Gly
                115                 120                 125

Ala Leu Phe Asn Ile Asn Phe Tyr Ala Gly Ala Leu Leu Leu Ala Cys
            130                 135                 140

Ile Ser Phe Asp Arg Tyr Leu Asn Ile Val His Ala Thr Gln Leu Tyr
145                 150                 155                 160

Arg Arg Gly Pro Pro Ala Arg Val Thr Leu Thr Cys Leu Ala Val Trp
                165                 170                 175

Gly Leu Cys Leu Leu Phe Ala Leu Pro Asp Phe Ile Phe Leu Ser Ala
            180                 185                 190

His His Asp Glu Arg Leu Asn Ala Thr His Cys Gln Tyr Asn Phe Pro
            195                 200                 205

Gln Val Gly Arg Thr Ala Leu Arg Val Leu Gln Leu Val Ala Gly Phe
        210                 215                 220

Leu Leu Pro Leu Leu Val Met Ala Tyr Cys Tyr Ala His Ile Leu Ala
225                 230                 235                 240

Val Leu Leu Val Ser Arg Gly Gln Arg Arg Leu Arg Ala Met Arg Leu
                245                 250                 255

Val Val Val Val Val Ala Phe Ala Leu Cys Trp Thr Pro Tyr His
                260                 265                 270

Leu Val Val Leu Val Asp Ile Leu Met Asp Leu Gly Ala Leu Ala Arg
            275                 280                 285

Asn Cys Gly Arg Glu Ser Arg Val Asp Val Ala Lys Ser Val Thr Ser
290                 295                 300

Gly Leu Gly Tyr Met His Cys Cys Leu Asn Pro Leu Leu Tyr Ala Phe
305                 310                 315                 320

Val Gly Val Lys Phe Arg Glu Arg Met Trp Met Leu Leu Leu Arg Leu
                325                 330                 335

Gly Cys Pro Asn Gln Arg Gly Leu Gln Arg Gln Pro Ser Ser Ser Arg
            340                 345                 350

Arg Asp Ser Ser Trp Ser Glu Thr Ser Glu Ala Ser Tyr Ser Gly Leu
            355                 360                 365
```

(2) INFORMATION FOR SEQ ID NO: 3:

(i) SEQUENCE CHARACTERISTICS:
(A) LENGTH: 28 base pairs
(B) TYPE: nucleic acid
(C) STRANDEDNESS: single -continued

```
        (D) TOPOLOGY: unknown (ix) FEATURE:
        (A) NAME/KEY: modified_base
        (B) LOCATION: 11
        (D) OTHER INFORMATION: /mod_base= i (ix) FEATURE:
        (A) NAME/KEY: modified_base
        (B) LOCATION: 12
        (D) OTHER INFORMATION: /mod_base= i (ix) FEATURE:
        (A) NAME/KEY: modified_base
        (B) LOCATION: 23
        (D) OTHER INFORMATION: /mod_base= i (ix) FEATURE:
        (A) NAME/KEY: modified_base
        (B) LOCATION: 26
        (D) OTHER INFORMATION: /mod_base= i (xi) SEQUENCE DESCRIPTION: SEQ ID NO: 3:

GGGCTGCAGC NNTKKCMGAC MTNCTNYT                                           28

(2) INFORMATION FOR SEQ ID NO: 4:

(i) SEQUENCE CHARACTERISTICS:
        (A) LENGTH: 27 base pairs
        (B) TYPE: nucleic acid
        (C) STRANDEDNESS: single
        (D) TOPOLOGY: unknown (ix) FEATURE:
        (A) NAME/KEY: modified_base
        (B) LOCATION: 10
        (D) OTHER INFORMATION: /mod_base= i (ix) FEATURE:
        (A) NAME/KEY: modified_base
        (B) LOCATION: 16
        (D) OTHER INFORMATION: /mod_base= i (ix) FEATURE:
        (A) NAME/KEY: modified_base
        (B) LOCATION: 18
        (D) OTHER INFORMATION: /mod_base= i (xi) SEQUENCE DESCRIPTION: SEQ ID NO: 4:

GGGTCTAGAN GGGTTNANRC ARCWRYG                                            27
```

METHOD OF INHIBITING LEUKOCYTES WITH HUMAN CXC CHEMOKINE RECEPTOR 3 ANTIBODY

RELATED APPLICATIONS

This application is a division of U.S. application Ser. No. 09/663,702, filed Sep. 15, 2000 now abandoned, which is a continuation of U.S. application Ser. No. 08/829,839, filed Mar. 31, 1997 (now U.S. Pat. No. 6,184,358 B1); and a continuation-in-part of U.S. application Ser. No. 09/663,799, filed Sep. 15, 2000 now abandoned, which is a continuation of U.S. application Ser. No. 08/709,838, filed Sep. 10, 1996 (now U.S. Pat. No. 6,140,064), the teachings of each of these applications are incorporated herein by reference in their entirety.

BACKGROUND

Chemokines constitute a family of small cytokines that are produced in inflammation and regulate leukocyte recruitment (Baggiolini M. et al., *Adv. Immunol.* 55: 97-179 (1994); Springer, T. A., *Annu. Rev. Physiol.* 57: 827-872 (1995); and Schall, T. J. and K. B. Bacon, *Curr. Opin. Immunol.* 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

Two subfamilies of chemokines, designated as CXC and CC chemokines, are distinguished by the arrangement of the first two of four conserved cysteine residues, which are either separated by one amino acid (as in CXC chemokines IL-8, γIP-10, Mig, PF4, ENA-78, GCP-2, GROα, GROβ, GROγ, NAP-2, NAP-4) or are adjacent residues (as in CC chemokines MIP-1α, MIP-1β, RANTES, MCP-1, MCP-2, MCP-3, I-309). Most CXC chemokines attract neutrophil leukocytes. For example, the CXC chemokines interleukin 8 (IL-8), platelet factor 4 (PF4), and neutrophil-activating peptide 2 (NAP-2) are potent chemoattractants and activators of neutrophils. The CXC chemokines designated Mig (monokine induced by gamma interferon) and IP-10 (γIP-10, interferon-gamma inducible 10 kDa protein) are particularly active in inducing chemotaxis of activated peripheral blood lymphocytes. CC chemokines are generally less selective and can attract a variety of leukocyte cell types, including monocytes, eosinophils, basophils, T lymphocytes and natural killer cells. CC chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

CC and CXC chemokines act through receptors which belong to a superfamily of seven transmembrane spanning G protein-coupled receptors (Murphy, P. M., *Annu. Rev. Immunol.*, 12: 593-633 (1994); Gerard, C. and N. P. Gerard, *Curr. Opin. Immunol.*, 6: 140-145 (1994)). This family of G-protein coupled (serpentine) receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators.

The chemokine receptors can be divided into two groups: CC chemokine receptors 1 through 5 (CCR1-5), which bind CC chemokines, and CXC chemokine receptors 1 through 4 (CXCR1-4), which bind CXC chemokines. In general, the CC chemokine receptors occur on several types of leukocytes, and are important for the migration of monocytes, eosinophils, basophils, and T cells (Qin, S., et al., *Eur. J. Immunol.*, 26:640-647 (1996); Carr, M. W., et al., *Proc. Natl. Acad. Sci. USA*, 91(9):3652-3656 (1994); Taub, D. D., et al., *J. Clin. Invest.*, 95(3):1370-1376 (1995); Neote, K. et al., *Cell*, 72: 415-425 (1993); Gao, J. -L. et al., *J. Exp. Med.*, 177: 1421-1427 (1993); Charo, I. F. et al., *Proc. Natl. Acad. Sci. USA*, 91: 2752-2756 (1994); Myers, S. J., et al., *J. Biol. Chem.*, 270: 5786-5792 (1995); Combadiere, C. et al., *J. Biol. Chem.*, 270 (27): 16491-16494 (1995); and Correction, *J. Biol. Chem.*, 270: 30235 (1995); Ponath, P. D. et al., *J. Exp. Med.*, 183: 2437-2448 (1996); and Daugherty, B. L. et al., *J. Exp. Med.*, 183: 2349-2354 (1996); Power, C. A. et al., 1995, *J. Biol. Chem.*, 270: 19495-19500 (1995); Hoogewerf, A. J. et al., *Biochem. Biophys. Res. Commun.*, 218: 337-343 (1996); Samson, M. et al., *Biochemistry*, 35: 3362-3367 (1996)). In contrast, the two IL-8 receptors, CXCR1 and CXCR2, are largely restricted to neutrophils and are important for the migration of neutrophils (Baggiolini, M., et al., *Adv. Immunol.*, 55:97-179 (1994)). The IL-8 receptors, CXCR1 (IL-8R1, interleukin-8 receptor type 1; Holmes, W. E. et al., *Science*, 253: 1278-1280 (1991)) and CXCR2 (IL-8R2, interleukin-8 receptor type 2; Murphy, P. M. and H. L. Tiffany, *Science*, 253: 1280-1283 (1991)) recognize the NH2-terminal Glu-Leu-Arg (ELR) motif, an essential binding epitope observed in CXC chemokines that induce neutrophil chemotaxis (Clark-Lewis, I. et al., *J. Biol. Chem.*, 266: 23128-23134 (1991); Hébert, C. A. et al., *J. Biol. Chem.*, 266: 18989-18994 (1991); and Clark-Lewis, I. et al., *Proc. Natl. Acad. Sci. USA*, 90: 3574-3577 (1993)).

In contrast to monocytes and granulocytes, lymphocyte responses to chemokines are not well understood. Notably, none of the receptors of known specificity appear to be restricted to lymphocytes and the chemokines that recognize these receptors cannot, therefore, account for events such as the selective recruitment of T lymphocytes that is observed in T cell-mediated inflammatory conditions. Moreover, although a number of proteins with significant sequence similarity and similar tissue and leukocyte subpopulation distribution to known chemokine receptors have been identified and cloned, the ligands for these receptors remain undefined. Thus, these proteins are referred to as orphan receptors. The characterization of the ligand(s) of a receptor, is essential to an understanding of the interaction of chemokines with their target cells, the events stimulated by this interaction, including chemotaxis and cellular activation of leukocytes, and the development of therapies based upon modulation of receptor function.

SUMMARY OF THE INVENTION

The present invention relates to proteins or polypeptides, referred to herein as isolated and/or recombinant mammalian (e.g., a primate such as a human) IP-10/Mig receptor proteins designated CXC Chemokine Receptor 3 (CXCR3) and variants thereof. Recombinant CXCR3 proteins and variants can be produced in host cells as described herein. In one embodiment, a CXCR3 protein or variant thereof is characterized by selective binding (e.g., high affinity binding) of one or more chemokines, such as IP-10 and/or Mig, and/or the ability to induce a (one or more) cellular response(s) (e.g., chemotaxis, exocytosis, release of one or more inflammatory mediators).

Another aspect of the present invention relates to isolated and/or recombinant nucleic acids which encode a mammalian (e.g., a primate such as a human) CXCR3 protein or variant thereof. The invention further relates to recombinant nucleic acid constructs, such as plasmids or retroviral vectors, which contain a nucleic acid which encodes a protein of the present invention or a variant thereof. The nucleic acids and constructs can be used to produce recombinant receptor proteins and host cells comprising a construct. In another embodiment, the nucleic acid encodes an antisense nucleic acid which can hybridize with a second nucleic acid encoding a CXCR3 protein and which, when introduced into cells, can inhibit the expression of receptor.

The invention further relates to antibodies reactive with CXCR3 receptors, which can be produced using the proteins or variants thereof (e.g., a peptide) or cells expressing receptor protein or variant as immunogen, for example. Such antibodies or fragments thereof are useful in therapeutic, diagnostic and research applications, including the purification and study of the receptor proteins, identification of cells expressing surface receptor, and sorting or counting of cells. Thus, the present invention encompasses use of an antibody or fragment thereof described herein (e.g., mAb 1C6 or an antigen-binding fragment thereof) in therapy (including prophylaxis) or diagnosis, and use of such antibodies or fragments for the manufacture of a medicament for use in treatment of diseases or conditions as described herein.

Also encompassed by the present invention are methods of identifying ligands of the receptor, inhibitors (e.g., antagonists) or promoters (e.g., agonists) of receptor function. In one embodiment, suitable host cells which have been engineered to express a receptor protein or variant encoded by a nucleic acid introduced into said cells are used in an assay to identify and assess the efficacy of ligands, inhibitors or promoters of receptor function. Such cells are also useful in assessing the function of the expressed receptor protein or polypeptide.

According to the present invention, ligands, inhibitors and promoters of receptor function can be identified in a suitable assay, and further assessed for therapeutic effect. Inhibitors of receptor function can be used to inhibit (reduce or prevent) receptor activity, and ligands and/or promoters can be used to induce (trigger or enhance) normal receptor function where indicated. Thus, the present invention provides a method of treating inflammatory diseases including autoimmune disease and graft rejection, comprising administering an inhibitor of receptor function to an individual (e.g., a mammal). The present invention further provides a method of stimulating receptor function by administering a ligand or promoter to an individual, providing a new approach to selective stimulation of leukocyte function, which is useful, for example, in the treatment of infectious diseases and cancer.

BRIEF DESCRIPTION OF THE DRAWINGS

FIG. 1 is an illustration of the nucleotide sequence determined from the 1670 bp insert of a cDNA encoding a human IP-10/Mig receptor designated CXCR3, which was isolated from a human CD4+ T cell (KT30) cDNA library (SEQ ID NO:1). An open reading frame (69-1175) encodes a predicted protein of 368 amino acids (SEQ ID NO:2). A putative poly-A signal and poly A site are located at positions 1534-1539 and at 1624-1670, respectively.

FIG. 2 is an illustration of the conceptual translation of the open reading frame of the sequence in FIG. 1, which encodes a human IP-10/Mig receptor (SEQ ID NO:2). Arrowheads indicate potential N-linked glycosylation sites and horizontal lines indicate the location of putative transmembrane domains (TM1-TM7).

FIG. 3A is a graph illustrating the concentration dependent $[Ca^{2+}]_i$ changes in IP-10/MigR-transfected 300-19 cells. IP-10 or Mig were each added at 1, 10, and 100 nM to Fura-2/AM loaded cells (arrowhead), and $[Ca^{2+}]_i$-dependent fluorescence changes were recorded. Non-transfected cells (lower tracings) were stimulated with IP-10 or Mig at 100 nM under identical conditions.

FIG. 3B is a graph illustrating the results of studies assessing receptor desensitization and cross-desensitization, in which IP-10/MigR expressing 300-19 cells were sequentially stimulated with 100 nM IP-10 or Mig, and with IP-10 followed by Mig or vice versa, and fluorescence changes were recorded.

FIG. 3C is a graph illustrating the chemotaxis of IP-10/MigR expressing Jurkat cells stimulated with IP-10 (filled circles) or Mig (filled squares). The lower panel shows the response of non-transfected Jurkat cells when stimulated with increasing amounts of IP-10 (open circles) or Mig (open squares). Mean numbers (+SD) of migrating cells per five high power fields are presented.

FIGS. 4A-4B are graphs illustrating the responses of peripheral blood lymphocytes (PBL) to IP-10 and Mig. Freshly isolated PBL from donor blood buffy coats were used as such (lower tracings and open symbols), or were used after culturing for 10 days in the presence of IL-2 (400 U/ml) (upper tracings and closed symbols). FIG. 4A is a graph illustrating $[Ca^{2+}]_i$ changes induced by IP-10 or Mig. IP-10 or Mig were each added at 1, 10, and 100 nM to Fura-2/AM loaded cultured cells (arrowhead), and $[Ca^{2+}]_i$-dependent fluorescence changes were recorded (upper tracings). Freshly isolated cells (lower tracings) were stimulated with IP-10 or Mig at 100 nM under the same conditions. FIG. 4B is a graph illustrating chemotaxis of PBL in response to increasing concentrations of IP-10 (filled circles) or Mig (filled squares) (mean numbers (±SD) of migrating cells per five high power fields are presented).

DETAILED DESCRIPTION OF THE INVENTION

Figures 3A, 3B, 3C:
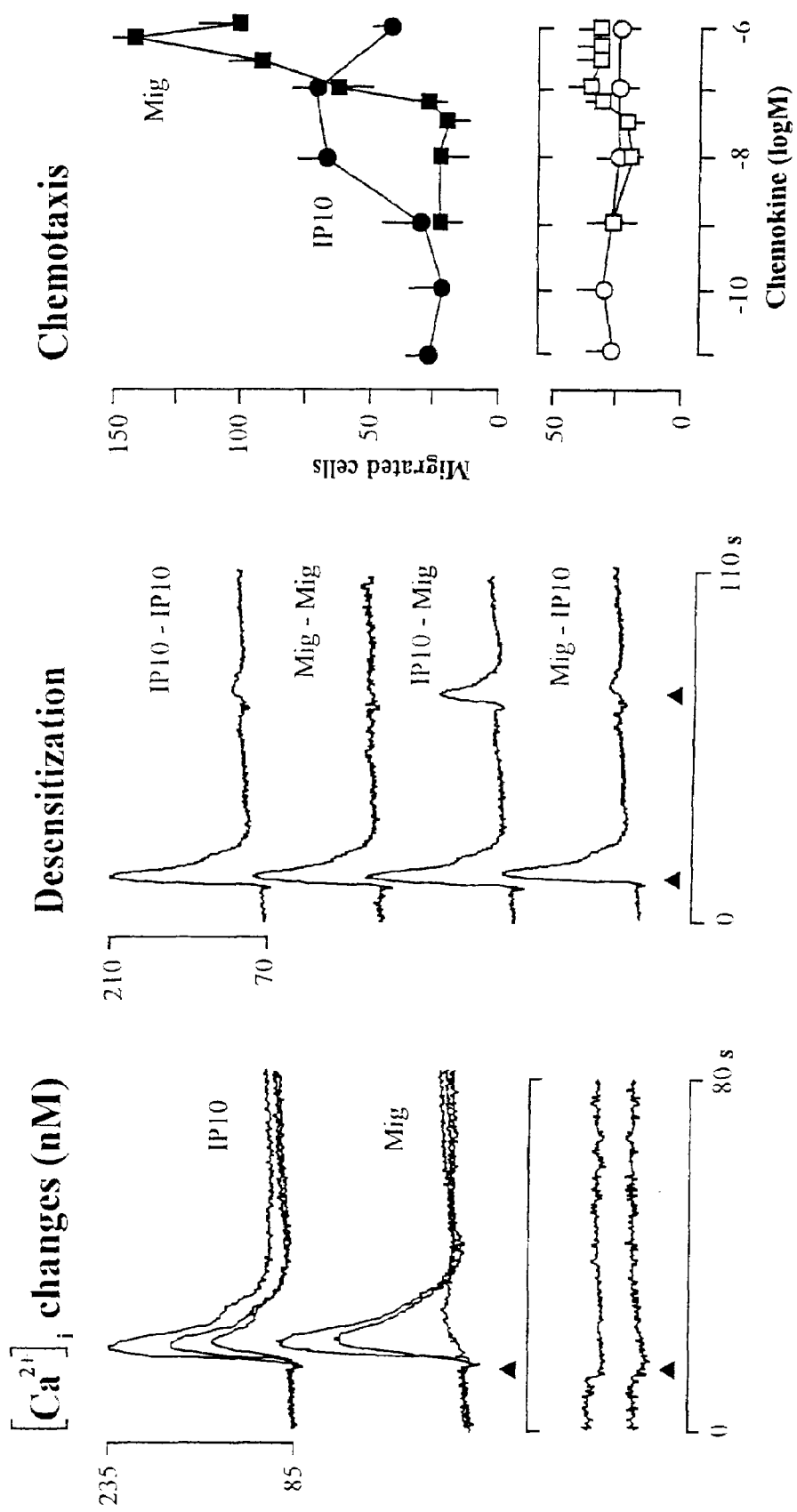
FIGS. 3A-3C are graphs illustrating the responses induced by IP-10 and Mig in stably transfected cells expressing IP-10/MigR.

As described herein, a nucleic acid encoding a novel chemokine receptor that is selective for the CXC chemokines IP-10 and Mig was cloned and characterized. The clone, which was isolated from a human CD4$^+$ T cell library, was not detected in monocyte- or granulocyte-derived cDNA libraries. Sequence analysis of the clone revealed an open reading frame of 1104 base pairs (FIG. 1, SEQ ID NO:1), encoding a predicted protein of 368 amino acids with a predicted molecular mass of 40,659 daltons (FIG. 2, SEQ ID NO:2). The amino acid sequence includes seven putative transmembrane segments which are characteristic of G-protein coupled receptors and are found in other chemoattractant receptors. Consistent with this observation, the receptor mediates Ca$^{2+}$ (calcium ion) mobilization and chemotaxis in response to IP-10 and Mig (Example 2). No significant response to the CXC chemokines IL-8, GROα, NAP-2 (neutrophil-activating protein-2), GCP-2 (granulocyte chemotactic protein-2), ENA78 (epithelial-derived neutrophil-activating peptide 78), PF4 (platelet factor 4), or the CC chemokines MCP-1 (monocyte chemotactic protein-1), MCP-2, MCP-3, MCP-4, MIP-1α (macrophage inflammatory protein-1α), MIP-1β, RANTES (regulated on activation, normal T cell expressed and secreted), I309, eotaxin or lymphotactin was detected under similar conditions.

The restricted expression of human CXCR3 in activated T lymphocytes and the ligand selectivity of the receptor for IP-10 and Mig are noteworthy. The human receptor is highly expressed in IL-2 activated T lymphocytes, but was not detected in resting T lymphocytes, B lymphocytes, monocytes or granulocytes under the conditions used in Example 2. Additional studies of receptor distribution indicate that it is mostly CD3+ cells that express CXCR3, including cells which are CD95+, CD45RO+, and CD45RA$^{low}$, a phenotype consistent with previous activation, although a proportion of CD20+ (B) cells and CD56+ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β and RANTES) are also found in granulocytes, such as neutrophils, eosinophils and basophils, as well as monocytes. These results suggest that the IP-10/Mig receptor designated CXCR3 is involved in the selective recruitment of effector T cells.

The receptor recognizes two unusual CXC chemokines, designated IP-10 and Mig. Although IP-10 and Mig both belong to the CXC subfamily, in contrast to IL-8 and other CXC chemokines which are potent chemoattractants for neutrophils, the primary targets of IP-10 and Mig are lymphocytes, particularly effector cells such as activated or stimulated T lymphocytes and natural killer (NK) cells (Taub, D. D. et al., *J. Exp. Med.*, 177: 18090-1814 (1993); Taub, D. D. et al., *J. Immunol.*, 155: 3877-3888 (1995)). (NK cells are large granular lymphocytes, which lack a specific T cell receptor for antigen recognition, but possess cytolytic activity against cells such as tumor cells and virally infected cells.) Consistently, IP-10 and Mig lack the ELR motif, an essential binding epitope in those CXC chemokines that efficiently induce neutropiil chemotaxis (Clark-Lewis, I. et al., *J. Biol. Chem.*, 266: 23128-23134 (1991); Hébert, C. A. et al., *J. Biol. Chem.*, 266: 18989-18994 (1991); and Clark-Lewis, I. et al., *Proc. Natl. Acad. Sci. USA*, 90: 3574-3577 (1993)). In addition, both recombinant human Mig and recombinant human IP-10 have been reported to induce calcium flux in tumor infiltrating lymphocytes (TIL) (Liao, F. et al., *J. Exp. Med.*, 182: 1301-1314 (1995)). While IP-10 has been reported to induce chemotaxis of monocytes in vitro (Taub, D. D. et al., *J. Exp. Med.*, 177: 1809-1814 (1993), the receptor responsible has not been identified), human Mig appears highly selective, and does not show such an effect (Liao, F. et al., *J. Exp. Med.*, 182: 1301-1314 (1995)). IP-10 expression is induced in a variety of tissues in inflammatory conditions such as psoriasis, fixed DRUG eruptions, cutaneous delayed-type hypersensitivity responses, tuberculoid leprosy, and in experimental glomerulonephritis, and experimental allergic encephalomyelitis. IP-10 also has a potent in vivo antitumor effect that is T cell dependent, is reported to be an inhibitor of angiogenesis in vivo, and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057-1065 (1993); Luster, A. D. et al., *J. Exp. Med.* 182: 219-231 (1995); Angiolillo, A. L. et al., *J. Exp. Med.*, 182: 155-162 (1995); Taub, D. D. et al., *J. Immunol.*, 155: 3877-3888 (1995)). The expression patterns of IP-10 and Mig are also distinct in that expression of each is induced by interferon-gamma (IFNγ), while the expression of IL-8 is down-regulated by IFNγ (Luster, A. D. et al., *Nature*, 315: 672-676 (1985); Farber, J. M., *Proc. Natl. Acad. Sci. USA*, 87: 5238-5242 (1990); Farber, J. M., *Biochem. Biophys. Res. Commun.*, 192 (1): 223-230 (1993), Liao, F. et al., *J. Exp. Med.*, 182: 1301-1314 (1995); Seitz, M. et al., *J. Clin. Invest.*, 87: 463-469 (1991); Caly, A. H. M. and H. Spits, *J. Immunol.*, 147: 3823-3830 (1991)).

Chemokines have been recently recognized as the long-sought mediators for the recruitment of lymphocytes. Several CC chemokines were found to elicit lymphocyte chemotaxis (Loetscher, P. et al., *FASEB J.*, 8: 1055-1060 (1994)), but they are also active on granulocytes and monocytes (Uguccioni, M. et al., *Eur. J. Immunol.*, 25: 64-68 (1995); Baggiolini, M. and C. A. Dahinden, *Immunol. Today*, 15: 127-133 (1994)). The situation is different for IP-10 and Mig, which are selective in their action on lymphocytes, including activated T lymphocytes and NK cells, and which bind CXCR3, a receptor which does not recognize numerous other chemokines and which displays a selective pattern of expression (Example 2, Example 5).

In view of these observations, it is reasonable to conclude that the formation of the characteristic infiltrates in inflammatory lesions, such as delayed-type hypersensitivity lesions, sites of viral infection, and certain tumors is a process mediated by via CXCR3 and regulated by CXCR3 expression. Lymphocytes, particularly T lymphocytes, bearing a CXCR3 receptor as a result of activation can be recruited into inflammatory lesions, sites of infection, or tumors by IP-10 and/or Mig, which can be induced locally by interferon-gamma. Thus, CXCR3 plays a role in the selective recruitment of lymphocytes, particularly effector cells such as activated or stimulated T lymphocytes.

Proteins and Peptides

The present invention relates to isolated and/or recombinant (including, e.g., essentially pure) proteins or polypeptides designated mammalian CXCR3 proteins and variants thereof. In a preferred embodiment, the isolated and/or recombinant proteins of the present invention have at least one property, activity or function characteristic of a mammalian CXCR3 protein (as defined herein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), cellular response function (e.g., stimulation of chemotaxis, exocytosis or inflammatory mediator release by leukocytes), and/or an immunological property as defined herein. For example, some proteins of the present invention can selectively bind to IP-10 and/or Mig, mediate cellular signalling and/or a response thereto in vitro and/or in vivo (e.g., calcium flux, chemotaxis and/or degranulation especially of activated T lymphocytes). For example, as shown herein, a human CXCR3 protein, produced in mammalian cells by expression of a cDNA clone, can selectively bind to CXC chemokines IP-10 and/or Mig, and mediate cell signalling, and a cellular response (e.g., chemotaxis). In one embodiment, proteins of the present invention can bind a CXC chemokine from the same or a different mammalian species (e.g., human IP-10, murine IP-10, human Mig, murine Mig) (human IP-10, Luster, A. D. et al., *Nature*, 315: 672-676 (1985); murine IP-10 (also referred to as CRG-2), Vanguri, P. and J. M. Farber, *J. Biol. Chem.*, 265: 15049 (1990) and Luster, A. D. and P. Leder, *J. Exp. Med.*, 178: 1057-1065 (1993); murine Mig, Farber, J. M., *Proc. Natl. Acad. Sci. USA*, 87: 5238-5242 (1990); human Mig, Farber, J. M., *Biochem. Biophys. Res. Commun.*, 192 (1): 223-230 (1993 and Liao, F. et al., *J. Exp. Med.*, 182: 1301-1314 (1995)).

Proteins or polypeptides referred to herein as "isolated" are proteins or polypeptides purified to a state beyond that in which they exist in mammalian cells, and include proteins or polypeptides obtained by methods described herein, similar methods or other suitable methods, including essentially pure proteins or polypeptides, proteins or polypeptides produced by chemical synthesis (e.g., synthetic peptides), or by combinations of biological and chemical methods, and recombinant proteins or polypeptides which are isolated. The proteins can be obtained in an isolated state of at least about 50% by weight, preferably at least about 75% by weight, or in essentially pure form. Proteins or polypeptides referred to herein as "recombinant" are proteins or polypeptides produced by the expression of recombinant nucleic acids.

As used herein "mammalian CXCR3 protein" refers to naturally occurring or endogenous mammalian CXCR3 proteins and to proteins having an amino acid sequence which is the same as that of a naturally occurring or endogenous corresponding mammalian CXCR3 protein (e.g., recombinant proteins). Accordingly, as defined herein, the term "mammalian CXCR3 protein" includes mature protein, polymorphic or allelic variants, and other isoforms of mammalian CXCR3 (e.g., produced by alternative splicing or other cellular processes), and modified or unmodified forms of the foregoing (e.g., glycosylated, unglycosylated, phosphorylated or unphosphorylated CXCR3 proteins). Naturally occurring or endogenous mammalian CXCR3 proteins include wild type proteins such as mature CXCR3, polymorphic or allelic variants and other isoforms which occur naturally in mammals (e.g., humans, non-human primates). Such proteins can be recovered from a source which naturally produces mammalian CXCR3, for example. These proteins and mammalian CXCR3 proteins having the same amino acid sequence as a naturally occurring or endogenous corresponding mammalian CXCR3, are referred to by the name of the corresponding mammal. For example, where the corresponding mammal is a human, the protein is designated as a human CXCR3 protein (e.g., a recombinant human CXCR3 produced in a suitable host cell).

"Functional variants" of mammalian CXCR3 proteins include functional fragments, functional mutant proteins, and/or functional fusion proteins (e.g., produced via mutagenesis and/or recombinant techniques). Generally, fragments or portions of mammalian CXCR3 proteins encompassed by the present invention include those having a deletion (i.e., one or more deletions) of an amino acid (i.e., one or more amino acids) relative to the mature mammalian CXCR3 protein (such as N-terminal, C-terminal or internal deletions). Fragments or portions in which only contiguous amino acids have been deleted or in which non-contiguous amino acids have been deleted relative to mature mammalian CXCR3 protein are also envisioned.

Generally, mutants or derivatives of mammalian CXCR3 proteins, encompassed by the present invention include natural or artificial variants differing by the addition, deletion and/or substitution of one or more contiguous or non-contiguous amino acid residues, or modified polypeptides in which one or more residues is modified, and mutants comprising one or more modified residues. Preferred mutants are natural or artificial variants of mammalian CXCR3 proteins differing by the addition, deletion and/or substitution of one or more contiguous or non-contiguous amino acid residues. Such mutations can be in a conserved region or nonconserved region (compared to other CXC and/or CC chemokine receptors), extracellular, cytoplasmic, or transmembrane region, for example.

A "functional fragment or portion", "functional mutant" and/or "functional fusion protein" of a mammalian CXCR3 protein refers to an isolated and/or recombinant protein or oligopeptide which has at least one property, activity or function characteristic of a mammalian CXCR3 receptor (as defined herein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), cellular response function (e.g., stimulation of chemotaxis, exocytosis or inflammatory mediator release by leukocytes) and/or an immunological property as defined herein.

As used herein, a protein or polypeptide having "at least one immunological property" of a mammalian CXCR3 protein is one which (a) is bound by at least one antibody of a selected epitopic specificity which binds to a naturally occurring or endogenous mammalian CXCR3 protein or to a protein having the same amino acid seqence as the naturally occurring or endogenous mammalian CXCR3 protein (e.g., human CXCR3), and/or (b) is an immunogen capable of inducing the formation (e.g., when conjugated to a suitable carrier) in a suitable animal of an antibody of a selected epitopic specificity which binds to a naturally occurring or endogenous mammalian CXCR3 or to a protein having the same amino acid seqence as the naturally occurring or endogenous mammalian CXCR3. For example, a suitable fragment can cross-react with an antibody which is raised against and/or reactive with isolated mammalian CXCR3.

Suitable fragments or mutants can be identified by screening. For example, the N-terminal, C-terminal, or internal regions of the protein can be deleted in a step-wise fashion and the resulting protein or polypeptide can be screened using a suitable assay, such as an assay described herein (e.g., chemotaxis, calcium flux). Where the resulting protein displays activity in the assay, the resulting protein ("fragment") is functional. Information regarding the structure and function of mammalian G protein coupled receptors, including CXC chemokine and CC chemokine receptors, provides a basis for dividing mammalian CXCR3 proteins into functional domains (Murphy, P. M., *Annu. Rev. Immunol.*, 12: 593-633 (1994) and Gerard, C. and N. P. Gerard, *Curr. Opin. Immunol.*, 6: 140-145 (1994), and references cited therein).

The term variant also encompasses fusion proteins, comprising a mammalian CXCR3 proteins (e.g., human CXCR3) as a first moiety, linked to a second moiety not occurring in the mammalian CXCR3 as found in nature. Thus, the second moiety can be an amino acid, oligopeptide or polypeptide. The first moiety can be in an N-terminal location, C-terminal location or internal to the fusion protein. In one embodiment, the fusion protein comprises an affinity ligand (e.g., an enzyme, an antigen, epitope tag) as the first moiety, and a second moiety comprising a linker sequence and human CXCR3 or portion thereof.

Examples of mammalian CXCR3 proteins include proteins encoded by a nucleic acid of the present invention, such as a protein having an amino acid sequence as set forth or substantially as set forth in FIG. 2 (SEQ ID NO:2). In a preferred embodiment, a mammalian CXCR3 or variant (e.g., a variant including the extracellular N-terminal segment) has an amino acid sequence which is at least about 50% identical, more preferably at least about 70% identical, and still more preferably at least about 80% identical, to the protein shown in FIG. 2 (SEQ ID NO:2).

It will be appreciated that isolated and/or recombinant mammalian CXCR3 proteins and variants thereof can be modified, for example, by incorporation of or attachment (directly or indirectly (e.g., via a linker)) of a detectable label such as a radioisotope, spin label, antigen (e.g., epitope label such as a FLAG tag) or enzyme label, flourescent or chemiluminesent group and the like, and such modified forms are included within the scope of the invention.

Nucleic Acids, Constructs and Vectors

The present invention relates to isolated and/or recombinant (including, e.g., essentially pure) nucleic acids having sequences which encode a mammalian (e.g., human) CXCR3 protein or variant thereof as described herein. Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids which are isolated. Nucleic acids referred to herein as "recombinant" are nucleic acids which have been produced by recombinant DNA methodology, including those nucleic acids that are generated by procedures which rely upon a method of artificial recombination, such as the polymerase chain reaction (PCR) and/or cloning into a vector using restriction enzymes. "Recombinant" nucleic acids are also those that result from recombination events that occur through the natural mechanisms of cells, but are selected for after the introduction to the cells of nucleic acids designed to allow and make probable a desired recombination event.

In one embodiment, the nucleic acid or portion thereof encodes a protein or polypeptide having at least one function characteristic of a mammalian CXCR3 protein (e.g., a human CXCR3 receptor), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes). The present invention also relates more specifically to isolated and/or recombinant nucleic acids or a portion thereof comprising sequences which encode a mammalian CXCR3 receptor or a portion thereof. The present invention relates even more specifically to isolated and/or recombinant nucleic acids comprising sequences which encode a human CXCR3 protein.

The invention further relates to isolated and/or recombinant nucleic acids, including double or single stranded DNA or RNA, that are characterized by (1) their ability to hybridize to: (a) a nucleic acid having the sequence SEQ ID NO:1, (b) a nucleic acid having a sequence which is complementary to SEQ ID NO:1, or (c) a portion of the foregoing comprising the open reading frame of SEQ ID NO:1 (a portion of the strand illustrated in FIG. 1 or the corresponding portion of the complementary strand); and/or (2) by their ability to encode a polypeptide having the amino acid sequence SEQ ID NO:2 or a functional equivalent thereof (i.e., a polypeptide having ligand binding activity for one or more natural or physiological ligand(s) of the receptor and/or stimulatory function responsive to ligand binding, such that it can induce a cellular response (e.g., induction (including triggering or stimulation) of chemotaxis, exocytosis or inflammatory mediator release by leukocytes); and/or (3) by both characteristics.

In one embodiment, the percent amino acid sequence identity between SEQ ID NO:2 and functional equivalents thereof is at least about 60% ($\geq$60%). In a preferred embodiment, functional equivalents of SEQ ID NO:2 share at least about 700 sequence identity with SEQ ID NOS:2. More preferably, the percent amino acid sequence identity between SEQ ID NO:2 and functional equivalents thereof is at least about 80%, and still more preferably, at least about 90%.

Isolated and/or recombinant nucleic acids meeting these criteria comprise nucleic acids having sequences identical to sequences of naturally occurring mammalian CXCR3 receptors and portions thereof, or variants of the naturally occurring sequences. Such variants include mutants differing by the addition, deletion or substitution of one or more residues, modified nucleic acids in which one or more residues is modified (e.g., DNA or RNA analogs), and mutants comprising one or more modified residues. In one embodiment, the nucleic acid shares at least about 50% nucleotide sequence similarity, more preferably at least about 75% nucleotide sequence similarity, and still more preferably at least about 90% nucleotide sequence similarity, with one strand of the sequence illustrated in SEQ ID NO:1 or to the coding region thereof. Preferred nucleic acids have lengths of at least about 40 nucleotides, more preferably at least about 50, and still more preferably at least about 75 nucleotides.

Such nucleic acids can be detected and isolated by hybridization under high stringency conditions or moderate stringency conditions, for example. "High stringency conditions" and "moderate stringency conditions" for nucleic acid hybridizations are explained on pages 2-10.1-2.10.16 (see particularly 2.10.8-11) and pages 6.3.1-6 in *Current Protocols in Molecular Biology* (Ausubel, F. M et al., eds., Vol. 1, Suppl. 26, 1991), the teachings of which are incorporated herein by reference. Factors such as probe length, base composition, percent mismatch between the hybridizing sequences, temperature and ionic strength influence the stability of nucleic acid hybrids. This, high or moderate stringency conditions can be determined empirically to achieve the desired selectivity.

Isolated and/or recombinant nucleic acids that are characterized by their ability to hybridize to a nucleic acid having the sequence SEQ ID NO:1 or the complement thereof (e.g., under high or moderate stringency conditions) may further encode a protein or polypeptide having at least one function characteristic of a mammalian CXCR3 protein (e.g., a human CXCR3 protein), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or stimulation of a cellular response (e.g., stimulation of chemotaxis, exocytosis or inflammatory mediator release by leukocytes).

The human CXCR3 nucleic acid described herein, or sufficient portions thereof, whether isolated, recombinant and/or synthetic, including fragments produced by PCR, can be used as probes or primers to detect and/or recover nucleic acids (e.g., genomic DNA, allelic variants, cDNA) encoding CXCR3 receptors (homologs) or other related receptor genes (e.g., novel CXC chemokine receptor genes) from other mammalian species including, but not limited to primates (e.g., a primate other than a human, such as a monkey (e.g., cynomolgus monkey)), bovine, ovine, equine, canine, feline and rodent (e.g., guinea pig, murine species such as rat, mouse). This can be achieved using the procedures described herein or other suitable methods, including hybridization, PCR or other suitable techniques. Mammalian nucleic acids can be used to prepare constricts (e.g., vectors), receptor or fragments thereof, and host strains useful in the production and methods of use of receptor.

In one embodiment, a nucleic acid encoding a mammalian CXCR3 protein (or variant) is producible by methods such as PCR amplification. For example, appropriate primers (e.g., a pair of primers or nested primers) can be designed which comprise a sequence which is complementary or substantially complementary to a portion of the human CXCR3 cDNA described herein. For instance, primers complementary to the 5'- or 3'-ends of the coding sequence and/or flanking the coding sequence can be designed. Such primers can be used in a polymerase chain reaction with a suitable template nucleic acid to obtain nucleic acid encoding a mammalian CXCR3, for example. Suitable templates include e.g., constructs described herein (such as pcDNA3-Clone8), a cDNA or genomic library or another suitable source of mammalian (e.g., a human, primate) cDNA or genomic DNA. Primers can contain portions complementary to flanking sequences of a construct selected as template as appropriate.

The binding function of a protein or polypeptide (e.g., encoded by hybridizing nucleic acid) can be detected in binding or binding inhibition assays, using membrane fractions containing receptor or cells expressing receptor, for example (see e.g., Van Riper et al., *J. Exp. Med.*, 177: 851-856 (1993); Sledziewski et al., U.S. Pat. No. 5,284,746 (Feb. 8, 1994)). Thus, the ability of the encoded protein or polypeptide to bind a ligand, such as IP-10 or Mig, an inhibitor and/or promoter, can be assessed. The antigenic properties of proteins or polypeptides encoded by nucleic acids of the present invention can be determined by immunological methods employing antibodies that bind to a mammalian CXCR3, such as immunoblotting, immunoprecipitation and immunoassay (e.g., radioimmunoassay, ELISA).

The signalling function of a protein or polypeptide (e.g., encoded by hybridizing nucleic acid) can be detected by enzymatic assays for G protein activity responsive to receptor binding (e.g., exchange of GTP for GDP on the G protein $\alpha$ subunit, using membrane fractions). G protein coupling can be further assessed, for example, using assays in which stimulation by G protein is blocked by treatment or pre-treatment of cells or a suitable cellular fraction (e.g., membranes) with specific inhibitors of G proteins, such as *Bordetella pertussis* toxin (Bischoff, S. C. et al., *Eur. J. Immunol.*, 23: 761-767 (1993); Sozzani, S. et al., *J. Immunol.*, 147: 2215-2221 (1991)).

The stimulatory function of a protein or polypeptide (e.g., encoded by hybridizing nucleic acid) can be detected by standard assays for chemotaxis or mediator release, using cells expressing the protein or polypeptide (e.g., assays which monitor chemotaxis, exocytosis (e.g., degranulation of enzymes, such as esterases (e.g., serine esterases), perforin, granzymes) or mediator release (e.g., histamine, leukotriene) in response to a ligand (e.g., a chemokine such as IP-10 or Mig) or a promoter (see e.g., Taub, D. D. et al., *J. Immunol.*, 155: 3877-3888 (1995); Baggliolini, M. and C. A. Dahinden, *Immunology Today*, 15: 127-133 (1994) and references cited therein). Functions characteristic of a mammalian CXCR3 receptor may also be assessed by other suitable methods.

These methods, alone or in combination with other suitable methods can also be used in procedures for the identification and/or isolation of nucleic acids which encode a polypeptide having the amino acid sequence SEQ ID NO:2 or functional equivalents thereof, and having an activity detected by the assay. Portions of isolated nucleic acids which encode polypeptide portions of SEQ ID NO:2 having a certain function can be also identified and isolated in this manner.

Nucleic acids of the present invention can be used in the production of proteins or polypeptides. For example, a nucleic acid containing all or part of the coding sequence for a mammalian CXCR3 receptor, or DNA which hybridizes to the sequence SEQ ID NO:1, or the complement thereof, can be incorporated into a construct for further manipulation of sequences or for production of the encoded polypeptide in suitable host cells. Nucleic acids of the present invention can also be modified, for example, by incorporation of or attachment (directly or indirectly) of a detectable label such as a radioisotope, spin label, antigen or enzyme label, flourescent or chemiluminesent group and the like, and such modified forms are included within the scope of the invention.

Antisense Constructs

In another embodiment, the nucleic acid is an antisense nucleic acid, which is complementary, in whole or in part, to a target molecule comprising a sense strand, and can hybridize with the target molecule. The target can be DNA, or its RNA counterpart (i.e., wherein T residues of the DNA are U residues in the RNA counterpart). When introduced into a cell using suitable methods, antisense nucleic acid can inhibit the expression of the gene encoded by the sense strand. Antisense nucleic acids can be produced by standard techniques.

In one embodiment, the antisense nucleic acid is wholly or partially complementary to and can hybridize with a target nucleic acid, wherein the target nucleic acid can hybridize to a nucleic acid having the sequence of the complement of SEQ ID NO:1. For example, antisense nucleic acid can be complementary to a target nucleic acid having the sequence of SEQ ID NO:1 or a portion thereof sufficient to allow hybridization. In another embodiment, the antisense nucleic acid is wholly or partially complementary to and can hybridize with a target nucleic acid which encodes a mammalian CXCR3 receptor (e.g., human IP-10/Mig receptor CXCR3).

Antisense nucleic acids are useful for a variety of purposes, including research and therapeutic applications. For example, a construct comprising an antisense nucleic acid can be introduced into a suitable cell to inhibit receptor expression. Such a cell provides a valuable control cell, for instance in assessing the specificity of receptor-ligand interaction with the parent cell or other related cell types. In another aspect, such a construct can be introduced into some or all of the cells of a mammal. The antisense nucleic acid inhibits receptor expression, and inflammatory processes mediated by CXCR3 receptors in the cells containing the construct can be inhibited. Thus, an inflammatory disease or condition can be treated using an antisense nucleic acid of the present invention. Suitable laboratory animals comprising an antisense construct can also provide useful models for deficiencies of leukocyte function, and of activated T lymphocyte deficiency in particular, and can provide further information regarding CXCR3 receptor function. Such animals can provide valuable models of infectious disease or cancer, useful for elucidating the role of leukocytes, such as T lymphocytes and NK cells, in host defenses.

Method of Producing Recombinant Proteins

Another aspect of the invention relates to a method of producing a mammalian CXCR3 protein or variant (e.g., portion) thereof. Recombinant protein can be obtained, for example, by the expression of a recombinant nucleic acid (e.g., DNA) molecule encoding a mammalian CXCR3 or variant thereof in a suitable host cell, for example.

Constructs (e.g., expression vectors) suitable for the expression of a mammalian CXCR3 protein or variant thereof are also provided. The constructs can be introduced into a suitable host cell, and cells which express a recombinant mammalian CXCR3 protein or variant thereof can be produced and maintained in culture. Such cells are useful for a variety of purposes, including use in the production of protein for characterization, isolation and/or purification, (e.g., affinity purification), use as immunogen, and in binding assays or other functional assays (e.g., to screen for ligands, inhibitors and/or promoters of receptor function), for instance. Suitable host cells can be procaryotic, including bacterial cells such as *E. coli, B. subtilis* and or other suitable bacteria, or eucaryotic, such as fungal or yeast cells (e.g., *Pichia pastoris, Aspergilius* species, *Saccharomzyces cerevisiae, Schizosaccharomyces pombe, Neurospora crassa*), or other lower eucaryotic cells, and cells of higher eucaryotes such as those from insects (e.g., Sf9 insect cells (WO 94/26087, O'Connor, published Nov. 24, 1994)) or mammals (e.g., Chinese hamster ovary cells (CHO), COS cells, HuT 78 cells, 293 cells). (See, e.g., Ausubel, F. M. et al., eds. *Current Protocols in Molecular Biology*, Greene Publishing Associates and John Wiley & Sons Inc., (1993)).

Host cells which produce a recombinant mammalian CXCR3 protein or variant thereof can be produced as follows. For example, a nucleic acid encoding all or part of the coding sequence for the desired protein can be inserted into a nucleic acid vector, e.g., a DNA vector, such as a plasmid, virus or other suitable replicon for expression. A variety of vectors are available, including vectors which are maintained in single copy or multiple copy, or which become integrated into the host cell chromosome.

Transcriptional and/or translational signals of a mammalian CXCR3 gene can be used to direct expression. Suitable expression vectors for the expression of a nucleic acid encoding all or part of the coding sequence of the desired protein are also available. Suitable expression vectors can contain a number of components, including, but not limited to one or more of the following: an origin of replication; a selectable marker gene; one or more expression control elements, such as a transcriptional control element (e.g., a promoter, an enhancer, terminator), and/or one or more translation signals; a signal sequence or leader sequence for membrane targeting in a selected host cell (e.g., of mammalian origin or from a heterologous mammalian or non-mammalian species). In a construct, a signal sequence can be provided by the vector, the mammalian CXCR3 coding sequence, or other source. Sequences present at a site of integration can also provide these elements.

A promoter can be provided for expression in a suitable host cell. Promoters can be constitutive or inducible. For example, a promoter can be operably linked to a nucleic acid encoding the mammalian CXCR3 protein or variant thereof, such that it directs expression of the encoded polypeptide. A variety of suitable promoters for procaryotic (e.g., lac, tac, T3, T7 promoters for *E. coli*) and eucaryotic (e.g., yeast alcohol dehydrogenase (ADH1), SV40, CMV) hosts are available.

In addition, the expression vectors typically comprise a selectable marker for selection of host cells carrying the vector, and, in the case of replicable expression vector, an origin or replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated. The present invention also relates to cells carrying these expression vectors.

For example, a nucleic acid encoding a mammalian CXCR3 protein or variant thereof, or a construct comprising such nucleic acid, can be introduced into a suitable host cell by a method appropriate to the host cell selected (e.g., transformation, transfection, electroporation, infection) such that the nucleic acid is operably linked to one or more expression control elements (e.g., in a vector, in a construct created by processes in the cell, integrated into the host cell genome). Host cells can be maintained under conditions suitable for expression (e.g., in the presence of inducer, suitable media supplemented with appropriate salts, growth factors, antibiotic, nutritional supplements, etc.), whereby the encoded polypeptide is produced. If desired, the encoded protein (e.g., human CXCR3) can be isolated (e.g., from the host cells, medium, milk). It will be appreciated that the method encompasses expression in a host cell of a transgenic animal (see e.g., WO 92/03918, GenPharm International, published Mar. 19, 1992).

Fusion proteins can also be produced in this manner. For example, some embodiments can be produced by the insertion of a mammalian CXCR3 protein cDNA or portion thereof into a suitable expression vector, such as Bluescript®II SK+/−(Stratagene), pGEX-4T-2 (Pharmacia), pcDNA-3 (Invitrogen) or pET-15b (Novagen). The resulting construct can be introduced into a suitable host cell for expression. Upon expression, fusion protein can be isolated or purified from a cell lysate by means of a suitable affinity matrix (see e.g., *Current Protocols in Molecular Biology* (Ausubel, F. M. et al., eds., Vol. 2, Suppl. 26, pp. 16.4.1-16.7.8 (1991)). In addition, affinity labels provide a means of detecting a fusion protein. For example, the cell surface expression or presence in a particular cell fraction of a fusion protein comprising an antigen or epitope affinity label can be detected by means of an appropriate antibody.

Antibodies

The invention further relates to antibodies reactive with a mammalian CXCR3 protein or portion thereof. In a preferred embodiment, the antibodies specifically bind mammalian CXCR3 receptor(s) or a portion thereof. In one embodiment, antibodies are raised against an isolated and/or recombinant mammalian CXCR3 protein or portion thereof (e.g., a peptide) or against a host cell which expresses recombinant mammalian CXCR3.

Antibodies which can inhibit one or more functions characteristic of a mammalian (e.g., a primate such as a human) CXCR3 protein, such as a binding activity, a signalling activity, and/or stimulation of a cellular response, are also encompassed by the present invention. In one embodiment, antibodies of the present invention can inhibit binding of a ligand (i.e., one or more ligands) to a mammalian CXCR3 protein and/or can inhibit one or more functions mediated by a mammalian CXCR3 protein in response to ligand binding. In a particularly preferred embodiment, the antibodies can inhibit (reduce or prevent) the interaction of receptor with a natural ligand, such as IP-10 and/or Mig. For example, as shown herein, antibodies of the present invention can selectively inhibit the interaction of a human CXCR3 protein with IP-10 and/or selectively inhibit receptor functions in response thereto (e.g., signalling activity and/or a cellular response). An antibody designated 1C6 G, which displays this selectivity, can inhibit binding of IP-10 to a human CXCR3 protein as well as calcium flux and chemotaxis induced by IP-10, but does not significantly inhibit calcium flux induced by Mig under the same conditions. As shown herein, additional antibodies can inhibit IP-10 binding to CXCR3 (e.g., 3A8, 2F8, 3A12, 3E2, 4B4, 4D2, 5B12, 7B8 and 8D5) or IP-10-induced chemotaxis (e.g., 1A5, 3A8, 5F10, and 10C6), although these antibodies did not inhibit Mig-induced signalling under the conditions used, indicating that they are also selective inhibitors of the interaction of a human CXCR3 protein with IP-10 and/or of receptor functions in response thereto.

In a particularly preferred embodiment, the antibodies of the present invention have specificity for a human CXCR3 protein, and even more preferably have an epitopic specificity which is the same as or similar to that of a murine monoclonal antibody (mAb) designated 1C6. Antibodies having an epitopic specificity which is the same as or similar to that of mAb 1C6 can be identified using one or more suitable techniques for characterizing epitopic specificity. For example, antibodies having an epitopic specificity which is the same as or similar to that of mAb 1C6 can be identified by their ability to compete with murine mAb 1C6 for binding to a human CXCR3 protein or portion thereof (e.g., to cells bearing human CXCR3, including lymphocytes such as activated T cells, NK cells, or recombinant host cells comprising a nucleic acid of the present invention). In one embodiment, antibodies having an epitopic specificity which is the same as or similar to that of mAb 1C6 are further characterized by the ability of a polypeptide having a sequence which is the same as that of residues 1-15 ("P1") of SEQ ID NO:2 to inhibit binding of the antibodies to a human CXCR3 protein in a suitable assay (see e.g., Example 8). In one aspect of this embodiment, binding to a human CXCR3 protein by such antibodies is not significantly inhibited by a polypeptide having a sequence which is the same as that of residues 16-30 ("P2") or 31-45 ("P3") of SEQ ID NO:2.

Other antibodies encompassed by the present invention include antibodies which can bind to a human CXCR3 protein, wherein said binding can be inhibited by a portion of SEQ ID NO:2 corresponding to the N-terminal extracellular segment or a portion thereof. Suitable portions of the N-terminal extracellular segment include N-terminal, internal or C-terminal portions of that segment, such as a polypeptide comprising the N-terminus and having a sequence which is the same as that of residues 1-30, 1-45 or 1-58 of SEQ ID NO:2, for example, or a polypeptide having a sequence which is the same as that of residues 16-30 or 45-58 of SEQ ID NO:2. In a preferred embodiment, such portions have "at least one immunological property" of a mammalian CXCR3 protein as defined hereinabove, wherein the mammal is a human. For example, antibodies reactive with a human CXCR3 protein for which binding can be inhibited by a polypeptide having a sequence which is the same as that of residues 16-30 of SEQ ID NO:2 have been obtained (Example 9).

The antibodies of the present invention can be polyclonal or monoclonal, and the term antibody is intended to encompass both polyclonal and monoclonal antibodies. The terms polyclonal and monoclonal refer to the degree of homogeneity of an antibody preparation, and are not intended to be limited to particular methods of production.

Antibodies of the present invention can be raised against an appropriate immunogen, including proteins or polypeptides of the present invention, such as isolated and/or recombinant mammalian CXCR3 protein or portion thereof (including synthetic molecules such as synthetic peptides). In addition, cells expressing recombinant mammalian CXCR3, such as transfected cells, can be used as immunogens or in a screen for antibody which binds receptor. See for example, Chuntharapai et al., *J. Immunol.*, 152: 1783-1789 (1994); and Chuntharapai et al., U.S. Pat. No. 5,440,021.

Preparation of immunizing antigen, and polyclonal and monoclonal antibody production can be performed using any suitable technique. A variety of methods have been described (see e.g., Kohler et al., *Nature*, 256: 495-497 (1975) and *Eur. J. Immunol.* 6: 511-519 (1976); Milstein et al., *Nature* 266: 550-552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity can used, including, for example, methods which select recombinant antibody from a library, or which rely upon immunization of transgenic animals (e.g., mice) capable of producing a full repertoire of human antibodies (see e.g., Jakobovits et al., *Proc. Natl. Acad. Sci. USA*, 90: 2551-2555 (1993); Jakobovits et al., *Nature*, 362: 255-258 (1993); Lonberg et al., U.S. Pat. No. 5,545,1806; Surani et al., U.S. Pat. No. 5,545,807).

Single chain antibodies, and chimeric, humanized or primatized (CDR-grafted), or veneered antibodies, as well as chimeric, CDR-grafted or veneered single chain antibodies, comprising portions derived from different species, and the like are also encompassed by the present invention and the term "antibody". The various portions Or these antibodies can be joined together chemically by conventional techniques, or a polypeptide(s) can be prepared as a contiguous protein using genetic engineering techniques. The term "humanized antibody or immunoglobulin" as used herein refers to an antibody or immunoglobulin comprising portions of immunoglobulins of different origin, wherein at least one portion is of human origin. Accordingly, the present invention relates to a humanized antibody (including antigen-binding fragments thereof) having binding specificity for a mammalian CXCR3 protein (e.g., a human CXCR3 protein), comprising antigen binding regions of nonhuman origin (e.g., rodent) and at least of portion of an immunoglobulin of human origin (e.g., a human framework region, a human constant region, or portions thereof). For example, humanized antibodies can comprise portions derived from an immunoglobulin of nonhuman origin with the requisite specificity (e.g., a nonhuman mouse variable region) and from immunoglobulin sequences of human origin (e.g., a human constant region or portion thereof) joined together chemically or prepared as a contiguous polupeptide using genetic engineering techniques. Another example of a humanized antibody of the invention is an immunoglobulin comprising one or more immunoglobulin chains, said immunoglobulin comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one aspect of this embodiment, the immunoglobulin comprises the light chain CDRs (CDR1, CDR2 and CDR3) and heavy chain CDRs (CDR1, CDR2, CDR3) of a nonhuman immunoglobulin. In one embodiment, the humanized immunoglobulin has an epitopic specificity which is the same or similar to that mAB 1C6. In a preferred embodiment, the antigen binding region of the humanized immunoglobulin is derived from mAb 1C6. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

In addition, functional fragments of antibodies, including fragments of chimeric, humanized, primatized, veneered or single chain antibodies, can also be produced. Functional fragments of foregoing antibodies retain at least one binding function and/or modulation function of the full-length antibody from which they are derived. For example, antibody fragments capable of binding to a mammalian CXCR3 protein or portion thereof, including, but not limited to, Fv, Fab, Fab' and F(ab')$_2$ fragments are encompassed by the invention. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH$_1$ domain and hinge region of the heavy chain.

The antibodies of the present invention are useful in a variety of applications, including research, diagnostic and therapeutic applications. For instance, they can be used to isolate, purify and/or detect receptor or portions thereof, and to study receptor structure (e.g., conformation) and function.

The antibodies of the present invention can also be used to modulate receptor function in research and therapeutic applications. For instance, antibodies can act as inhibitors to inhibit (reduce or prevent) (a) binding (e.g., of a ligand, a second inhibitor or a promoter) to the receptor, (b) receptor signalling, and/or (c) a cellular response. Antibodies which act as inhibitors of receptor function can block ligand or promoter binding directly or indirectly (e.g., by causing a conformational change in the receptor). For example, antibodies can inhibit receptor function by inhibiting binding of a ligand, or by desensitization (with or without inhibition of binding of a ligand). Antibodies of the present invention can be used as antagonists of effector cells such as activated or stimulated T lymphocytes and natural killer (NK) cells, and find use in methods of therapy (including prophylaxis) of diseases or conditions which can be treated with inhibitors of CXCR3 function as described herein. Antibodies which can selectively inhibit the interaction of a human CXCR3 protein with IP-10 and/or selectively inhibit receptor functions in response thereto (e.g., mAb 1C6, antibodies having an epitopic specificity similar to that of mAb 1C6) are particularly useful in the treatment of diseases or disorders mediated by IP-10-CXCR3 interaction. For example, inflammatory conditions such as psoriasis, inflammatory bowel diseases, nephritis, and multiple sclerosis can be particularly amenable to therapy.

Surprisingly, mAb 1C6 inhibits T cell activation as assessed in a mixed lymphocyte reaction (MLR). Accordingly, mAb 1C6 and other anti-CXCR3 antibodies which can inhibit T cell activation, can be used to inhibit T cell activation and function(s) associated with activation, such as cytokine production, cytotoxic T cell killing, and/or provision of T cell help. When used in methods of therapy or prophylaxis as described herein, such antibodies can have the added advantage of inhibiting further T cell activation. Such antibodies are particularly attractive as therapeutic agents for treating graft rejection (e.g., in transplantation), including allograft rejection or graft-versus-host disease, or other diseases or conditions in which inhibition of the activation of T cells is desired.

Antibodies which bind receptor can also act as agonists of receptor function, triggering or stimulating a receptor function, such as signalling and/or a cellular response (e.g., calcium flux, chemotaxis, exocytosis or pro-inflammatory mediator release) upon binding to receptor. Accordingly, such antibodies can be used as agonists of effector cells such as activated or stimulated T lymphocytes and natural killer (NK) cells, and find use in methods of therapy (including prophylaxis) of diseases or conditions which can be treated with promoters of CXCR3 function as described herein.

In addition, the various antibodies of the present invention can be used to detect or measure the expression of receptor, for example, on leukocytes such as activated T cells or natural killer cells (NK cells), or on cells transfected with a receptor gene. Thus, they also have utility in applications such as cell sort.-ng (e.g., flow cytometry, fluorescence activated cell sorting), for diagnostic or research purposes.

Anti-idiotypic antibodies are also provided. Anti-idiotypic antibodies recognize antigenic determinants associated with the antigen-binding site of another antibody. Anti-idiotypic antibodies can be prepared against a first antibody by immunizing an animal of the same species, and preferably of the same strain as the animal used to produce the first antibody, with said first antibody. See e.g., U.S. Pat. No. 4,699,880.

In one embodiment, antibodies are raised against receptor or a portion thereof, and these antibodies are used in turn as immunogen to produce an anti-idiotypic antibody. The anti-Id produced thereby can mimic receptor and bind compounds which bind receptor, such as ligands, inhibitors or promoters of receptor function, and can be used in an immunoassay to detect, identify or quantitate such compounds. Such an anti-idiotypic antibody can also be an inhibitor of receptor function, although it does not bind receptor itself.

Anti-idiotypic (i.e., Anti-Id) antibody can itself be used to raise an anti-idiotypic antibody (i.e., Anti-anti-Id). Such an antibody can be similar or identical in specificity to the original immunizing antibody. In one embodiment, antibody antagonists which block binding to receptor can be used to raise Anti-Id, and the Anti-Id can be used to raise Anti-anti-Id, which can have a specificity which is similar or identical to that of the antibody antagonist. These anti-anti-Id antibodies can be assessed for inhibitory effect on receptor function to determine if they are antagonists.

Single chain, and chimeric, humanized, primatized (CDR-grafted), veneered, as well as chimeric, CDR-grafted, or veneered single chain anti-idiotypic antibodies can be prepared, and are encompassed by the term anti-idiotypic antibody. Antibody fragments of such antibodies can also be prepared.

The antibodies and fragments of the present invention can be modified, for example, by incorporation of or attachment (directly or indirectly) of a detectable label such as a radioisotope, spin label, antigen or enzyme label, flourescent or chemiluminesent group and the like, and such modified forms are included within the scope of the invention.

Identification of Ligands, Inhibitors or Promoters of Receptor Function

As used herein, a ligand is a substance which binds to a receptor protein. A ligand of a selected mammalian CXCR3 protein is a substance which binds to the selected mammalian CXCR3 protein. In a preferred embodiment, ligand binding of a mammalian CXCR3 protein occurs with high affinity. The term ligand refers to substances including, but not limited to, a natural ligand, whether isolated and/or purified, synthetic, and/or recombinant, a homolog of a natural ligand (e.g., from another mammal), antibodies, portions of such molecules, and other substances which bind receptor. A natural ligand of a selected mammalian receptor can bind to the receptor under physiological conditions, and is of a mammalian origin which is the same as that of the mammalian CXCR3 protein. The term ligand encompasses substances which are inhibitors or promoters of receptor activity, as well as substances which selectively bind receptor, but lack inhibitor or promoter activity.

As used herein, an inhibitor is a substance which inhibits at least one function characteristic of a mammalian CXCR3 protein (e.g., a human CXCR3), such as a binding activity (e.g., ligand binding, promoter binding), a signalling activity (e.g., activation of a mammalian G protein, induction of rapid and transient increase in the concentration of cytosolic free calcium $[Ca^{2+}]_i$), and/or cellular response function (e.g., stimulation of chemotaxis, exocytosis or inflammatory mediator release by leukocytes). The term inhibitor refers to substances including antagonists which bind receptor (e.g., an antibody, a mutant of a natural ligand, other competitive inhibitors of ligand binding), and substances which inhibit receptor function without binding thereto (e.g., an anti-idiotypic antibody).

As used herein, a promoter is a substance which promotes (induces or enhances) at least one function characteristic of a mammalian CXCR3 protein (e.g., a human CXCR3), such as a binding activity (e.g., ligand, inhibitor and/or promoter binding), a signalling activity (e.g., activation of a mammalian G protein, induction of rapid and transient increase in the concentration of cytosolic free calcium $[Ca^{2+}]_i$), and/or a cellular response function (e.g., stimulation of chemotaxis, exocytosis or inflammatory mediator release by leukocytes). The term promoter refers to substances including agonists which bind receptor (e.g., an antibody, a homolog of a natural ligand from another species), and substances which promote receptor function without binding thereto (e.g., by activating an associated protein). In a preferred embodiment, the agonist is other than a homolog of a natural ligand.

The assays described below, which rely upon the nucleic acids and proteins of the present invention, can be used, alone or in combination with each other or other suitable methods, to identify ligands, inhibitors or promoters of a mammalian CXCR3 protein or variant. The in vitro methods of the present invention can be adapted for high-throughput screening in which large numbers of samples are processed (e.g., a 96 well format). Host cells comprising a nucleic acid of the present invention and expressing recombinant mammalian CXCR3 (e.g., human CXCR3) at levels suitable for high-throughput screening can be used, and thus, are particularly valuable in the identification and/or isolation of ligands, inhibitors and promoters of mammalian CXCR3 proteins. Expression of receptor can be monitored in a variety of ways. For instance, expression can be monitored using antibodies of the present invention which bind receptor or a portion thereof. Also, commercially available antibodies can be used to detect expression of an antigen- or epitope-tagged fusion protein comprising a receptor protein or polypeptide (e.g., FLAG tagged receptors), and cells expressing the desired level can be selected.

Nucleic acid encoding a mammalian CXCR3 protein, the can be incorporated into an expression system to produce a receptor protein or polypeptide as described above. An isolated and/or recombinant receptor protein or polypeptide, such as a receptor expressed in cells stably or transiently transfected with a construct comprising a nucleic acid of the present invention, or in a cell fraction containing receptor (e.g., a membrane fraction from transfected cells, liposomes incorporating receptor) can be used in tests for receptor function. The receptor can be further purified if desired. Testing of receptor function can be carried out in vitro or in vivo.

An isolated and/or recombinant mammalian CXCR3 protein, such as a human CXCR3 as shown in FIG. 2 (SEQ ID NO:2), can be used in the present method, in which the effect of a compound is assessed by monitoring receptor function as described herein or using other suitable techniques. For example, stable or transient transfectants such as those described in Example 2 or other suitable cells (e.g., baculovirus infected Sf9 cells, stable tranfectants of mouse L1-2 pre-B cells (derived from a pre-B lymphoma, Dr. Eugene Butcher (Stanford University, Stanford, Calif.)), can be used in binding assays. Stable transfectants of Jurkat cells (Example 2) or of other suitable cells capable of chemotaxis can be used (e.g., mouse L1-2 pre-B cells) in chemotaxis assays, for example.

According to the method of the present invention, compounds can be individually screened or one or more compounds can be tested simultaneously according to the methods herein. Where a mixture of compounds is tested, the compounds selected by the processes described can be separated (as appropriate) and identified by suitable methods (e.g., PCR, sequencing, chromatography). The presence of one or more compounds (e.g., a ligand, inhibitor, promoter) in a test sample can also be determined according to these methods.

Large combinatorial libraries of compounds (e.g., organic compounds, recombinant or synthetic peptides, "peptoids", nucleic acids) produced by combinatorial chemical synthesis or other methods can be tested (see e.g., Zuckerman, R. N. et al., *J. Med. Chem.*, 37: 267B-2685 (1994) and references cited therein; see also, Ohlmeyer, M. H. J. et al., *Proc. Natl. Acad. Sci. USA* 90:10922-10926 (1993) and DeWitt, S. H. et al., *Proc. Natl. Acad. Sci. USA* 90:6909-6913 (1993), relating to tagged compounds; Ratter, W. J. et al. U.S. Pat. No. 5,010,175; Huebner, V. D. et al., U.S. Pat. No. 5,182,366; and Geysen, H. M., U.S. Patent No. 4,833,092). Where compounds selected from a combinatorial library by the present method carry unique tags, identification of individual compounds by chromatographic methods is possible.

In one embodiment, phage display methodology is used. For example, receptor can be contacted with a phage (e.g., a phage or collection of phage such as a library) displaying a polypeptide under conditions appropriate for receptor binding (e.g., in a suitable binding buffer). Phage bound to receptor can be selected using standard techniques or other suitable methods. Phage can be separated from receptor using a suitable elution buffer. For example, a change in the ionic strength or pH card lead to a release of phage. Alternatively, the elution buffer can comprise a release component or components designed to disrupt binding of compounds (e.g., one or more compounds which can disrupt binding of the displayed peptide to the receptor, such as a ligand, inhibitor, and/or promoter which competitively inhibits binding). Optionally, the selection process can be repeated or another selection step can be used to further enrich for phage which bind receptor. The displayed polypeptide can be characterized (e.g., by sequencing phage DNA). The polypeptides identified can be produced and further tested for ligand binding, inhibitor and/or promoter function. Analogs of such peptides can be produced which will have increased stability or other desirable properties.

In one embodiment, phage expressing and displaying fusion proteins comprising a coat protein with an N-terminal peptide encoded by random sequence nucleic acids can be produced. Suitable host cells expressing a receptor protein or polypeptide of the present invention are contacted with the phage, bound phage are selected, recovered and characterized. (See e.g., Doorbar, J. and G. Winter, *J. Mol. Biol.*, 244: 361 (1994) discussing a phage display procedure used with a G protein-coupled receptor).

Other sources of potential ligands, inhibitors and/or promoters of mammalian CXCR3 proteins include, but are not limited to, variants of CXCR3 ligands, including naturally occurring, synthetic or recombinant variants of IP-10 or Mig, substances such as other chemoattractants or chemokines, variants thereof, other inhibitors and/or promoters (e.g., anti-CXCR3 antibodies, antagonists, agonists), other G-protein coupled receptor ligands, inhibitors and/or promoters (e.g., antagonists or agonists), and soluble portions of a mammalian CXCR3 receptor, such as a suitable receptor peptide or analog which can inhibit receptor function (see e.g., Murphy, R. B., WO 94/05695).

Binding Assays

The isolated and/or recombinant receptor proteins or functional variants thereof, including portions thereof or suitable fusion proteins, can be used in a method to select and identify agents which bind to a (one or more) mammalian CXCR3 protein, such as human CXCR3, and which are ligands, or potential inhibitors or promoters of receptor activity. Agents selected by the method, including ligands, inhibitors or promoters, can be further assessed for an inhibitory or stimulatory effect on receptor function and/or for therapeutic utility.

In one embodiment, an agent which binds to an active, isolated and/or recombinant mammalian CXCR3 protein or polypeptide is identified by the method. In this embodiment, the receptor protein or polypeptide used has at least one property, activity or function characteristic of a mammalian CXCR3 protein (as defined herein), such as a binding activity (e.g., ligand, inhibitor and/or promoter binding), a signalling activity (e.g., activation of a mammalian G protein, induction of rapid and transient increase in the concentration of cytosolic free calcium [$Ca^{2+}$]$_i$), cellular response function (e.g., stimulation of chemotaxis, exocytosis or inflammatory mediator release by leukocytes), and/or an immunological property as defined herein. In a preferred embodiment, the isolated and/or recombinant mammalian CXCR3 protein or variant has ligand binding function, and more preferably binds a natural ligand of the receptor. In a particularly preferred embodiment, the isolated and/or recombinant protein is a human CXCR3 protein encoded by the nucleic acid illustrated FIG. 1 (SEQ ID NO:1).

For example, a composition comprising an isolated and/or recombinant mammalian CXCR3 protein or variant thereof can be maintained under conditions suitable for binding, the receptor can be contacted with an agent (e.g., a composition comprising one or more agent) to be tested, and binding is detected or measured. In one embodiment, a receptor protein can be expressed in cells stably or transiently transfected with a construct comprising a nucleic acid sequence which encodes a receptor of the present invention. The cells can be maintained under conditions appropriate for expression of receptor. The cells are contacted with an agent under conditions suitable for binding (e.g., in a suitable binding buffer), and binding can be detected by standard techniques. For example, the extent of binding can be determined relative to a suitable control (e.g., compared with background determined in the absence of agent, compared with binding of a second agent (i.e., a standard), compared with binding of the agent to untransfected cells). Optionally, a cellular fraction, such as a membrane fraction, containing receptor can be used in lieu of whole cells.

Binding or complex formation can be detected directly or indirectly. In one embodiment, the agent can be labeled with a suitable label (e.g., fluorescent label, chemiluminescent label, isotope label, enzyme label), and binding can be determined by detection of the label. Specificity of binding can be assessed by competition or displacement, for example, using unlabeled agent or a ligand (e.g., IP-10, Mig) as competitor.

Ligands of the mammalian receptor, including natural ligands from the same mammalian species or from another species, can be identified in this manner. The binding activity of a promoter or inhibitor which binds receptor can also be assessed using such a ligand binding assay.

Binding inhibition assays can also be used to identify ligands, and inhibitors and promoters which bind receptor and inhibit binding of another agent such as a ligand. For example, a binding assay can be conducted in which a reduction in the binding of a first agent (in the absence of a second agent), as compared with binding of the first agent in the presence of the second test agent, is detected or measured. The receptor can be contacted with the first and second agents simultaneously, or one after the other, in either order. A reduction in the extent of binding of the first agent in the presence of the second test agent, is indicative of inhibition of binding by the second agent. For example, binding of the first agent could be decreased or abolished.

In one embodiment, direct inhibition of the binding of a first agent (e.g., a chemokine such as IP-10, Mig) to a human CXCR3 by a second test agent is monitored. For example, the ability of an agent to inhibit the binding of $^{125}$I-labeled Mig to human CXCR3 can be monitored. Such an assay can be conducted using whole cells (e.g., a suitable cell line containing nucleic acid encoding a human CXCR3 receptor), or a membrane fraction from said cells, for instance.

Other methods of identifying the presence of an agent(s) which binds a receptor are available, such as methods which monitor events which are triggered by receptor binding, including signalling function and/or stimulation of a cellular response.

It will be understood that the inhibitory effect of antibodies of the present invention can be assessed in a binding inhibition assay. Competition between antibodies for receptor binding can also be assessed in the method in which the first agent in the assay is another antibody, under conditions suitable for antibody binding.

Ligands, receptor-binding inhibitors and promoters, which are identified in this manner, can be further assessed to determine whether, subsequent to binding, they act to inhibit or activate other functions of CXCR3 receptors and/or to assess their therapeutic utility.

Signalling Assays

The binding of a G protein-coupled receptor (e.g., by an agonist) can result in signalling by the receptor, and stimulation of the activity of G protein. The induction of signalling function by an agent can be monitored using any suitable method. For example, G protein activity, such as hydrolysis of GTP to GDP, or later signalling events triggered by receptor binding, such as induction of rapid and transient increase in the concentration of intracellular (cytosolic) free calcium [$Ca^{2+}$]$_i$, can be assayed by methods known in the art or other suitable methods (Example 2; see also, Neote, K. et al., *Cell*, 72: 415-425 1993); Van Riper et al., *J. Exp. Med.*, 177: 851-856 (1993); Dahinden, C. A. et al., *J. Exp. Med.*, 179: 751-756 (1994)).

The functional assay of Sledziewski et al. using hybrid G protein coupled receptors can also be used to identify a ligand or promoter by its ability to activate a hybrid G protein or to identify an inhibitor by its ability to inhibit such activation (Sledziewski et al., U.S. Pat. No. 5,284,746, the teachings of which are incorporated herein by reference). In one embodiment, a biological response of the host cell (triggered by binding to hybrid receptor) can be monitored, detection of the response being indicative of the presence of ligand in the test sample. For example, a method of detecting the presence of a ligand in a test sample is described, wherein the ligand is an agent which is capable of being bound by the ligand-binding domain of a receptor. In one embodiment of the method, yeast host cells are transformed with a DNA construct capable of directing the expression of a biologically active hybrid G protein-coupled receptor (i.e., a fusion protein). The hybrid receptor comprises a mammalian G protein-coupled receptor having at least one domain other than the ligand-binding domain replaced with a corresponding domain of a yeast G protein-coupled receptor, such as a STE2 gene product. The yeast host cells containing the construct are maintained under conditions in which the hybrid receptor is expressed, and the cells are contacted with a test sample under conditions suitable to permit binding of ligand to the hybrid receptor. A biological response of the host cell (triggered by binding to hybrid receptor) is monitored, detection of the response being indicative of a signalling function. For instance, binding to a hybrid receptor derived from STE2 gene product can lead to induction of the BAR1 promoter. Induction of the promoter can be measured by means of a reporter gene (e.g., β-gal), which is linked to the BAR1 promoter and introduced into host cells on a second construct. Expression of the reporter gene can be detected by an in vitro enzyme assay on cell lysates or by the presence of blue colonies on plates containing an indicator (e.g., X-gal) in the medium, for example.

In another embodiment, the assay can be used to identify potential inhibitors of receptor function. The inhibitory activity of an agent can be determined using a ligand or promoter in the assay, and assessing the ability of the test agent to inhibit the activity induced by ligand or promoter.

Variants of known ligands can also be screened for reduced ability (decreased ability or no ability) to stimulate activity of a coupled G protein. In this embodiment, although the agent has ligand binding activity (as determined by another method), engagement of the receptor does not trigger or only weakly triggers activity of a coupled G protein. Such agents are potential antagonists, and can be further assessed for inhibitory activity.

Chemotaxis and Other Assays of Cellular Responses

Chemotaxis assays can also be used to assess receptor function. These assays are based on the functional migration of cells in vitro or in vivo induced by an agent, and can be used to assess the binding and/or effect on chemotaxis of ligands, inhibitors, or promoters.

The use of an in vitro chemotaxis assay to assess the response of cells to IP-10 and Mig is described in Example 2. Springer et al. describe a transendothelial lymphocyte chemotaxis assay (Springer et al., WO 94/20142, published Sep. 15, 1994, the teachings of which are incorporated herein by reference; see also Berman et al., *Immunol Invest.*, 17: 625-677 (1988)). Migration across endothelium into collagen gels has also been described (Kavanaugh et al., *J. Immunol*, 146: 4149-4156 (1991)).

Generally, chemotaxis assays monitor the directional movement or migration of a suitable cell capable of chemotaxis, such as a leukocyte (e.g., T lymphocytes, NK cells, monocytes), stable transfectants of Jurkat cells, mouse L1-2 pre-B cells or of other suitable host cells, for example, into or through a barrier (e.g., endothelium, a filter) toward increased levels of an agent, from a first surface of the barrier toward an opposite second surface. Membranes or filters provide convenient barriers, such that the directional movement or migration of a suitable cell into or through a filter, toward increased levels of an agent, from a first surface of the filter toward an opposite second surface of the filter, is monitored. In some assays, the membrane is coated with a substance to facilitate adhesion, such as ICAM-1, fibronectin or collagen.

For example, one can detect or measure the migration of cells in a suitable container (a containing means), from a first chamber into or through a microporous membrane into a second chamber which contains an agent to be tested, and which is divided from the first chamber by the membrane. A suitable membrane, having a suitable pore size for monitoring specific migration in response to the agent, including, for example, nitrocellulose, polycarbonate, is selected. For example, pore sizes of about 3-8 microns, and preferably about 5-8 microns can be used. Pore size can be uniform on a filter or within a range of suitable pore sizes.

To assess migration, the distance of migration into the filter, the number of cells crossing the filter that remain adherent to the second surface of the filter, and/or the number of cells that accumulate in the second chamber can be determined using standard techniques (e.g., by microscopy). In one embodiment, the cells are labeled with a detectable label (e.g., radioisotope, fluorescent label, antigen or epitope label), and migration can be assessed by determining the presence of the label adherent to the membrane and/or present in the second chamber using an appropriate method (e.g., by detecting radioactivity, fluorescence, immunoassay). The extent of migration induced by an agent can be determined relative to a suitable control (e.g., compared to background migration determined in the absence of the agent, to the extent of migration induced by a second agent (i.e., a standard), compared with migration of untransfected cells induced by the agent).

Chambers can be formed from various solids, such as plastic, glass, polypropylene, polystyrene, etc. Membranes which are detachable from the chambers, such as a BIOCOAT (Collaborative Biomedical Products) or TRANSWELL (COSTAR, Cambridge, Mass.) culture insert, facilitate counting adherent cells. In the container, the filter can be situated so as to be in contact with fluid containing cells in the first chamber, and the fluid in the second chamber. Other than the test agent or additional ligand, inhibitor, or promoter present for the purpose of the assay, the fluid on either side of the membrane is preferably the same or substantially similar. The fluid in the chambers can comprise protein solutions (e.g., bovine serum albumin, fetal calf serum, human serum albumin) which may act to increase stability and inhibit nonspecific binding of cells, and/or culture media.

In one embodiment, transendothelial migration is assessed. In addition to lower background (signal to noise ratio), transendothelial migration models in vivo conditions in which leukocytes emigrate from blood vessels toward chemoattractants present in the tissues at sites of inflammation by crossing the endothelial cell layer lining the vessel wall. In this embodiment, transmigration through an endothelial cell layer assessed. To prepare the cell layer, endothelial cells can be cultured on a microporous filter or membrane, optionally coated with a substance such as collagen, fibronectin, or other extracellular matrix proteins, to facilitate the attachment of endothelial cells. Preferably, endothelial cells are cultured until a confluent monolayer is formed. A variety of mammalian endothelial cells can are available for monolayer formation, including for example, vein, artery or microvascular endothelium, such as human umbilical vein endothelial cells (CLONETICS CORP, San Diego, Calif.) or a suitable cell line, such as the ECV 304 cell line used (European Collection of Animal Cell Cultures, Porton Down, Salisbury, U.K.). To assay chemotaxis in response to a particular mammalian receptor, endothelial cells of the same mammal are preferred; however endothelial cells from a heterologous mammalian species or genus can also be used.

Generally, the assay is performed by detecting the directional migration of cells into or through a membrane or filter, in a direction toward increased levels of an agent, from a first surface of the filter toward an opposite second surface of the filter, wherein the filter contains an endothelial cell layer on a first surface. Directional migration occurs from the area adjacent to the first surface, into or through the membrane, towards an agent situated on the opposite side of the filter. The concentration of agent present in the area adjacent to the second surface, is greater than that in the area adjacent to the first surface.

In one embodiment, a chemotaxis assay is used to test for ligand or promoter activity of an agent, a composition comprising cells capable of migration and expressing a mammalian CXCR3 protein or functional variant thereof are placed in the first chamber, and a composition comprising the agent (one or more agents) to be tested is placed in the second chamber, preferably in the absence of other ligands or promoters capable of inducing chemotaxis of the cells in the first chamber (having chemoattractant function). However, one or more ligands or promoters having chemoattractant function may be present. The ability of an agent to induce chemotaxis of the cells expressing a mammalian CXCR3 receptor in this assay is indicative that the agent is a ligand or promoter of receptor function.

In one embodiment used to test for an inhibitor, a composition comprising cells capable of migration and expressing a mammalian CXCR3 protein or functional variant are placed in the first chamber. A composition comprising a ligand or promoter (i.e., one or more ligands or promoters) capable of inducing chemotaxis of the cells in the first chamber (having chemoattractant function) is placed in the second chamber. Before (preferably shortly before) the cells are placed in the first chamber, or simultaneously with the cells, a composition comprising the agent to be tested is placed, preferably, in the first chamber. The ability of an agent to inhibit ligand- or promoter-induced chemotaxis of the cells expressing a mammalian CXCR3 protein in this assay is indicative that the agent is an inhibitor of receptor function (e.g., an inhibitor of cellular response function). A reduction in the extent of migration induced by the ligand or promoter in the presence of the test agent, is indicative of inhibitory activity. Separate binding studies (see above) can be performed to determine whether inhibition is a result of binding of the test agent to receptor or occurs via a different mechanism.

In vivo assays which monitor leukocyte infiltration of a tissue, in response to injection of an agent in the tissue, are described below. These models measure the ability of cells to respond to a ligand or promoter by emigration and chemotaxis to a site of inflammation.

The effects of a ligand, inhibitor or promoter on the cellular response function of a CXCR3 receptor can be assessed by monitoring other cellular responses induced by active receptor, using suitable host cells containing receptor. Similarly, these assays can be used to determine the function of a receptor. For instance, exocytosis (e.g., degranulation of natural killer cells leading to release of one or more enzymes or other granule components, such as esterases (e.g., serine esterases), perforin, and/or granzymes), inflammatory mediator release (such as release of bioactive lipids such as leukotrienes (e.g., leukotriene $C_4$)), and respiratory burst, can be monitored by methods known in the art or other suitable methods. (See e.g., Taub, D. D. et al., *J. Immunol.*, 155: 3877-3888 (1995), regarding assays for release of granule-derided serine esterases (the teachings of which are incorporated herein by reference) and Loetscher et al., *J. Immunol.*, 156: 322-327 (1996), regarding assays for enzyme and granzyme release by NK cells and cytotoxic T lymphocytes (CTLs) (the teachings of which are incorporated herein by reference); Rot, A. et al., *J. Exp. Med.*, 176: 1489-1495 (1992) regarding respiratory burst; Bischoff, S. C. et al., *Eur. J. Immunol.*, 23: 761-767 (1993) and Baggliolini, M. and C. A. Dahinden, *Immunology Today*, 15: 127-133 (1994)).

In one embodiment, a ligand, inhibitor and/or promoter is identified by monitoring the release of an enzyme upon degranulation or exocytosis by a cell capable of this function. Cells containing a nucleic acid of the present invention, which encodes an active receptor protein capable of stimulating exocytosis or degranulation are maintained in a suitable medium under suitable conditions, whereby receptor is expressed and degranulation can be induced. The receptor is contacted with an agent to be tested, and enzyme release is assessed. The release of an enzyme into the medium can be detected or measured using a suitable assay, such as in an immunological assay, or biochemical assay for enzyme activity.

The medium can be assayed directly, by introducing components of the assay (e.g., substrate, co-factors, antibody) into the medium (e.g., before, simultaneous with or after the cells and agent are combined). Alternatively, the assay can be performed on medium which has been separated from the cells or further processed (e.g., fractionated) prior to assay. For example, convenient assays for are available for enzymes such serine esterases (see e.g., Taub, D. D. et al., *J. Immunol.*, 155: 3877-3888 (1995) regarding release of granule-derived serine esterases).

Stimulation of degranulation by an agent can be indicative that the agent is a ligand or promoter of a mammalian CXCR3 protein. In another embodiment, cells expressing receptor are combined with a ligand or promoter, and an agent to be tested is added before, after or simultaneous therewith, and degranulation is assessed. Inhibition of ligand- or promoter-induced degranulation is indicative that the agent is an inhibitor of mammalian CXCR3 protein function.

Cellular adherence can also monitored by methods known in the art or other suitable methods. Engagement of the chemokine receptors of a lymphocyte can cause integrin activation, and induction of adherence to adhesion molecules expressed in vasculature or the perivascular space. In one embodiment, a ligand, inhibitor and/or promoter is identified by monitoring cellular adherence by a cell capable of adhesion. For example, an agent to be tested can be combined with (a) cells expressing receptor (preferably non-adherent cells which when transfected with receptor aquire adhesive ability), (b) a composition comprising a suitable adhesion molecule (e.g., a substrate such as a culture well coated with an adhesion molecule, such as fibronectin), and (c) a ligand or promoter (e.g., agonist), and maintained under conditions suitable for ligand- or promoter-induced adhesion. Labeling of cells with a fluorescent dye provides a convenient means of detecting adherent cells. Nonadherent cells can be removed (e.g., by washing) and the number of adherent cells determined. The effect of the agent in inhibiting or enhancing ligand- or promoter-induced adhesion can be indicative of inhibitor or promoter activity, respectively. Agents active in the assay include inhibitors and promoters of binding, signalling, and/or cellular responses. In another embodiment, an agent to be tested can be combined with cells expressing receptor and a composition comprising a suitable adhesion molecule under conditions suitable for ligand- or promoter-induced adhesion, and adhesion is monitored. Increased adhesion relative to a suitable control is indicative of the presence of a ligand and/or promoter.

Models of Inflammation

A variety of in vivo models of inflammation are available, which can be used to assess the effects of ligands, inhibitors, or promoters in vivo as therapeutic agents, including a sheep model for asthma (see e.g., Weg, V. B. et al., *J. Exp. Med.*, 177: 561 (1993), the teachings of which are incorporated herein by reference), a rat delayed type hypersensitivity model (Rand, M. L. et al., *Am. J. Pathol.*, 148: 855-864 (1996), the teachings of which are incorporated herein by reference), or other suitable models. The activity of antibodies which cross-react with other mammalian CXCR3 proteins can be assessed in such mammals.

In addition, leukocyte infiltration upon intradermal injection of a compound into a suitable animal, such as rabbit, rat, or guinea pig, can be monitored (see e.g., Van Damme J. et al., *J. Exp. Med.*, 176: 59-65 (1992); Zachariae, C. O. C. et al., *J. Exp. Med.*, 171: 2177-2182 (1990); Jose, P. J. et al., *J. Exp. Med.*, 179: 881-887 (1994)). In one embodiment, skin biopsies are assessed histologically for infiltration of leukocytes (e.g., T lymphocytes, monocytes, natural killer cells). In another embodiment, labeled cells (e.g., cells expressing a mammalian CXCR3 protein which are labeled with $^{111}$In, for example) capable of chemotaxis and extravasation are administered to the animal. Infiltration of labelled cells in the vicinity of the site of injection of a test sample (e.g., a compound to be tested in a suitable buffer or physiological carrier) is indicative of the presence of a ligand or promoter, such as an agonist, in the sample. These assays can also be modified to identify inhibitors of chemotaxis and leukocyte extravasation. For example, an inhibitor can be administered, either before, simultaneously with or after ligand or agonist is administered to the test animal. A decrease of the extent of infiltration in the presence of inhibitor as compared with the extent of infiltration in the absence of inhibitor is indicative of inhibition.

Diagnostic Applications

The present invention has a variety of diagnostic applications. For example, a mutation(s) in a gene encoding a mammalian CXCR3 protein can cause a defect in at least one function of the encoded receptor, thereby reducing or enhancing receptor function. For instance, a mutation which produces a variant of receptor or alters the level of expression, can reduce or enhance receptor function, reducing or enhancing processes mediated by receptor (e.g., inflammatory processes). The presence of such a mutation can be determined using methods which detect or measure the presence of receptor or receptor function in cells (e.g., leukocytes, such as activated T lymphocytes) of an individual or in a receptor preparation isolated from such cells. In these assays, reduced or enhanced levels of receptor and/or reduced or enhanced receptor function can be assessed.

The nucleic acids of the present invention provide reagents, such as probes and PCR primers, which can be used to screen for, characterize and/or isolate a defective mammalian CXCR3 gene, which encodes a receptor having reduced or enhanced activity. Standard methods of screening for a defective gene can be employed, for instance. A defective gene can be isolated and expressed in a suitable host cell for further assessment as described herein for mammalian CXCR3 proteins. A number of human diseases are associated with defects in the function of a G-protein coupled receptor (Clapham, D. E., *Cell*, 75: 1237-1239 (1993); Lefkowitz, R. J., *Nature*, 365: 603-04 (1993)).

The nucleic acids of the present invention provide reagents, such as probes and PCR primers, which can also be used to assess expression of receptor (e.g., by detecting transcription of mRNA) by cells in a sample (e.g., by Northern analysis, by in situ hybridization). For example, expression in activated T lymphocytes or other cell types can be assessed.

The antibodies of the present invention have application in procedures in which receptor can be detected on the surface of cells. The receptor provides a marker of the leukocyte cell types in which it is expressed, particularly of activated T cells. For example, antibodies raised against a receptor protein or peptide, such as the antibodies described herein (e.g., mAb 1C6), can be used to detect and/or quantify cells expressing receptor. In one embodiment, the antibodies can be used to sort cells which express receptor from among a mixture of cells (e.g., to isolate activated T cells, such as CD4$^+$ T cells). Suitable methods for counting and/or sorting cells can be used for this purpose (e.g., flow cytometry, fluorescence activated cell sorting). Cell counts can be used in the diagnosis of diseases or conditions in which an increase or decrease in leukocyte cell types (e.g., activated T cells) is observed. The presence of an increased level of activated T cells in a sample obtained from an individual can be indicative of infiltration due to an inflammatory disease or condition, such as a delayed type hypersensitivity reaction, allograft rejection, or a pathologic condition, including bacterial or viral infection.

Furthermore, the antibodies can be used to detect or measure expression of receptor. For example, antibodies of the present invention can be used to detect or measure receptor in a sample (e.g., tissues or body fluids from an individual such as blood, serum, leukocytes (e.g., activated T lymphocytes), bronchoalveolar lavage fluid, saliva, bowel fluid). For example, a sample (e.g., tissue and/or fluid) can be obtained from an individual and a suitable assay can be used to assess the presence or amount of CXCR3 protein. Suitable assays include immunological methods such as FACS analysis and enzyme-linked immunosorbent assays (ELISA), including chemiluminescence assays, radioimmunoassay, and immunohistology. Generally, a sample and antibody of the present invention are combined under conditions suitable for the formation of an antibody-receptor complex, and the formation of antibody-receptor complex is assessed (directly or indirectly).

The presence of an increased level of receptor reactivity in a sample obtained from an individual can be indicative of inflammation and/or leukocyte (e.g., activated T cell) infiltration and/or accumulation associated with an inflammatory disease or condition, such as allograft rejection, delayed type hypersensitivity reaction, or an infection such as a viral or bacterial infection. The level of expression of a mammalian CXCR3 protein or variant can also be used to correlate increased or decreased expression of a mammalian CXCR3 protein with a particular disease or condition, and in the diagnosis of a disease or condition in which increased or decreased expression of a mammalian CXCR3 protein occurs (e.g., increased or decreased relative to a suitable control, such as the level of expression in a normal individual). Similarly, the course of therapy can be monitored by assessing CXCR3 immunoreactivity in a sample from a patient. For example, antibodies of the present invention can be used to monitor the number of cells bearing CXCR3 in a sample (e.g., blood, tissue) from a patient being treated with an anti-inflammatory or immunosuppressive agent Transgenic Animals Transgenic animals, in which the genome of the animal host is altered using recombinant DNA techniques, can be constructed. In one embodiment, the alteration is not heritable (e.g., somatic cells, such as progenitor cells in bone marrow, are altered). In another embodiment, the alteration is heritable (the germ line is altered). Transgenic animals can be constructed using standard techniques or other suitable methods (see e.g., Cooke. M. P. et al., *Cell*, 65: 281-291 (1991) regarding alteration of T lymphocytes; Hanahan, D., *Science*, 246: 1265-1275, (1989); Anderson et al., U.S. Pat. No. 5,399, 346).

In one aspect, an endogenous mammalian CXCR3 gene can be inactivated or disabled, in whole or in part, in a suitable animal host (e.g., by gene disruption techniques) to produce a transgenic animal. Nucleic acids of the present invention can be used to assess successful construction of a host containing an inactivated or disabled CXCR3 gene (e.g., by Southern hybridization). In addition, successful construction of a host containing an inactivated or disabled CXCR3 gene can be assessed by suitable assays which monitor the function of the encoded receptor. Such animals can be used to assess the effect of receptor inactivation on inflammation and host defenses against cancer and pathogens (e.g., a viral pathogen).

In another embodiment, a nucleic acid encoding a mammalian CXCR3 protein or polypeptide is introduced into a suitable host to produce a transgenic animal. In a preferred embodiment, endogenous CXCR3 receptor genes present in the transgenic animals are inactivated (e.g., simultaneously with introduction of the nucleic acid by homologous recombination, which disrupts and replaces the endogenous gene). For example, a transgenic animal (e.g., a mouse, guinea pig, sheep) capable of expressing a nucleic acid encoding a mammalian CXCR3 receptor of a different mammalian species (e.g., a human CXCR3 such as the CXCR3 encoded by SEQ ID NO:1) in leukocytes (such as lymphocytes (e.g., activated T lymphocytes), natural killer cells) can be produced, and provides a convenient animal model far assessing the function of the introduced receptor. In addition, a test agent can be administered to the transgenic animal, and the effect of the agent on a receptor-mediated process (e.g., inflammation) can be monitored as described herein or using other suitable assays. In this manner, agents which inhibit or promote receptor function can be identified or assessed for in vivo effect.

Methods of Therapy

Modulation of mammalian CXCR3 function according to the present invention, through the inhibition or promotion of at least one function characteristic of a mammalian CXCR3 protein, provides an effective and selective way of inhibiting or promoting receptor-mediated functions. As CXC chemokine receptors selectively expressed on activated lymphocytes, responsive to chemokines such as IP-10 and Mig whose primary targets are lymphocytes, particularly effector cells such as activated or stimulated T lymphocytes and NK cells, mammalian CXCR3 proteins provide a target for selectively interfering with or promoting lymphocyte function in a mammal, such as a human. Once lymphocytes are recruited to a site, other leukocyte types, such as monocytes, may be recruited by secondary signals. Thus, agents which inhibit or promote CXCR3 function, including ligands, inhibitors (e.g., 1C6) and/or promoters, such as those identified as described herein, can be used to modulate leukocyte function (e.g., leukocyte infiltration including recruitment and/or accumulation) particularly of lymphocytes, for therapeutic purposes.

In one aspect, the present invention provides a method of inhibiting or promoting an inflammatory response in an individual in need of such therapy, comprising administering an agent which inhibits or promotes mammalian CXCR3 function to an individual in need of such therapy. In one embodiment, a compound which inhibits one or more functions of a mammalian CXCR3 protein (e.g., a human CXCR3) is administered to inhibit (i.e., reduce or prevent) inflammation. For example, antibodies of the present invention, including mAb 1C6 can be used in the method. As a result, one or more inflammatory processes, such as leukocyte emigration, chemotaxis, exocytosis (e.g., of enzymes) or inflammatory mediator release, is inhibited. For example, leukocytic infiltration of inflammatory sites (e.g., in a delayed-type hypersensitivity response) can be inhibited according to the present method.

In another embodiment, an agent (e.g., receptor agonist) which promotes one or more functions of a mammalian CXCR3 protein (e.g., a human CXCR3) is administered to induce (trigger or enhance) an inflammatory response, such as leukocyte emigration, chemotaxis, exocytosis (e.g., of enzymes) or inflammatory mediator release, resulting in the beneficial stimulation of inflammatory processes. For example, natural killer cells can be recruited to combat viral infections or neoplastic disease.

The term "individual" is defined herein to include animals such as mammals, including, but not limited to, primates (e.g., humans), cows, sheep, goats, horses, dogs, cats, rabbits, guinea pigs, rats, mice or other bovine, ovine, equine, canine, feline, rodent or murine species. Diseases and conditions associated with inflammation, infection, and cancer can be treated using the method. In a preferred embodiment, the disease or condition is one in which the actions of lymphocytes, particularly effector cells such as activated or stimulated T lymphocytes and natural killer (NK) cells, are to be inhibited or promoted for therapeutic (including prophylactic) purposes. In a particularly preferred embodiment, the inflammatory disease or condition is a T cell-mediated disease or condition.

Diseases or conditions, including chronic diseases, of humans or other species which can be treated with inhibitors of CXCR3 function, include, but are not limited to:

inflammatory or allergic diseases and conditions, including systemic anaphylaxis or hypersensitivity responses, drug allergies (e.g., to penicillin, cephalosporins), insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis (e.g., necrotizing, cutaneous, and hypersensitivity vasculitis); spondyloarthropathies; scleroderma; respiratory allergic diseases such as asthma, allergic rhinitis, hypersensitivity lung diseases, hypersensitivity pneumonitis, interstitial lung diseases (ILD) (e.g., idiopathic pulmonary fibrosis, or ILD associated with rheumatoid arthritis, or other autoimmune conditions);

autoimmune diseases, such as arthritis (e.g., rheumatoid arthritis, psoriatic arthritis), multiple sclerosis, systemic lupus erythematosus, myasthenia gravis, diabetes, including diabetes mellitus and juvenile onset diabetes, glomerulonephritis and other nephritides, autoimmune thyroiditis, Behcet's disease;

graft rejection (e.g., in transplantation), including allograft rejection or graft-versus-host disease;

other diseases or conditions in which undesirable inflammatory responses are to be inhibited can be treated, including, but not limited to, atherosclerosis, cytokine-induced toxicity, myositis (including polymyositis, dermatomyositis).

Diseases or conditions of humans or other species which can be treated with promoters (e.g., an agonist) of CXCR3 function, include, but are not limited to:

cancers, particularly those with leukocytic infiltration of the skin or organs such as cutaneous T cell lymphoma (e.g., mycosis fungoides);

diseases in which angiogenesis or neovascularization plays a role, including neoplastic disease, retinopathy (e.g., diabetic retinopathy), and macular degeneration;

infectious diseases, such as bacterial infections and tuberculoid leprosy, and especially viral infections;

immunosuppression, such as that in individuals with immunodeficiency syndromes such as AIDS, individuals undergoing radiation therapy, chemotherapy, or other therapy which causes immunosuppression; immunosuppression due congenital deficiency in receptor function or other causes. Promoters of CXCR3 function can also have protective effects useful to combat stem cell depletion during cancer chemotherapy (Sarris, A. H. et al., *J. Exp. Med.*, 178: 1127-1132 (1993)).

Modes of Administration

According to the method, one or more agents can be administered to the host by an appropriate route, either alone or in combination with another drug. An effective amount of an agent (e.g., a receptor peptide which inhibits ligand binding, an anti-CXCR3 antibody or antigen-binding fragment thereof) is administered. An effective amount is an amount sufficient to achieve the desired therapeutic or prophylactic effect, under the conditions of administration, such as an amount sufficient for inhibition or promotion of CXCR3 receptor function, and thereby, inhibition or promotion, respectively, of a receptor-mediated process (e.g., an inflammatory response).

A variety of routes of administration are possible including, but not necessarily limited to oral, dietary, topical, parenteral (e.g., intravenous, intraarterial, intramuscular, subcutaneous injection), and inhalation (e.g., intrabronchial, intranasal or oral inhalation, intranasal drops) routes of administration, depending on the agent and disease or condition to be treated. For respiratory allergic diseases such as asthma, inhalation is a preferred mode of administration.

Formulation of an agent to be administered will vary according to the route of administration selected (e.g., solution, emulsion, capsule). An appropriate composition comprising the agent to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, *Remington's Pharmaceutical Sciences*, 17th Edition, Mack Publishing Co., PA, 1985). For inhalation, the agent can be solubilized and loaded into a suitable dispenser for administration (e.g., an atomizer, nebulizer or pressurized aerosol dispenser).

Furthermore, where the agent is a protein or peptide, the agent can be administered via in vivo expression of the recombinant protein. In vivo expression can be accomplished via somatic cell expression according to suitable methods (see, e.g. U.S. Pat. No. 5,399,346). In this embodiment, nucleic acid encoding the protein can be incorporated into a retroviral, adenoviral or other suitable vector (preferably, a replication deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically effective amount.

EXEMPLIFICATION

The present invention will now be illustrated by the following Examples, which are not intended to be limiting in any way.

Human Chemokines (Examples 1-2)

The CXC chemokines Mig, IL-8, GROα, NAP-2, GCP-2, ENA78, PF4, the CC chemokines MCP-1, MCP-2, MCP-3, MCP-4, MIP-1α, MIP-1β, RANTES, I309, eotaxin and the chemokine-related lymphotactin were chemically synthesized according to established protocols (Clark-Lewis, I. et al., *Biochemistry* 30: 3128-3135 (1991)). The CXC chemokine IP-10 was purchased from PeproTech, Rocky Hill, N.J.

Example 1

Cloning of Receptor cDNA

Standard molecular biology techniques were used (Sambrook, J. et al., 1989, *Molecular Cloning: A Laboratory Manual*, Cold Spring Harbor Laboratory Press, Cold Spring Harbor, NY).

DNA fragments coding for putative T lymphocyte-restricted chemokine receptors were generated using the polymerase chain reaction (PCR). Two degenerate oligonucleotide primers were designed based on conserved motifs of chemokine receptors. Primer design was based on the conserved nucleotide sequences within transmembrane domain 2 (TM2) and transmembrane domain 7 (TM7) of the chemokine receptors IL-8RI (CXCR1), IL-8R2 (CXCR2), CC-CKR1 (CCR1), CC-CKR2 (CCR2) and the orphan receptors EBI I, LESTR, and BLR1/MDR15 (EBI I, Birkenbach, M. et al., *J. Virol.*, 67: 2209-2220 (1993)); LESTR, Loetscher, M. et al., *J. Biol. Chem.*, 269: 232-237 (1994); and BLR1/MDR15, Dobner, T. et al., *Eur. J. Immunol.*, 22: 2795-2799 (1992) and Barella, L. et al., *Biochem. J.*, 309: 773-779 (1995)).

The sequences of the primers were as follows;
SEQ ID NO:3:
  5'-GGG CTG CAG CII T(T/G) (T/G) C(C/A)G AC(A/C) TIC TI(C/T) T-3'
SEQ ID NO:4:
  5'-GGG TCT AGA IGG GTT IAI (G/A)CA (G/A)C(T/A) (G/A) (T/C)G-3'

(I=inosine). These primers were used in a polymerase chain reaction (PCR) to amplify DNA fragments using human genomic DNA isolated from human peripheral blood lymphocytes as template as follows. A 100 μl reaction mixture containing 2 μg human genomic DNA, 1×DynaZyme buffer (Finnzymes OY, Espoo, Finland), 1.5 mM MgCl$_2$, 500 μM of each deoxynucleotide, 1 μM of both primers, and 2.5 U of DynaZyme DNA polymerase was subjected to 30 cycles (94° C. for 1 minute; 55° C. for 1 minute; and 72° C. for 2 minutes) on a DNA thermal cycler (Techne PHC-2, Brouwer, Switzerland) PCR products of the predicted size (approximately 700 bp) were cloned into the Gene Scribe-Z vectors pTZ18/19 U/R (USB, Cleveland, OH), were partially sequenced (Sanger, F. et al., *Proc. Natl. Acad. Sci. USA*, 74: 5463-5467 (1977)), and were evaluated for their similarity to known chemokine receptors and for expression of their corresponding mRNA in leukocytes. A DNA fragment designated 2MLC22 revealed 64% nucleotide sequence identity with IL-8R2. Fragment 2MLC22 specifically hybridized to RNA from T cells, but not monocytes or neutrophils, as assessed by Northern blot analysis using a hybridization probe prepared by enzymatically labeling 2MLC22 with the radioactive isotope $^{32}$P using Klenow fragment of DNA Polymerase I and a commercially available random-prime labeling kit.

Fragment 2MLC22 was enzymatically labeled with $^{32}$P as described and used as a probe to screen a human tetanus toxoid-specific CD4$^+$ T cell (KT30) cDNA library, prepared in lambda-ZAP Express (STRATAGENE GMBH, Zurich, Switzerland) (Loetscher, M. et al., *J. Bid. Chem.*, 269: 232-237 (1994)). A cDNA library was prepared in a λ ZAP Express system according to the manufacturer's protocol (STRATAGENE GMBH, Zurich, Switzerland) using poly (A)$^+$ RNA from human tetanus toxoid-specific CD4$^+$ T cells (KT30). The resulting library contained about 1.8×10$^6$ independent clones with an average insert size of approximately 1.1 kb. For plaque hybridization screening, about 4×10$^5$ clones were transferred onto Biodyne nylon membranes (PALL A G, Muttenz, Switzerland) and probed with 2MLC22 which had been labeled to a specific activity of $1 \times 10^9$ dpm/µg DNA using the high prime DNA labeling kit (BOEHIRINGER MANNHEIM, Mannheim, Germany). Hybridization was carried out in 50% formamide, 6×SSC, 0.5% SDS, 100 µg/ml denatured salmon sperm DNA at 42° C. for 20 hours using $1 \times 10^6$ dpm 2MLC22/ml hybridization solution. The membranes were washed once in 2×SSC, 0.1% SDS at room temperature for 10 minutes, twice in 1×SSC, 0.1% SDS at 65° C. for 30 minutes, and finally once in 0.5×SSC, 0.1% SDS at 65° C. for 10 minutes. Twenty-three clones were isolated from hybridization positive lambda plaques following the high stringency washes, and the clone with the largest insert (1670 bp) was sequenced. CXCR3 cDNA was subcloned into commercially available plasmid vectors for nucleotide sequencing, generation of hybridization probes, and construction of stably transfected mammalian cell clones expressing CXCR3, and these CXCR3 cDNA-containing constructs are maintained in E. coli strains.

Results

A cDNA was isolated from a human CD4+ T cell library by searching for T lymphocyte-specific chemokine receptors (FIG. 1, SEQ ID NO:1). This cDNA was not recovered in the course of searching a commonly used monocyte-derived cDNA library or granulocyte (HL60)-derived cDNA library for novel chemokine receptor cDNAs; however, a direct search of the libraries specifically for CXCR3 cDNA has not been conducted. The CXCR3 cDNA, which was shown to encode an IP-10/Mig receptor (see below), and has an open reading frame (ORF) of 1104 bp beginning at residue 69 which encodes a protein of 368 amino acids with a predicted molecular mass of 40,659 daltons. The amino acid sequence (FIG. 2, SEQ ID NO:2) includes seven putative transmembrane segments, which are characteristic of G-protein coupled receptors, and three potential N-glycosylation sites ($Asn^{22}$, $Asn^{32}$, and $Asn^{199}$) (FIG. 2). In addition, one threonine and nine serine residues, which are potential phosphorylation sites for receptor kinases (Palczewski, K. and J. L. Benovic, Trends Biochem. Sci., 16: 387-391 (1991); Chuang, T. T. et al., J. Biol. Chem., 267: 6886-6892 (1992); and Giannini, E. et al., J. Biol. Chem., 270: 19166-19172 (1995)), can be found in the intracellular COOH-terminal region (FIG. 2).

The 368 amino acid sequence of the receptor (IP-10/MigR, FIG. 2, SEQ ID NO:2) was aligned with the amino acid sequences of other human chemokine receptors, including IL-8R1 (CXCR1), IL-8R2 (CXCR2), CC-CKR1 (CCR1), CC-CKR2A (CCR2a), CC-CKR3 (CCR3) and CC-CKR4 (CCR4). Multiple protein alignment was performed according to Higgins and Sharp (Higgins, D. G. and P. M. Sharp, "Description of the method used in CLUSTAL," Gene, 73: 237-244 (1988)). Double-underlined residues in FIG. 2 represent regions of identity between IP-10/MigR and at least two other chemokine receptors. Hyphens indicate gaps in the alignment. The alignment revealed several conserved motifs, particularly in the transmembrane domains and the second intracellular loop. Significant sequence identity with CXC receptors IL-8R1 and IL-8R2, but not with the CC chemokine receptors, was observed in the third and the sixth transmembrane domains (FIG. 2).

The sequence shares 40.9% and 40.3% amino acid identity overall with the IL-8R1 and IL-8R2 receptors, respectively, and 34.2 to 36.9% identity with the five known CC chemokine receptors (Table 1). A lower degree of similarity was found with seven-transmembrane-domain receptors that are expressed in T cells, but which do not bind chemokines, e.g., 27.2% identity with the thrombin receptor (Vu, T.-K. H. et al., Cell, 64: 1057-1068 (1991)). A truncated clone of unidentified function, with an incomplete coding sequence which can be aligned with that of FIG. 2, was previously isolated from a human genomic DNA library (Marchese, A. et al., Genomics, 29: 335-344 (1995)).

TABLE 1

Amino Acid Sequence Comparison of IP-10/MigR with Human Chemokine Receptors

| | IL-8R1 (CXCR1) | IL-8R2 (CXCR2) | CC-CKR1 (CCR1) | CC-CKR2A (CCR2a) | CC-CKR3 (CCR3) | CC-CKR4 (CCR4) | CC-CKR5 (CCR5) | ThrombR |
|---|---|---|---|---|---|---|---|---|
| IP-10/MigR | 40.9[a] | 40.3 | 34.9 | 34.2 | 34.4 | 35.8 | 36.9 | 27.2 |
| IL-8R1 | | 77.1 | 33.7 | 32.9 | 34.3 | 39.7 | 34.3 | 29.1 |
| IL-8R2 | | | 34.9 | 33.6 | 34.1 | 40.8 | 34.4 | 29.7 |
| CC-CKR1 | | | | 54.1 | 63.1 | 49.3 | 56.3 | 26.8 |
| CC-CKR2A | | | | | 50.7 | 46.1 | 68.8 | 24.6 |
| CC-CKR3 | | | | | | 46.5 | 52.3 | 27.3 |
| CC-CKR4 | | | | | | | 50.0 | 29.2 |
| CC-CKR5 | | | | | | | | 23.6 |

[a]Numbers refer to percentage amino acid identity. Pairwise protein sequence alignments were carried out using the program PALIGN with an open gap cost and unit gap cost of 3 and 2, respectively.

Example 2

Biological Activity

Expression in Activated T Lymphocytes

In view of the observed chemokine selectivity, the occurrence of the IP-10/MigR in leukocytes and related cell lines was examined by Northern blot analysis. 10 µg samples of total RNA were examined from freshly isolated human blood monocytes, neutrophils, lymphocytes (PBL), nylon-wool purified T cells, and from cultured cells including cloned human CD4+ T cells (KT30) and CD8+ T cells (ERCD8), cloned NK cells (ERNK57), and PBL cultured for 10 days ($1-2.5 \times 10^6$ cells/ml in RPMI 1640 medium containing 2 mM glutamine, 1×non-essential amino acids, 1 mM sodium pyruvate, 100 µg/ml kanamycin, $5 \times 10^{-5}$ M 2-mercaptoethanol, and 5% human serum) in the presence of 400 U/ml hrIL-2. (human recombinant IL-2 was a gift of Dr. A. Lanzavecchia, Basel Institute of Immunology, Basel, Switzerland). Agarose gels were stained with ethidium bromide to check the integrity and amount of total RNA on the gel prior to blotting. RNA samples were analyzed with $^{32}$P-labeled 5'-fragment of the IP-10/MigR DNA ($10^9$ cpm/µg DNA) at $5 \times 10^6$ cpm/ml hybridization solution as described (Loetscher, M. et al., J. Biol. Chem., 269: 232-237 (1994)). The 5'-fragment used as a Northern probe was prepared by digestion of CXCR3 cDNA in pBK-CMV vector (Stratagene GMBH, Zurich, Switzerland) with PstI yielding the 724 bp 5'-end of the CXCR3 cDNA (FIG. 1).

Results

Abundant expression of mRNA of the expected size was found in the cloned CD4+ T cells, KT30, that were used for isolation of the receptor cDNA. Similar levels of expression were observed in the CD8+ T cell clone, EP-CD8, and the NK cell clone, ERNK57. In contrast, in freshly isolated blood lymphocytes and nylon-wool purified T cells, IL10/MigR transcripts were barely detectable. However, when these cells were cultured in the presence of IL-2, a strong upregulation was obtained, and the level of receptor mRNA approached that of T and NK cell clones. No IP-10/MigR transcripts were detected under these conditions in freshly isolated blood monocytes, neutrophil leukocytes, or eosinophil leukocytes. Additional leukocyte-related cells that did not express IP-10/MigR mRNA include the mast cell line, HMC-1, the promyelocytic leukemia line, HL60, the histiocytic lymphoma, U937, the chronic myelogenous leukemia line, K562, the acute T cell leukemia line, Jurkat, the acute lymphoblastic leukemia line, Molt, the B-lymphoblastic cell lines Daudi and Raji, lymphocytes from patients with chronic and acute B-lymphoid leukemia (B-CLL and B-ALL), mature basophils from a patient with basophilic leukemia, and the erythroleukemia cell line, HEL. By contrast, the receptors for chemokines which have been shown previously to attract lymphocytes, i.e. MCP-1 MCP-2, MCP-3, MIP-1α, MIP-1β and RANTES (Loetscher, P. et al., *FASEB J.*, 8: 1055-1060 (1994); Carr, M. W. et al., *Proc. Natl. Acad. Sci. USA* 91: 3652-3656 (1994); Taub, D. D. et al., *Science*, 260: 355-358 (1993); Schall, T. J. et al., *J. Exp. Med.*, 177: 1821-1825 (1993); Schall, T. J. et al., *Nature*, 347: 669-672 (1990)), are also found in monocytes and granulocytes. The restricted expression of ID-10/MigR in activated T lymphocytes and a natural killer cell line suggests that this novel receptor can mediate selective lymphocyte recruitment.

Stable Transfectants

CXCR3 cDNA was released from pBK-CMV (STRATAGENE GMBH, Zurich, Switzerland) by digestion with BamHI and XbaI, and was cloned into BamHI and XbaI sites of pcDNA3 (INVITROGEN BV, WB Leek, Netherlands) to yield pcDNA3-Clone8, which is maintained and stored in *Escherichia coli* (XL1Blue).

To generate stable transfectants, $4 \times 10^6$ of either mouse pre-B cells (300-19) (Thelen, M. et al., *FASEB. J.*, 2: 2702-2706 (1988)), human promyelocytic cells (GM-1) (Garotta, G. et al., *J. Leukocyte Biol.*, 49: 294-301 (1991)) or human acute T cell leukemia cells (Jurkat) (Loetscher, P. et al., *FEBS Lett.* 341: 187-192 (1994)), were transfected by electroporation with 20 µg of receptor cDNA in pcDNA3 which was linearized with Bgl II as described previously (Moser, B. et al., *Biochem. J.*, 294: 285-292 (1993)).

IP-10/MigR transfected cells were cloned by limiting dilution under G-418 (Life Technologies, Inc.) selection (1.0 mg/ml G-418 for 300-19 and 0.8 mg/ml G-418 for Jurkat and GM-1 cells). G-418 resistant clones were screened for receptor expression by RNA Dot-blot analysis.

$Ca^{2+}$ Flux

To determine whether the receptor was functional, clones of murine pre-B cells (300-19), human promyelccytic cells (GM-1), and human T cell leukemia cells (Jurkat) were stably transfected with receptor cDNA as described above. Activation of chemokine receptors leads to a transient rise in the cytosolic free $Ca^{2+}$ concentration ($[Ca^{2+}]_i$), and this assay was used to monitor signalling in the transfected cells.

Changes in the cytosolic free $Ca^{2+}$ concentration ($[Ca^{2+}]_i$) were measured in cells loaded with fura-2 by incubation for 30 minutes at 37° C. with 0.1 nmol fura-2 acetoxymethylester per 106 cells in a buffer containing 136 mM NaCl, 4.8 mM KCl, 1 mM $CaCl_2$, 5 mM glucose, and 20 mM HEPES, pH 7.4. After centrifugation, loaded cells were resuspended in the same buffer ($10^6$ cells/ml), stimulated with the indicated chemokine at 37° C., and the $[Ca^{2+}]_i$-related fluorescence changes were recorded (von Tscharner, V. et al., *Nature*, 324: 69-372 (1986)).

Results

A rapid $[Ca^{2+}]_i$ rise was observed in response to IP-10 and Mig. The chemokine IP-10 has been shown to be expressed in cutaneous delayed-type hypersensitivity reactions (Luster, A. D. et al., *Nature*, 315: 672-676 (1985); Kaplan, G. et al., *J. Exp. Med.*, 166: 1098-1108 (1987)). The chemokine designated Mig was recently identified (Farber, J. M., *Proc. Natl. Acad. Sci. USA*, 87: 5238-5242 (1990); Farber, J. M., *Biophys. Res. Commun.*, 192: 223-230 (1993)). Both chemokines have the CXC arrangement of the first two cysteines like IL-8, but are not chemotactic for neutrophil leukocytes. It was recently reported that IP-10 attracts T lymphocytes (Luster, A. D. and P. Leder, *J. Exp. Med.*, 178: 1057-1065 (1993); Taub, D. D. et al., *J. Exp. Med.*, 177: 1809-1814 (1993)), and that Mig is chemotactic for tumor-associated lymphocytes (Liao, F. et al., *J. Exp. Med.*, 182: 1301-1314 (1995)).

FIGS. 3A-3C summarize the effects of IP-10 and Mig on cells transfected with the cDNA and expressing the functional IP-10/MigR. As shown by the $[Ca^{2+}]_i$ changes (FIG. 3A), the action of IP-10 and Mig was concentration dependent and already detectable at 1 nM, indicating that both chemokines have high affinity for the novel receptor. The IP-10/MigR transfectants, by contrast, did not respond to any of 16 other potential agonists at concentrations up to 100 nM, including the CXC chemokines IL-8, GROα, NAP-2, GCP-2, ENA78, PF4, the CC chemokines MCP-1, MCP-2, MCP-3, MCP-4, MIP-1α, MIP-1β, RANTES, I309, eotaxin or the chemokine related lymphotactin (not shown). Identical results were obtained with the murine and the human transfected cells. These observations demonstrate that the novel receptor is highly selective for IP-10 and Mig. Accordingly, the receptor is referred to herein as an IP-10/Mig receptor (IP-10/MigR), or as "CXCR3", reflecting its specificity for CXC chemokines.

As shown in FIG. 3B, repeated stimulation with IP-10 or Mig resulted in desensitization typical of chemokine receptors. Furthermore, cross-desensitization occurred when the cells were stimulated with IP-10 followed by Mig or vice versa, confirming that the receptor has high affinity for both chemokines. At 100 nM concentration, it became evident that Mig was more potent in cross-desensitization than IP-10, suggesting higher affinity or binding stability of the IP-10/Mig receptor for Mig.

While expression of functional IP-10/MigR was demonstrated, binding experiments using radioactive ligands revealed non-specific binding between 60 and 80% of the total, preventing determination of binding parameters. Since IP-10 and Mig are highly cationic (pI values of 10.8 and 11.1), nonspecific interaction with cell surface proteoglycans may explain these results. Indeed, chemokine receptor-unrelated, heparinase-sensitive binding sites for IP-10 (and PF4) have been detected on a variety of blood and tissue cells (Luster, A. D. et al., *J. Exp. Med.*, 182: 219-231 (1995)), and heparan sulfate binds IP-10 and Mig and prevents lymphocyte chemotaxis (not shown). The heparin binding site is probably not involved in CXCR3 receptor binding, and inclusion of a suitable heparin derivative such as chondroitin sulfate in the reaction (e.g., in binding buffer) can be used to inhibit non-specific binding to cells through the heparin binding site.

Chemotaxis

PBL were freshly isolated from donor blood buffy coats. Donor blood buffy coats were provided by the Swiss Central Laboratory Blood Transfusion Service, SRK. Isolation of buffy coat PBL was performed as described in Colotta, F. et al., *J. Immunol.*, 132: 936-944 (1984).

Freshly isolated PBL from donor blood buffy coats were used without further processing, or were used after culturing for 10 days in the presence of IL-2 (1-2.5×10$^6$ cells/ml in RPMI 1640 medium containing 2 mM glutamine, 1× non-essential amino acids, 1 mM sodium pyruvate, 100 μg/ml kanamycin, 5×10$^{-5}$ M 2-mercaptoethanol, and 5% human serum in the presence of 400 U/ml hrIL-2).

Cell migration was assessed in 48-well chambers (Neuro Probe, Cabin John, Md., USA) using polyvinylpyrrolidone-free polycarbonate membranes (Nucleopore) with 5-μm pores for IP-10/MigR transfected cells (Loetscher, P. et al., *FEBS Lett.* 341: 187-192 (1994)) or with 3-μm pores for human PBL (Loetscher, P. et al., *FASEB J.*, 8: 1055-1060 (1994)) RPMI 1640 supplemented with 20 mM Hepes, pH 7.4, and 1% pasteurized plasma protein solution (Swiss Red Cross Laboratory, Bern, Switzerland) was used to dissolve the chemokines (lower wells), and to dilute the cells (100,000 receptor transfectants or PBL in the upper well). After 60 minutes at 37° C., the membrane was removed, washed on the upper side with PBS, fixed and stained. All assays were done in triplicate, and the migrated cells were counted in five randomly selected fields at 1,000-fold magnification. Spontaneous migration was determined in the absence of chemoattractant.

Results—Transfected Cells

Transfected cells expressing the IP-10/MigR readily migrated toward IP-10 or Mig, while the non-transfected, parental cells did not respond (FIG. 3C). Both agonists showed a typically biphasic concentration dependence IP-10 induced migration at concentrations above 1 nM, whereas the response of Mig became detectable above 10 nM. The efficacy, which is measured by the maximum number of migrating cells, was about twice as high for Mig as for IP-10. These results demonstrate that the IP-10/MigR, like all known chemokine receptors in leukocytes, mediates chemotaxis in response to ligand.

Results—Human Blood Leukocytes

In agreement with the cellular distribution of the IP-10/MigR, activated human T lymphocytes were found to be highly responsive to IP-10 and Mig (FIGS. 4A-4B). The activity of IP-10 and Mig as inducers of $[Ca^{2+}]_i$ changes (FIG. 4A) and in vitro chemotaxis (FIG. 4B) was consistent with the effects observed using transfected cells expressing the IP-10/MigR, with IP-10 being more potent but less efficacious than Mig. Activation of the T lymphocytes by culturing in the presence of IL-2 was required for induction of calcium flux and chemotaxis, and no response was observed with freshly isolated blood lymphocytes under the conditions used.

Materials and Methods for Examples 3-9

The following materials and methods were used in Examples 3-9.

Chemokines

Recombinant human chemokines were obtained from PEPROTECH (Rocky Hill, N.J.), except for eotaxin, described previously (Ponath, P. D., et al., *J. Clin. Invest.*, 97:604-612 (1996); see also Ponath et al., WO 97/00960, published 9 Jan. 1997), which was a gift from Dr. Ian Clark-Lewis. $^{125}$I-labeled chemokines were obtained from Du Pont NEN (Boston, Mass.).

Cells and Cell Lines

Neutrophils and PBMCs were isolated as described (Ponath, P. D., et al., *J. Clin. Invest.*, 97:604-612 (1996)). To generate CD3 blasts, 2×10$^6$ PBMC/ml in RPMI-1640 plus 10% FCS were added to tissue culture plates which had been coated with the anti-CD3 antibody TR66. After 4-6 days blasts were removed to fresh media and supplemented with IL-2 (kindly provided by Antonio Lanzavecchia, Basel) at 50 units/ml.

Other cell lines used included transfectants of the L1.2 murine pre B cell lymphoma, expressing either CXCR3 (see below), IL-8 RA (Ponath, P. D., et al., *J. Exp. Med.*, 183:2437-2448 (1996)), IL-8 RB (Ponath, P. D., et al., *J. Exp. Med.*, 183:2437-2448 (1996)), CCR2b (G. LaRosa, unpublished), CCR4, CCR5 (Wu, L., et al., *Nature*, 384:179-183 (1996)), or CCR1 (Campbell, J. J., et al., *J. Cell Biol.*, 134:255-266 (1996)).

Preparation of CXCR3 Transfectants

Cells

L1.2 cells were grown in RPMI medium 1640, 10% Fetal Clone (from Hyclone, Inc.), 50 U/ml Penicillin/Streptomycin, 1× L-Glutamine, 1 mM NaPyruvate, and 5.5×10$^{-5}$M β-Mercaptoethanol. Media components were purchased from GibcoBRL, except for 10% Fetal Clone, which was purchased from Hyclone, Inc. Two days prior to transfection, the L1.2 cells were diluted 1:5 into fresh medium. This resulted in 150 million cells in log phase growth at a concentration of about 1-3 million cells/ml.

CXCR3 DNA and Transfection

*E. coli* XL1Blue cells (STRATAGENE. INC. (Cat# 200236)) were transformed with pcDNA3-Clone8 (Example 2; Loetscher, M., et al., *J. Exp. Med.*, 184:963-969 (1996)) according to the manufacturer's protocol. Transformants were grown at 37° C. while shaking at 250 rpm in 500 ml of LB containing 100 μg/ml Ampicillin. The culture was then collected by centrifugation at 8,000×g, and the plasmid was purified using a Maxi plasmid purification column and protocol (QIAGEN, Cat# 12162). Plasmid concentration and purity were determined using a 1% agrose gel and OD260/280 ratios. Plasmid DNA was suspended in ddH$_2$O, and stored at −20° C. until use.

ScaI endonuclease was used to linearize the vector. 100 μg of DNA was digested with 10 μl of ScaI for 8 hours at 37° C. following the manufacturer's protocol (GibcoBRL, Cat# 15436-017). 20 μg was used directly in stable transfection construction. 80 μg was cleaned of proteins and salts with a Phenol:Chloroform:IsoAmyl Alcohol (25:24:1) extraction, 100% Ethanol precipitation (with 0.1 volume NH$_4$COOH), and a 70% ethanol wash.

Stable transfectants of murine pre-B lymphoma cell line (L1.2) were prepared essentially as described (Ponath, P. D., et al., *J. Exp. Med.*, 183:2437-2448 (1996)). 25 million L1.2 cells in 0.8 ml of 1×PBS were electroporated with 20 μg of linearized DNA, 20 μg linearized DNA that was then cleaned (see above under linearization of DNA), or without DNA. Before electroporation, the L1.2 cells and the DNA were incubated for 10 minutes in 50 ml conical tubes (Falcon Model 2070) with gentle mixing (swirling) every 2 minutes. The L1.2 cell-DNA mixture was transferred into Gene Pulser cuvettes (BioRad, Cat# 165-2088) with a 0.4 cm electrode gap. The mixture was then electroporated at 250V and 960 μF, with the duration of shock and the actual voltage being measured. After electroporation, the cuvette was left undisturbed for 10 minutes at room temperature. All of the L1.2 cells-DNA mixture was then transferred to a T-25 flask (Costar), and grown for two days in 10 ml non-selective medium.

Selection

L1.2 cells expressing CXCR3 were then subjected to selection for neomycin resistance. After two days of growth in non-selective medium, 10 ml of 1.6 g/L Geneticin (Gibco-BRL) was added for a final concentration of 0.8 g/L (The selective and maintenance concentration). This was then allowed to grow for 10 to 15 days, with fresh selective medium added when cells started to over-grow. Fresh selective medium consisted of RPMI-1640 supplemented with 10% bovine serum and 800 μg/ml G418.

The cell surface expression of CXCR3 was assessed by chemotaxis, and ligand binding and Scatchard analysis was also used to monitor surface expression. After G418 selection, CXCR3 expressing L1.2 cells were selected based on chemotaxis ability. For each electroporation reaction, 30 ml (800,000 cells/ml) were collected, and suspended in 600 μl selective medium. Selective medium, 600 μl, containing 10 nM IP-10, was placed into the bottom chamber of BIOCOAT cell culture plates from BECTON DICKINSON (Cat# 40575). 100 μl/well of the L1.2 cells were added into the top chamber of the BIOCOAT plates. These cells were then left to chemotax overnight in a $CO_2$ incubator at 37° C. The top chambers with the non-chemotaxing cells were removed. The chemotaxed cells were collected, transferred into fresh medium, and allowed to grow in a 24 well plate. They were subsequently expanded into a T-25 and then a T-75 flask from COSTAR.

Transfectants expressing high level of receptors were cloned by limiting dilution. CXCR3 transfected cells were diluted to between 30-3 cells/ml in selection medium containing G418. Aliquots were added to 96-well tissue culture plates at 100 μl/well. After 14 days at 37° C. and 5% $CO_2$, wells containing single colonies were identified under an inverted microscope. 50 μl of the cells were then transferred and stained with anti-CXCR3 mAb as above and analyzed by flow cytometry. The level of receptor expression correlated with mean fluorescence intensity and high expressors were selected. Once a stable cell line was established, the line was expanded for use.

In addition to selection for antibiotic resistance and chemotaxis, CXCR3 transfectant cells can be further selected by sorting for higher receptor expression by antibody staining, although this was not done here. For staining, transfectant cells can be resuspended at $5 \times 10^6$/ml in sterile PBS containing 1% bovine serum albumin. Isolated, sterile anti-CXCR3 mAb can be added to a final concentration of 3 μg/ml and cells incubated on ice for 30 minutes. After washing with cold sterile PBS, the bound mAb can be detected with FITC-conjugated anti-mouse IgG, sterilized by filtration through a 0.2 μm filter. The cells can be washed again and sorted by flow cytometry. The top 5% positive cells can be collected and returned to tissue culture for expansion under selective conditions (e.g., RPMI-1640 supplemented with 10% bovine serum and 800 μg/ml G418).

Example 3

IP-10 Binds with High Affinity to a Receptor Expressed on L1.2 Cells Transfected with CXCR3 DNA and on Activated T Cells Additional binding studies were performed using radiolabeled IP-10. Chemokine binding to target cells was carried out as described previously (Ponath, P. D., et al., *J. Clin. Invest.*, 97:604-612 (1996); Van Riper, G., et al., *J. Exp. Med.*, 177(3):851-856 (1993)). Cells were washed once in PBS and resuspended in binding buffer (50 mM HEPES, pH 7.5, 1 mM $CaCl_2$, 5 mM $MgCl_2$, 0.5% BSA, and 0.05% azide) at a concentration of $10^7$/ml. Aliquots of 50 μl ($5 \times 10^5$ cells) were dispensed into microfuge tubes, followed by the addition of cold competitor (unlabeled IP-10) and radiolabeled chemokine (0.05 nM $^{125}$I-labeled IP-10). The final reaction volume was 200 μl. Nonspecific binding was determined by incubating cells with radiolabeled chemokines in the presence of 250-500 nM of unlabeled chemokines. After a 60-minute incubation at room temperature, the cells were washed three times with 1 ml of binding buffer containing 0.5 M NaCl. Cell pellets were then counted. The competition was presented as the percent specific binding as calculated by $100 \times [(S-B)/(T-B)]$, where S is the radioactivity of the sample, B is background binding, and T is total binding without competitors. Background binding was obtained by incubating cells with radiolabeled chemokine and at least 400-fold excess of unlabeled chemokines. Duplicates were used throughout the experiments and the standard deviations were always <10% of the mean. All experiments were repeated at least three times. Curve fit and concentrations that inhibit 50% specific binding ($IC_{50}$) were calculated by KaleidaGraph software (Synergy Software, Reading, Pa.).

Figure 5A:
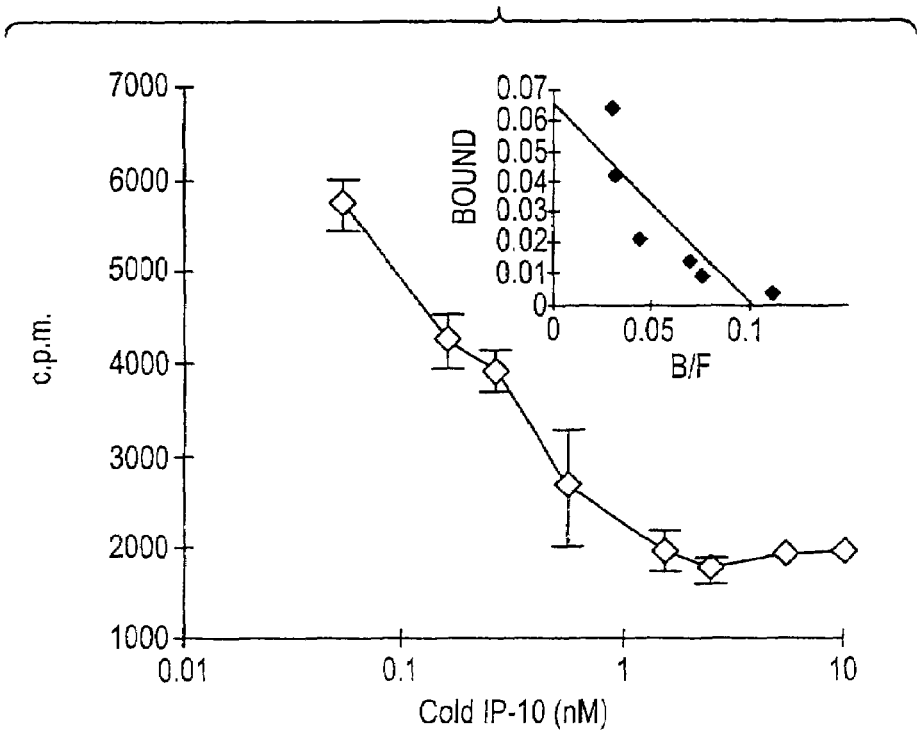
FIGS. 5A-5B are graphs illustrating the binding of radiolabeled IP-10 to either L1.2 cells transfected with CXCR3 DNA (FIG. 5A) and to activated T cells (FIG. 5B). Cells were incubated with 0.05 nM $^{125}$I-labeled IP-10 in the presence of increasing concentrations of unlabeled IP-10. Scatchard analysis (inset) indicated 37,000 receptors per cell (Kd of 614 pM) for CXCR3 L1.2 transfectants, and 17,000 receptors per cell (Kd of 156 pM) for CD3 blasts.
Figure 5B:
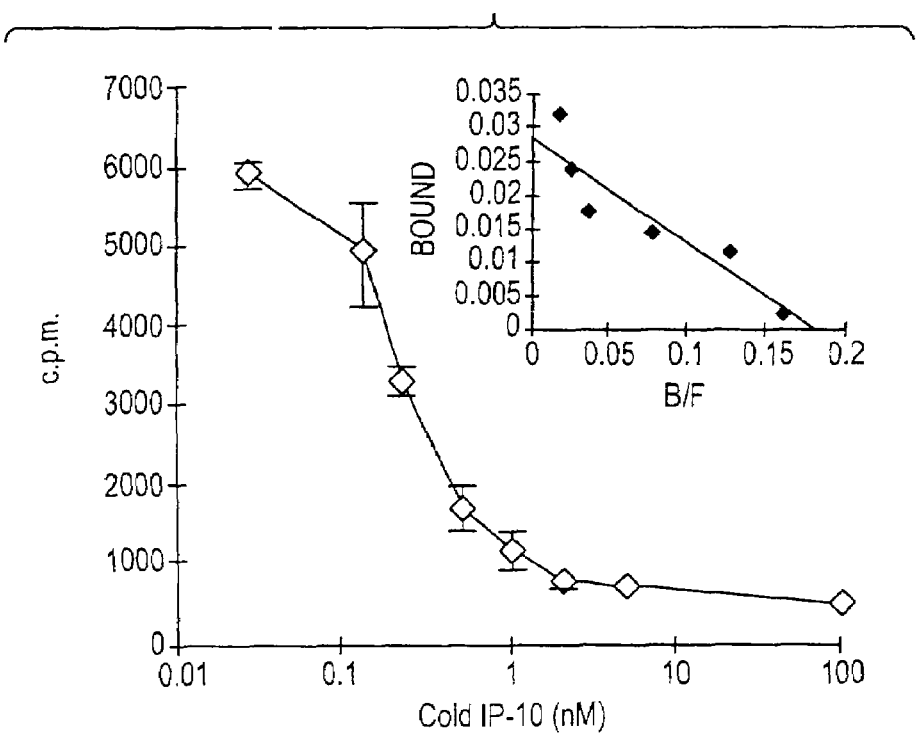

FIGS. 5A-5B show that $^{125}$I-labeled IP-10 bound to L1.2 cells transfected with CXCR3 (FIG. 5A) and to CD3-activated T cells (FIG. 5B), and that this binding could be inhibited with increasing concentrations of cold IP-10. Scatchard analysis revealed that IP-10 bound to L1.2 CXCR3 transfectants with a Kd of 614 pM, and that these transfectants expressed 37,000 receptors per cell (FIG. 5A, inset). A similar analysis of anti-CD3 activated, IL-2 stimulated T cells revealed a Kd of 156 pM, and 17,000 receptors per cell (FIG. 5B). $^{125}$I-labeled IP-10 binding to activated T cells could be totally inhibited by cold Mig under the same conditions, although Mig was slightly less efficient at blocking $^{125}$I-labeled IP-10 binding than was cold IP-10 (not shown). IP-10 and Mig bind CXCR3 with high affinity (Kd ~150-600 pM).

Example 4

Production and Characterization of Monoclonal Antibodies (mAbs) Specific for CXCR3

To develop antagonists of CXCR3, and to study receptor expression and regulation, a panel of mAbs was produced by immunizing mice with a synthetic peptide corresponding to the N-terminus of this receptor. These mAbs specifically recognized CXCR3 transfectants, but not a range of other receptor transfectants.

mAb Production and Flow Cytometry mAbs reactive with CXCR3 were generated by immunizing Balb/C mice with 10 μg of 37-mer synthetic peptide corresponding to the first 37 N-terminal amino acids of CXCR3 (see also, Loetscher M., et al., *J. Exp. Med.*, 184:963-969 (1996)), five times over a period of 10 weeks. This peptide was synthesized and coupled to purified protein derivative of tuberculin (Severn Biotech Ltd., Kidderminster, U.K.). The first immunization was intraperitoneal (IP) with Freund's Complete Adjuvant (FCA). The second, third and fourth immunizations were IP with Freund's Incomplete Adjuvant (FIA), and the final immunization was with peptide conjugate alone (no adjuvant), and was administered intravenously (IV). Four days after the last immunization, the spleen was taken and cell fusion performed using the cell line SP2/0, as described (Coligan, J. E., et al., Current Protocols In Immunology (John Wiley and Sons, New York), Unit 2.5.4 (1992)). mAbs were generated that reacted with the N-terminal 37-mer peptide as assessed by ELISA (Coligan, J. E., et al., Current Protocols In Immunology (John Wiley and Sons, New York), Unit 2.1.3 (1992)). mAbs reactive with CXCR3 were identified using untransfected and CXCR3 transfected L1.2 cells or 300.19 cells (a murine B cell line, Loetscher, M. et al., *J. Exp. Med.*, 184: 963-969, (1996)), and immunofluorescent staining and analysis using a FACScan® (Becton Dickinson & Co., Mountain View, Calif.).

Figure 6:
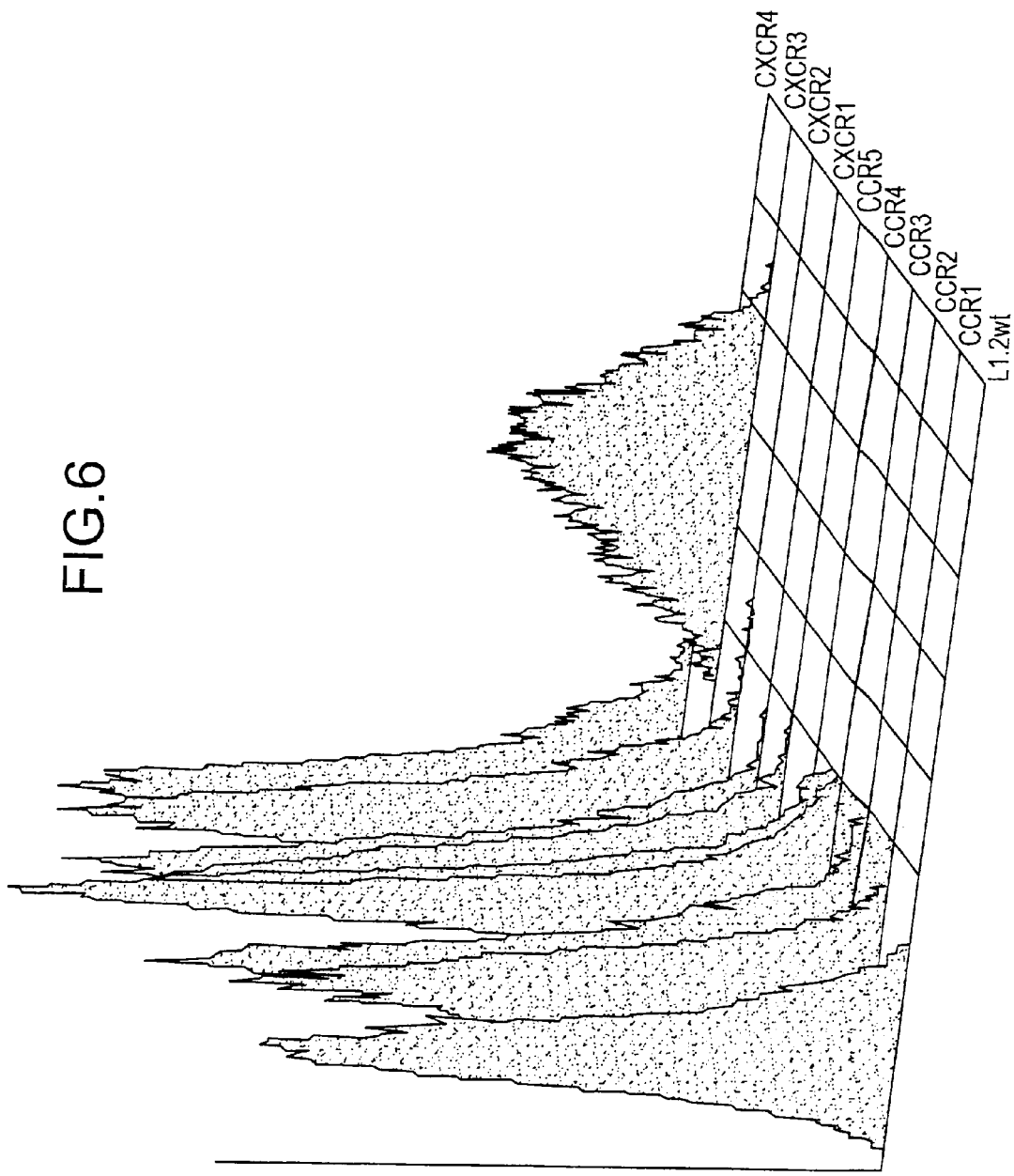
FIG. 6 is an illustration of the specificity of anti-CXCR3 antibody 1C6 as assessed by staining of stable L1.2 transfectants expressing either CCR1, CCR2b, CCR3, CCR4, CCR5, CXCR1, CXCR2, CXCR3 or CXCR4 by anti-CXCR3 peptide mAb 1C6. Negative control staining for all the L1.2 transfectants (not shown) resembled the staining shown for 1C6 on untransfected L1.2 cells (L1.2 wt).
Figure 7A:
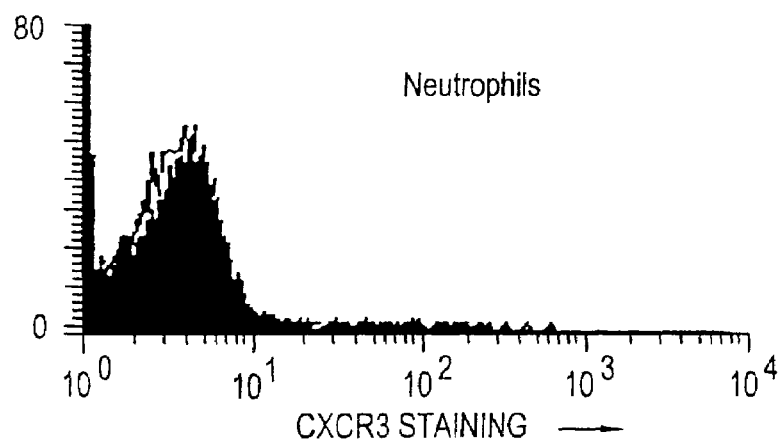
FIGS. 7A-7C are fluorescence histograms illustrating the expression of CXCR3 on neutrophils (FIG. 7A), lymphocytes (FIG. 7B), and activated T cells (FIG. 7C) Leukocyte subsets were identified in whole blood by their forward angle and side scatter, and were gated accordingly. To generate CD3 blasts, PBMC were activated with anti-CD3 mAb for 3 days, and were then maintained in media containing IL-2 for 7 days. In each plot, the blackened profile represents staining with anti-CXCR3 mAb 1C6, and the unfilled profile represent staining with an isotype-matched control mAb.
Figure 7B:
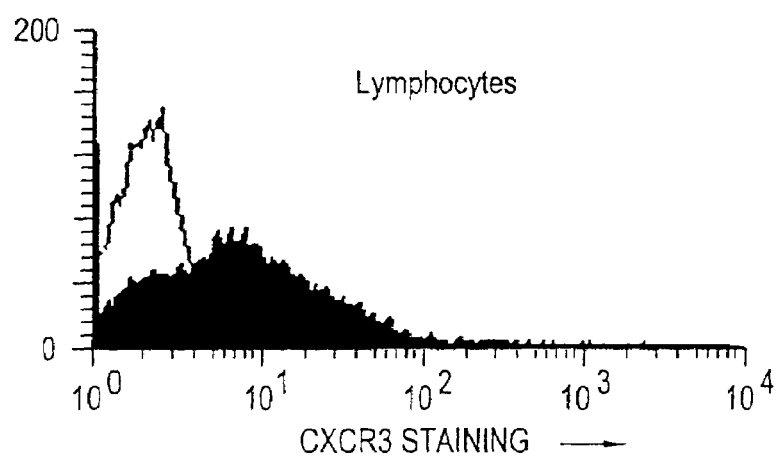
Figure 7C:
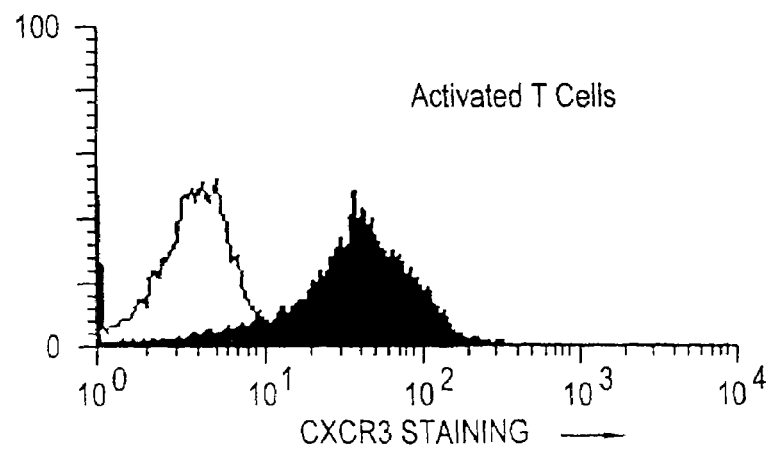

Monoclonal antibodies specific for CXCR3 were generated. Eight mAbs were found to recognize surface expressed CXCR3, as judged by staining of CXCR3 transfected L1.2 cells, but not untransfected L1.2 cells or L1.2 cells transfected with other receptor types. The FACS profile of one of these mAbs, 1C6, is shown in FIG. 6. These mAbs also stained human T cells and T cell clones that had been activated in vitro with PHA or anti-CD3 (illustrated in FIG. 7C with 1C6). However, these anti-CXCR3 mAbs were unreactive with neutrophils (illustrated in FIG. 7A with 1C6), monocytes, or eosinophils (not shown). This pattern of reactivity was consistent with the analysis by Northern blot. However, the phenotypic analysis unexpectedly revealed the expression of CXCR3 on a large subset of circulating lymphocytes (FIG. 7B). This expression pattern was observed in all individuals examined, indicating that CXCR3 is normally expressed on a subset of blood lymphocytes. CXCR3 was found to mark a population of circulating T cells, which were contained within the CD45RO+ (memory) subset.

Murine hybridoma 1C6 (also referred to as LS77-1C6) was deposited on Mar. 28, 1997 at the American Type Culture Collection, 10801 University Blvd., Manassas, Va. 20110-2209, in accordance with the terms of the Budapest Treaty, under Accession Number HB-12330.

Example 5

CXCR3 is Expressed on Activated/memory T Cells

Flow Cytometry mAbs to CXCR1, CXCR2, CXCR3, and CCR5 have been described (Qin, S., et al., *Eur. J. Immunol.*, 26:640-647 (1996); Heath, H., et al., *J. Clin. Invest.*, in press (1997)). Anti-CXCR4 mAb 12G5 (Endres, M. J., et al., *Cell*, 87:745-756 (1996)) was kindly provided by Jim Hoxie (Univ. Penn.). PE-conjugated nAbs to CD4, CD8, CD14, CD20, CD25, CD26, CD69, CD45RO, CD45RA, CD95, and anti-CD3 and anti-CD4 Cy-Chrome were supplied by PharMingen (La Jolla, Calif.).

To assess reactivity of mAbs against transfected cells or leukocytes, indirect immunofluorescence and flow cytometry were used. Cells were washed once with PBS, and resuspended in 100 µl PBS containing 2% human serum and 0.1% sodium azide (staining buffer), 5 µg/ml purified antibody, 5 µg/ml IgG$_{2a}$ isotype matched control mAb (Sigma Chemical Co., St. Louis, Mo.) or 50 µl hybridoma culture supernatant. After 20 min at 4° C., cells were washed twice with staining buffer, and resuspended in 50 µl FITC-conjugated affinity purified F(ab')$_2$ goat anti-mouse IgG (Jackson ImmunoResearch Laboratories). After incubating for 20 min at 4° C., cells were washed twice in staining buffer and analyzed on the FACScan® to determine the level of surface expression. Propidium iodide was used to exclude dead cells.

Figure 8A:
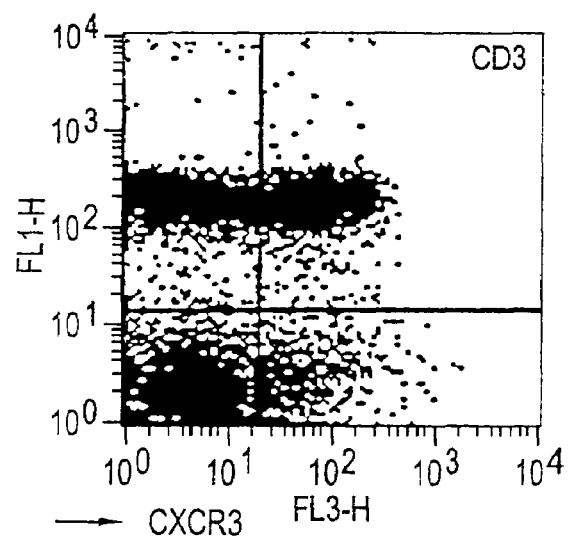
FIGS. 8A-8C are a series of plots illustrating CXCR3 expression on populations of blood lymphocytes. A two color staining protocol was used to assess expression of CXCR3 on T cells (CD3), B cells (CD20), and NK cells (CD56).
Figure 8B:
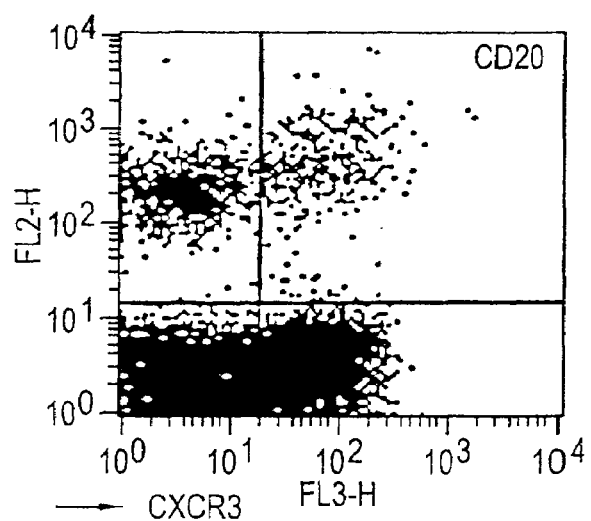
Figure 8C:
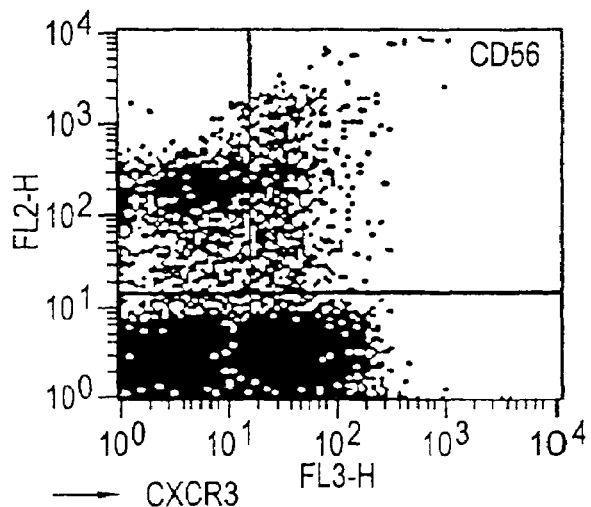
Figure 9A:
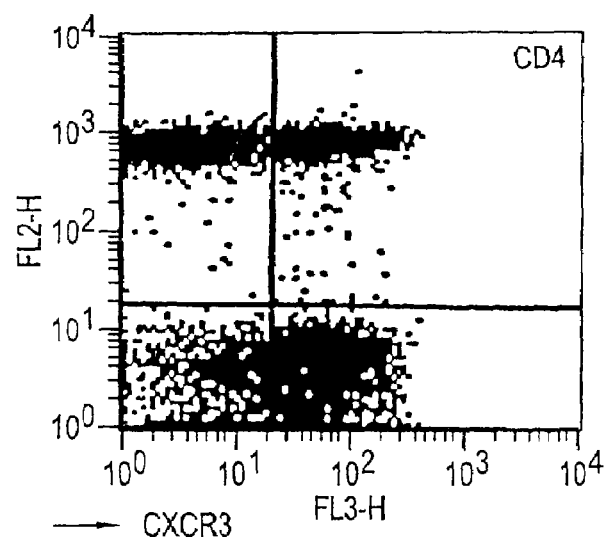
FIGS. 9A-9I are a series of plots illustrating CXCR3 expression versus various markers on the CD3+ subset of blood lymphocytes, as analyzed by three color analysis of immunofluorescence. Anti-CD3 Cy-Chrome was used to stain T cells, and these cells were gated electronically for analysis. Quadrants were set according to the staining of control mAbs. The staining shown was representative of five donors analyzed.
Figure 9B:
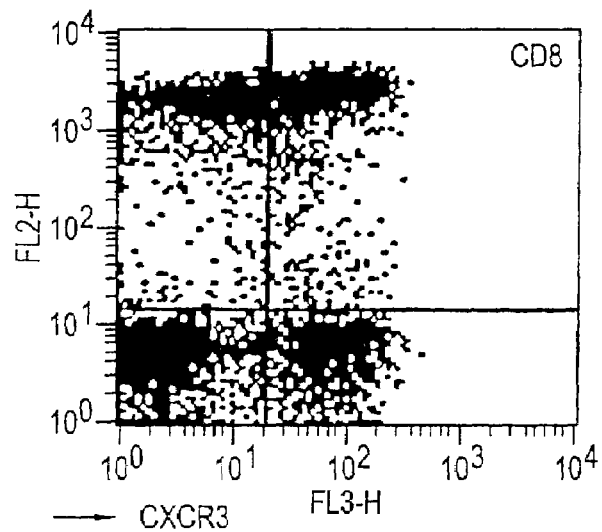
Figure 9C:
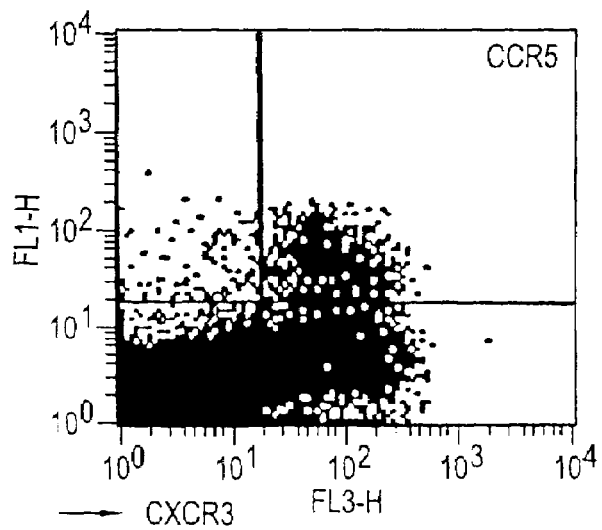
Figure 9D:
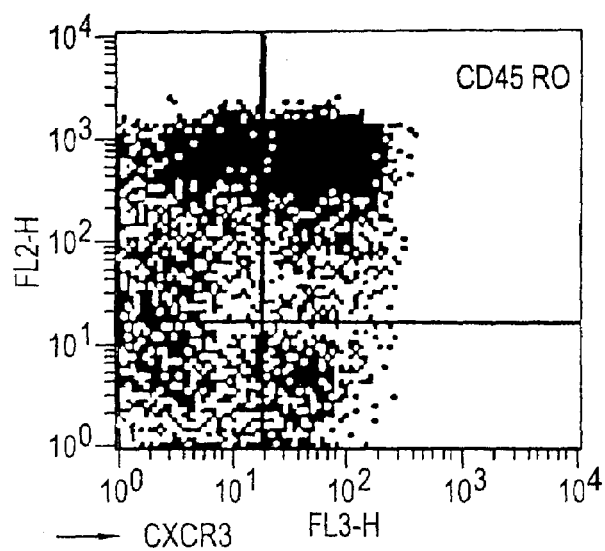
Figure 9E:
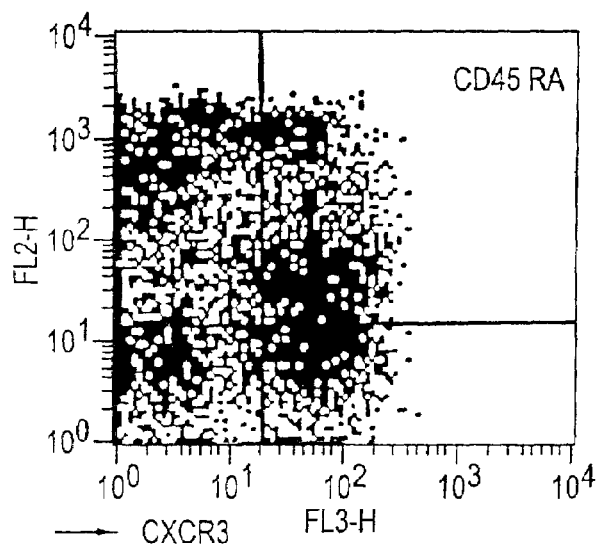
Figure 9F:
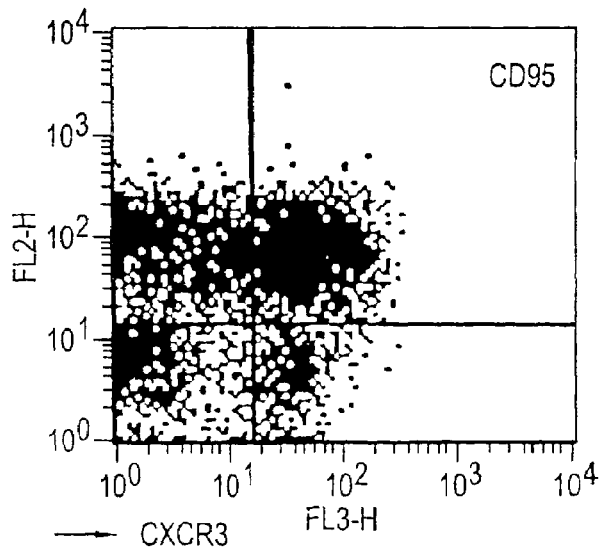
Figure 9G:
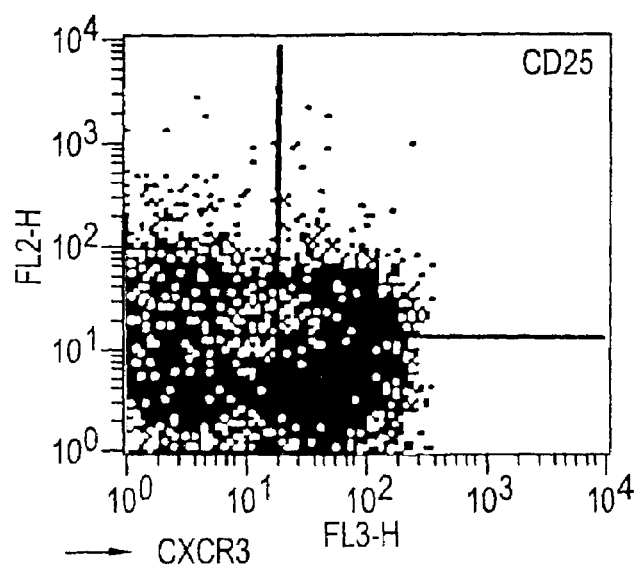
Figure 9H:
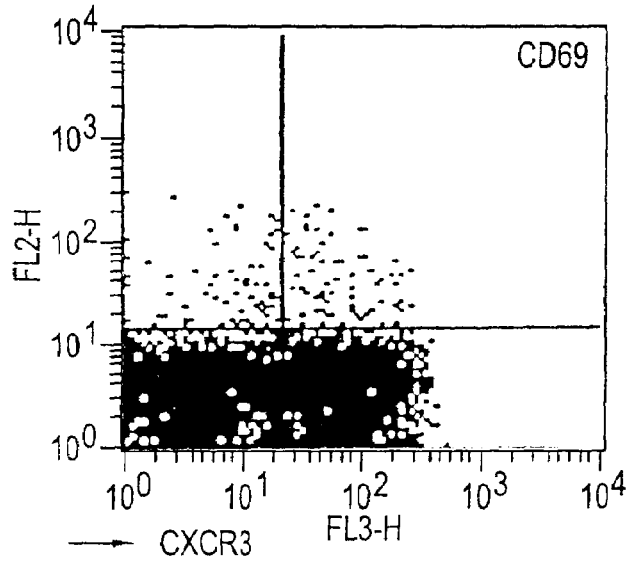
Figure 9I:
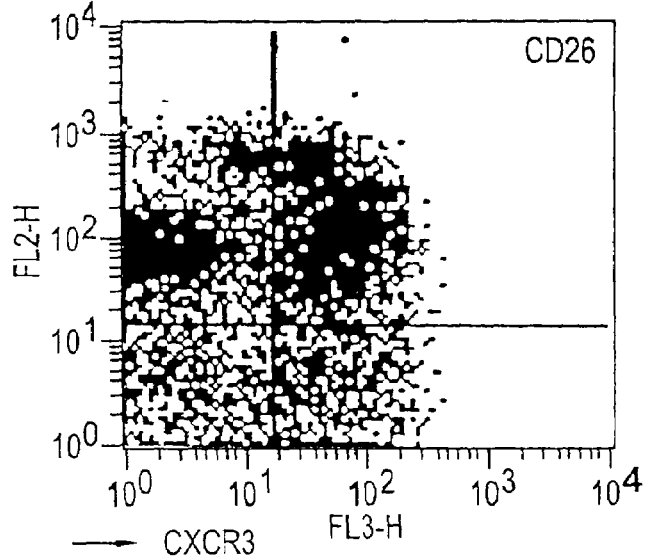

A two color immunofluorescence analysis of lymphocytes showed that it was mostly CD3+ cells that expressed CXCR3. Although a small proportion of CD20+ (B) cells and CD56+ (NK) cells also expressed this receptor (FIGS. 8A-8C) A three color analysis of T cells.

Example 6

Anti-CXCR3 mAb Blocks IP-10 Binding and Chemotaxis

Chemotaxis of human leukocytes was assessed using a modification of a transendothelial assay (Carr, M. W., et al., *Proc. Natl. Acad. Sci. USA*, 91(9):3652-3656 (1994)), which has been described previously (Ponath, P. D., et al., *J. Clin. Invest.*, 97:604-612 (1996)), using the ECV 304 endothelial cell line (European Collection of Animal Cell Cultures, Porton Down, Salisbury, U.K.). Cells that had migrated to the bottom chamber were placed in a tube, and relative cell counts were obtained using the FACSCAN (fluorescence activated flow cytometer)

Figure 10:
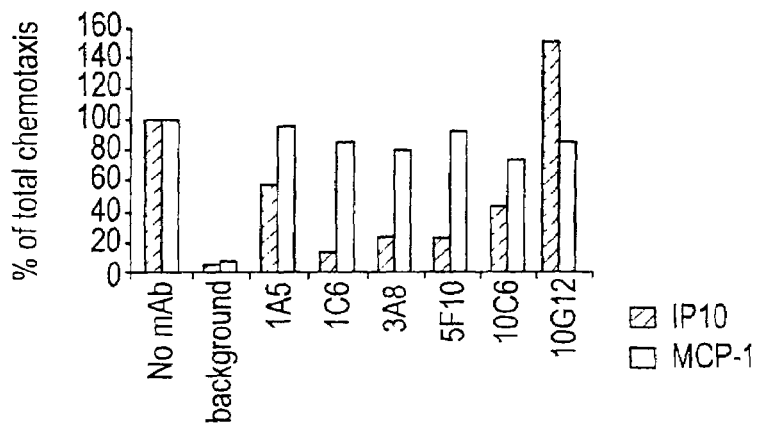
FIG. 10 is a histogram illustrating inhibition of IP-10- or MCP-1-mediated chemotaxis of activated T cells by a panel of anti-CXCR3 mAbs. 1×10$^6$ human CD3 blasts were placed in the top chamber of a transwell and chemokine (12.5 nM) was placed in the bottom chamber. Various anti-CXCR3 mAbs (in tissue culture supernatant, without FCS) were placed in the top well with cells at the beginning of the assay. After 1.5 hours the cells migrating to the bottom chamber were counted using flow cytometry. The percentage inhibition of chemotaxis was calculated using the number of cells that migrated in the absence of mAb as 100%. The results are representative of at least four separate experiments.
Figure 11:
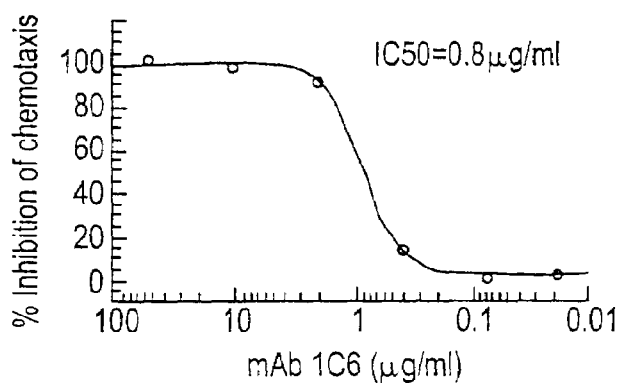
FIG. 11 is a graph illustrating the inhibition of IP-10 mediated chemotaxis by purified anti-CXCR3 mAb 1C6. Various concentrations of 1C6 mAb were placed in the top well, and the assay was performed as described for FIG. 10. mAb 1C6 inhibited 50% total chemotaxis at a concentration of 856 ng/ml (IC$_{50}$=856 ng/ml).
Figure 12:
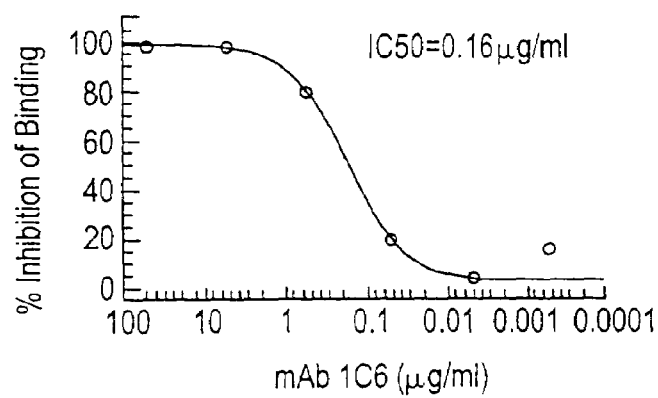
FIG. 12 is a graph illustrating the inhibition of $^{125}$I-IP-10 binding to activated T cells by mAb 1C6. CD3 blasts were incubated with 0.05 nM $^{125}$I-Ip-10 in the presence of increasing concentrations of 1C6 as indicated. After 60 minutes at room temperature, cell pellets were washed and counted. Data was analyzed by KaleidaGraph, which gave an IC$_{50}$ of 0.16 µg/ml.

The anti-peptide mAbs were also tested for their ability to inhibit the chemotaxis of CD3 activated T cell blasts. The results for mAbs designated 1A5, 1C6, 3AB, 5F10, 10C6 and 10G12 are illustrated in FIG. 10. One mAb, 1C6, was superior to the other mAbs in its ability to block the chemotaxis of T cells to IP-10. mAb 1C6 was able to inhibit completely the chemotaxis of T cells to IP-10 in a dose-dependent manner, with an IC$_{50}$ of ~0.8 µg/ml (FIG. 11). A concentration of 2-5 µg/ml was achieved 100% inhibition, using an optimal concentration of IP-10 (12.5 nM) in the bottom of the transwell. 1C6 was unable to significantly inhibit T cell chemotaxis to MCP-1 under the conditions used (FIG. 10), which occurs through the chemokine receptor CCR2b.

mAb 1C6 was also able to block completely $^{125}$I-labeled IP-10 binding to activated T cells, with an IC$_{50}$ of 0.16 µg/ml (FIG. 12). Between 1 and 10 µg/ml of antibody gave complete inhibition. The complete inhibition of both IP-10 binding and chemotaxis by mAb 1C6 indicates that activated T cells do not express another receptor that binds this chemokine.

Northern blot analysis indicated that CXCR3 was expressed in activated T cells. Using a panel of specific mAbs, CXCR3 was found to be expressed on a subset of blood T cells, as well as on other leukocyte types (B cells and NK cells). CXCR3 expressing T cells had a phenotype consistent with previous activation, i.e. CD45RO+, CD26+ (Example 5). Staining of T cells was markedly increased when T cells were activated by CD3 and IL-2, which correlated with increased cell migration in response to IP-10 and readiolabeled ligand binding.

The poor responsiveness of blood T cells to IP-10 or Mig, at least in chemotaxis assays, appears anomalous. A possible explanation is that factors other than receptor expression may determine cellular responsiveness to chemoattractants. Appropriate G protein coupling may be necessary for signalling. Another possibility is that the blood separation procedure disrupts this receptor, as has been observed for IL-8 receptors on T cells and NK cells (C. R. Mackay). Injection of IP-10 into the skin of in appropriate experimental animal can address the significance of CXCR3 expression on blood T cells. On activated T cells, IP-10 is one of the most potent chemoattractants. Activation of T cells may induce the receptor signalling molecules or coupling needed for signal transduction.

Example 7 mAb 1C6 Selectively Inhibits [Ca$^{2+}$]$_i$ by T cells in Response to IP-10, but Not Mig Intracellular calcium concentration ([Ca$^{2+}$]i) was determined as follows. A stock solution of Fura-2 AM (Molecular Probes, Eugene, Oreg.) was prepared by dissolving 50 μg of the dye in 44 μl of DMSO. Immediately prior to addition to cells, this stock was diluted 1:100 into HBSS with Ca$^{2+}$ and Mg$^{2+}$ and 2% BSA. Fura-2 AM was added to cells at a final concentration of 0.2 moles/10$^6$ cells at 37° C. for 30 minutes. Following labeling, excess dye was removed by centrifugation and cells were resuspended at a concentration of 10$^6$/ml in 125 mM NaCl, 5 mM KCl, 1 nM MgCl$_2$, 1 mM CaCl$_2$, 0.5 mM glucose, 0.025% BSA and 20 nM HEPES, pH 7.4. [Ca$_2$+]$_i$ was measured using excitation at 340 and 380 nm on a Hitachi F-2000 fluorescence spectrometer. Calibration was performed using 1% NP-40 for total release and 25 μM EGTA to chelate free Ca$^{2+}$.

Figure 13A:
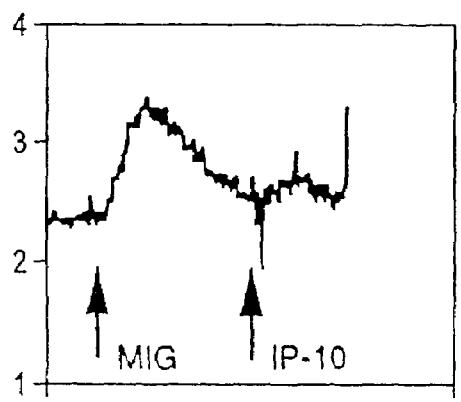
FIGS. 13A-13H illustrate the inhibition by mAb 1C6 of [Ca$^{2+}$]$_i$ by human T cells in response to IP-10, but not Mig. Anti-CD3 activated, IL-2-stimulated human T cells were labeled with Fura-2, and were stimulated sequentially with the indicated chemokines (FIGS. 13A-13B), or with mAb followed 40 seconds later by the indicated chemokine (FIGS. 13C-13H). [Ca$^{2+}$]$_i$ fluorescence changes were recorded using a spectrofluorimeter. The tracings were representative of five separate experiments. Antibody was used at a final concentration of either 50 µg/ml (FIGS. 13C-13D); 25 µg/ml (FIG. 13E); 12.5 µg/ml (FIG. 13F); 6.125 µg/ml (FIG. 13G); or 3.0625 µg/ml (FIG. 13H). Chemokines were used at 2 nM.
Figure 13B:
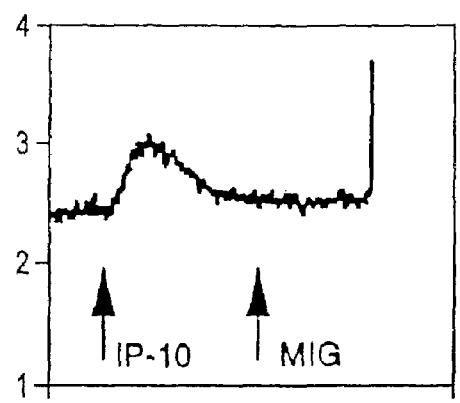
Figure 13C:
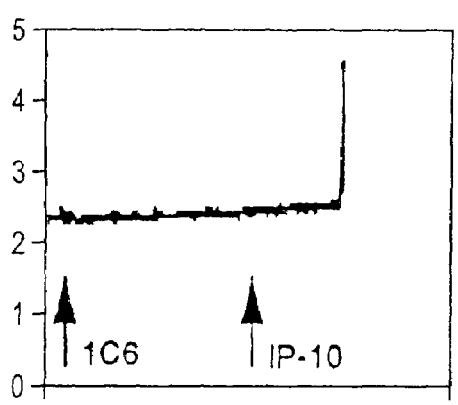
Figure 13D:
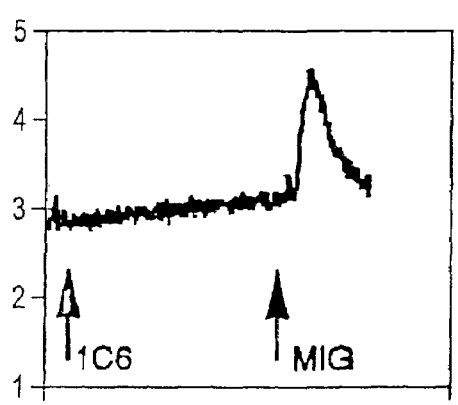
Figure 13E:
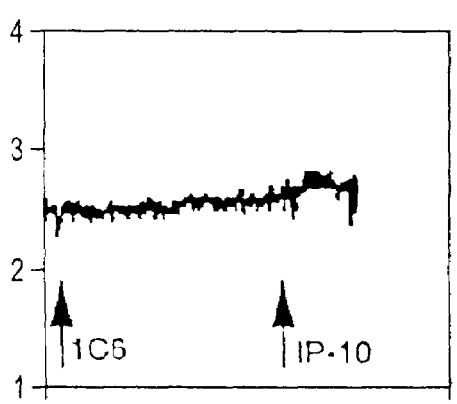
Figure 13F:
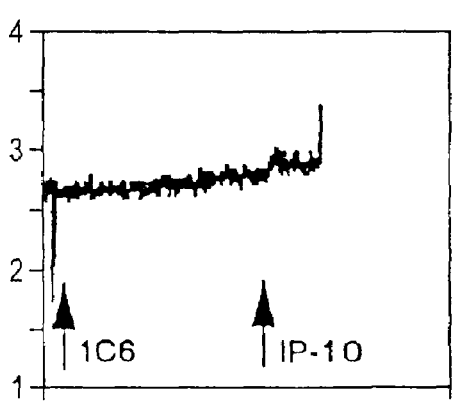
Figure 13G:
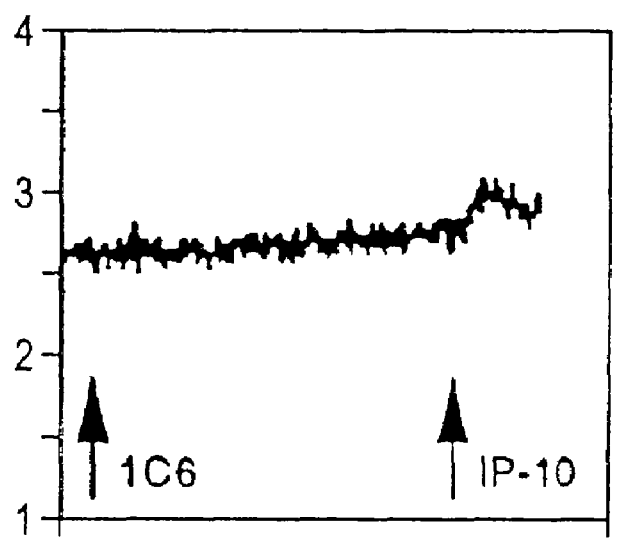
Figure 13H:
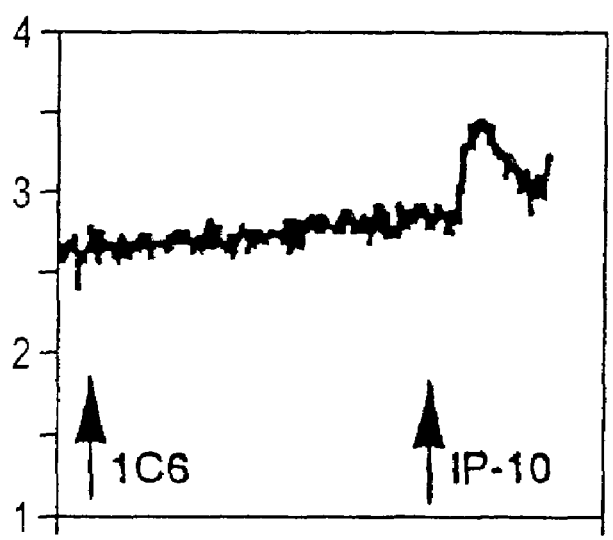
Figure 14A:
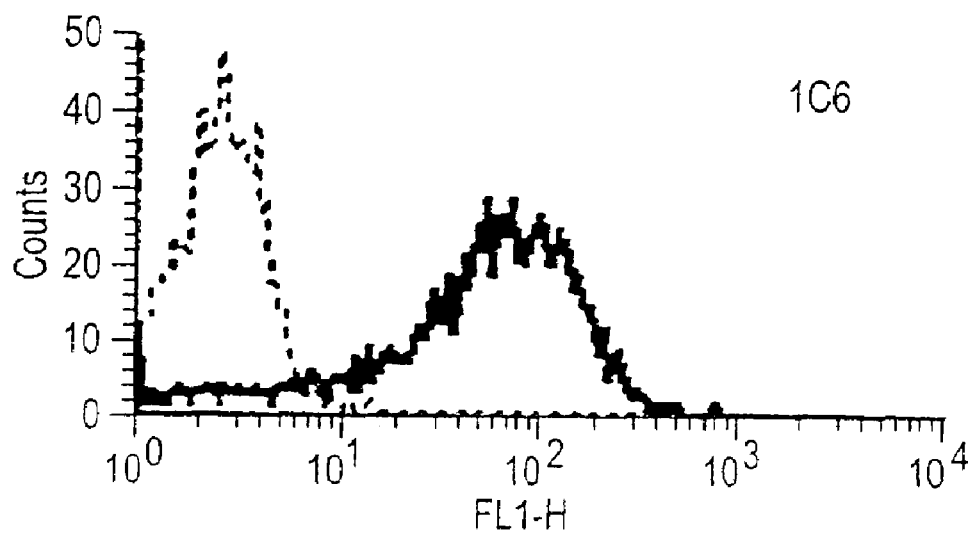
FIGS. 14A-14D are fluorescence histograms illustrating the results of a flow cytometry analysis in which CXCR3-expressing transfectants were stained with mAb 1C6 in the presence of P1 peptide (FIG. 14B), P2 peptide (FIG. 14C), P3 peptide (FIG. 14D), or in the absence of peptide (FIG. 14A). In each plot, the profile defined by the heavy line represents mAb 1C6 staining, and the profile defined by the dotted line represents staining with an isotype-matched irrelevant control mAb.
Figure 14B:
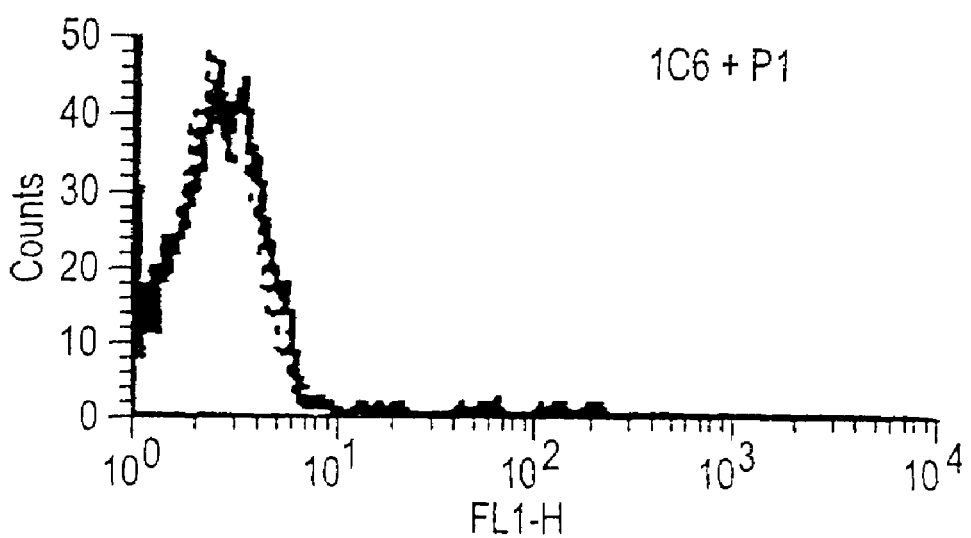
Figure 14C:
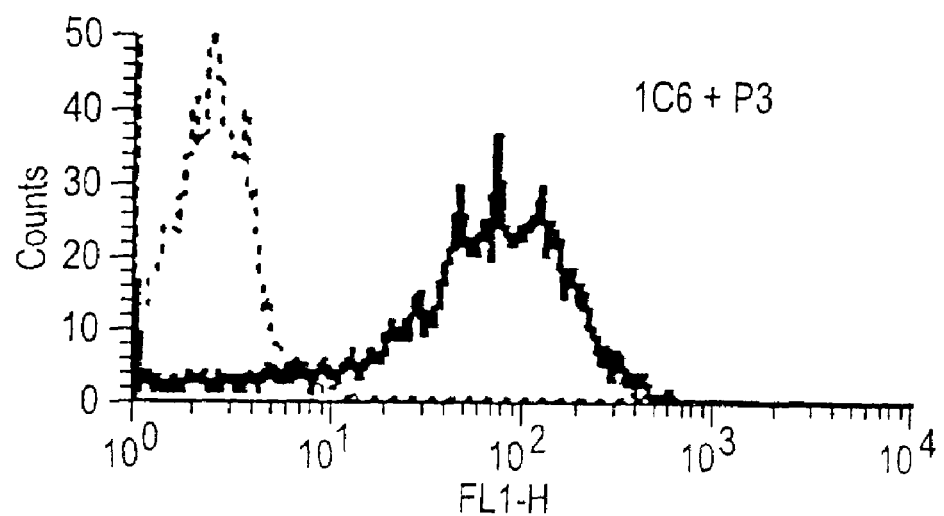
Figure 14D:
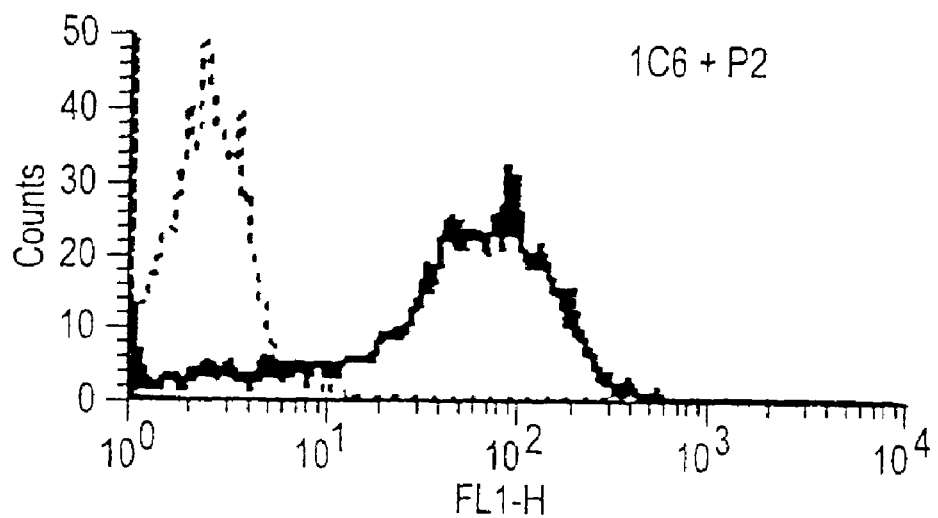

IP-10 and Mig induce [Ca$^{2+}$]$_i$ by human T cells, and each chemokine was able to completely desensitize responses to the other chemokine (FIGS. 13A-13B). A titration of the chemokines revealed that maximal [Ca$^{2+}$]$_i$ was achieved with as little as 2 nM IP-10 or 2 nM Mig. To examine the agonist/antagonist function of mAb 1C6, activated T cells were assessed for [Ca$^{2+}$]$_i$ following injection of mAb 1C6, or an irrelevant isotype-matched control mAb. T cells injected with an irrelevant isotype-matched control mAb showed a robust [Ca$_2$+]$_i$ response to subsequent injection of IP-10 (not shown). However, T cells treated with mAb 1C6 showed no [Ca$^{2+}$]$_i$ upon stimulation with 2 nM IP-10. [Ca$^{2+}$]$_i$ in activated T cells in response to IP-10 was completely suppressed by 12.5 mg of 1C6. However, as much as 50 μg/ml of 1C6 had no effect on the response of T cells to 2 nM Mig (FIG. 13D), indicating that the two ligands were differentially affected by this mAb. As a control, mAb 1C6 was tested for its effects on the [Ca$^{2+}$]$_i$ of T cells in response to MIP-1α or RANTES, which occurs through receptors other than CXCR3 (not shown). The mAb had no effect under the conditions used.

mAb 1C6, which inhibits IP-10 binding and IP-10-induced chemotaxis, also inhibited calcium flux by activated T cells, but did not inhibit Mig-induced calcium flux under these conditions. These results suggest the IP-10 and Mig bind and/or signal through different regions of CXCR3, and that mAb 1C6 G was able to block the IP-10 binding site and subsequent signalling. Thus, it is possible to develop receptor antagonists which selectively inhibit the effects of individual chemokines, illustrated here using mAb 1C6.

As discussed below, staining of CXCR3 transfectants can be inhibited by a peptide comprising the first 15 N-terminal amino acid residues of CXCR3. The inhibition of IP-10 binding and subsequent responses by mAb 1C6 suggests that this region is of particular functional importance for ligand binding. Based upon the inability of 1C6 to inhibit Mig-induced calcium flux under the conditions used, the epitope recognized by mAb 1C6, which appears to be important for IP-10 binding and signalling, does not appear to be involved in Mig binding and/or signalling.

Example 8

Epitope Mapping

Peptides were ordered from Genemed, South San Franciso, Calif. The peptides, each 15 amino acids long, correspond to different portions of the first 45 N-terminal residues of CXCR3 protein:

P1: MVLEVSDHQVLNDAE (SEQ ID NO:2, residues 1-15)

P2: VAALLENFSSSYDYG (SEQ ID NO:2, residues 16-30)

P3: ENESDSCCTSPPCPQ (SEQ ID NO:2, residues 31-45)

The peptides were first dissolved in DMSO and diluted to 1 mg/ml in phosphate buffered saline (PBS). To test tie ability of the peptides to block staining with 1C6 antibody, 1 μg/ml of purified 1C6 antibody was incubated in 1×PBS, 5% Fetal Calf Serum (FCS) with CXCR3 L1.2 transfectants (10$^5$ cells; see Materials and Methods for Examples 3-9) in the presence of 100 μg/ml of each peptide for 30 minutes at 4° C. Final volume was 100 μl. Positive staining was carried out in the absence of peptide. Bound mAb was detected with anti-mouse IgG-FITC and the results were analyzed by flow cytometry.

Staining with mAb 1C6 was completely inhibited by P1, suggesting that the mAb recognizes an epitope in the first N-terminal 15 amino acids of the CXCR3 protein (FIGS. 14A-14D). Binding of another mAb designated 3A8 (also referred to as LS77-3A8), which was produced from the same fusion (LS-77) as mAb 1C6, was also inhibited by the P1 peptide.

Example 9

Production of Anti-CXCR3 Monoclonal Antibodies by Immunization with Transfected Cells Additional anti-CXCR3 monoclonal antibodies were generated by immunization of mice with L1.2 cells transfected with a CXCR3 construct and expressing high levels of human CXCR3 (see Materials and Methods above). Immunization and generation of fusion hybridomas was performed as described (Qin, S. et al., *Eur. J. Immunol.*, 26: 640 (1996); and Heath, H. et al., *J. Clin. Invest.*, 99(2): 178 (1997)). Anti-CXCR3 mAbs were identified by positive staining of activated human T cells and CXCR3 transfectants. Eight anti-CXCR3 antibodies were obtained in one fusion (LS-104).

Figure 15:
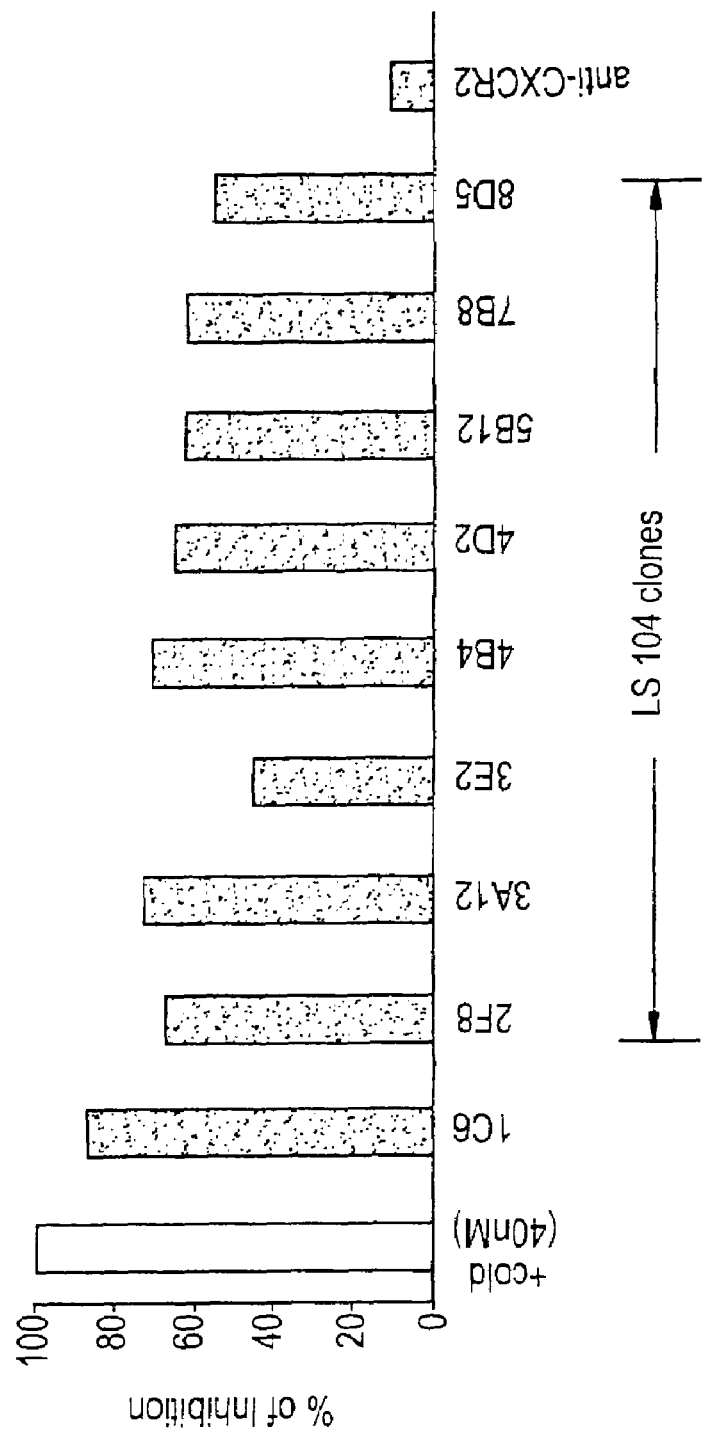
FIG. 15 is a histogram illustrating the percent inhibition of binding of radiolabeled IP-10 to CXCR3 transfectants by 40 nM cold IP-10, mAb 1C6, monoclonal antibodies raised against CXCR3 transfectants (2F8, 3A12, 3E2, 4B4, 4D2, 5B12, 7B8, or 8D5), or by anti-CXCR2 mAb.

The ability of these antibodies to inhibit binding of IP-10 to CXCR3 was tested. Tissue culture supernatants (25 μl) from the positive clones were incubated with CXCR3 L1.2 transfectant cells (Materials and Methods for Examples 3-9) and 0.05 nM of radiolabeled $^{125}$I-labeled IP-10 in 1×PBS, 5% Fetal Calf Serum (FCS) (100 μl final volume) for 30 minutes at 4° C. Supernatants of mAb 1C6 and an anti-CXCR2 (IL-8 receptor B) mAb were also used as specific and non-specific mAb controls, respectively. Total binding was determined in the absence of antibodies. Backgound binding was obtained using 40 nM unlabeled IP-10 as the competitor and this value was used to calculate the percentage of inhibition by the mAbs. The results are shown in FIG. 15. All antibodies from this fusion (LS-104) were able to block IP-10 binding, with the percentage inhibition ranging from 50-70%.

These mAbs were also assessed for their ability to inhibit signalling (ability to induce Ca$^{2+}$ flux) essentially as described in Example 7, but none of the antibodies was able to block Mig-mediated Ca$^{2+}$ signalling under the conditions used. Antibody inhibition of IP-10-mediated CXCR3 binding and signalling, but not Mig-mediated signalling via CXCR3, indicates that these antibodies can selectively inhibit CXCR3 functions mediated by IP-10.

Epitope mapping studies were also carried out using the antibodies from the LS-104 fusion essentially as described in Example 8. The results indicate that a variety of binding sites are recognized (Table 2). The results suggest that three of the antibodies recognize epitope(s) within the first 15 N-terminal amino acids of CXCR3 (residues 1-15 of SEQ ID NO:2), and two of the antibodies recognize epitope(s) within amino acids 16-30 of CXCR3 (residues 16-30 of SEQ ID NO:2). P3 peptide did not block staining with any of these antibodies, indicating that none of these antibodies bound the peptide representing amino acids 31-45 of CXCR3 (residues 31-45 of SEQ ID NO:2). Staining using the three remaining mAbs could not be significantly inhibited by any of the peptides under the conditions used, suggesting that these mAbs my bind epitopes comprising overlapping segments of the peptides, conformational epitopes displayed on the cell surface or epitopes on other parts of the receptor. These data also suggest that mAbs against various portions of CXCR3 can be obtained by immunizing mice with receptor transfectants.

TABLE 2

Epitope mapping of anti-CXCR3 mAbs

| Fusion Number mAb Name | Peptides which inhibit mAb staining of CXCR3 transfectants | Binding Region |
|---|---|---|
| LS-77[1] | | |
| 1C6 | P1 | AA 1-15 of SEQ ID NO:2 |
| 3A8 | P1 | AA 1-15 of SEQ ID NO:2 |
| LS-104[2] | | |
| 2F8 | none | |
| 3A12 | P1 | AA 1-15 of SEQ ID NO:2 |
| 3E2 | P1 | AA 1-15 of SEQ ID NO:2 |
| 4B4 | P2 | AA 16-30 of SEQ ID NO:2 |
| 4D2 | none | |
| 5B12 | none | |
| 7B8 | P2 | AA 16-30 of SEQ ID NO:2 |
| 8D5 | P1 | AA 1-15 of SEQ ID NO:2 |

[1]Antibodies obtained by peptide immunization
[2]Antibodies obtained by immunization with CXCR3 transfectants Example 10

Immunohistochemical Analysis of Normal and Inflamed Tissues Using mAb 1C6

Tissues

Human tissues (normal and inflamed) were obtained from the National Disease Research Institute, a service organization funded by the National Institutes of Health. Normal macaque (*Macaca mulatta*) tissues were obtained from the New England Regional Primate Research Center, Southboro, Mass.

Immunohistochemistry

Alkaline Phosphatase Technique. Tissue was sectioned at a thickness of 4 μm, desiccated, and then fixed in 2% paraformaldehyde/0.5×PBS for 10 minutes at 4° C. After PBS washing, nonspecific antibody binding sites were blocked with 10% normal goat serum/5% human AB serum/PBS for 30 minutes at room temperature. Next, the purified, anti-CXCR3 murine mAb 1C6, was diluted to a concentration of 10 μg/ml in 0.3% Triton X 100/0.2% Tween 20/1% FCS/5% human AB serum, and 0.1% sodium azide, and applied to tissue sections which were incubated overnight at 4° C. An isotype-matched irrelevant monoclonal antibody was used as a negative control on step sections of tissues (IgG$_1$, MOPC-21, SIGMA, St. Louis, Mo.). Subsequently, biotinylated goat anti-mouse IgG (Vector, Burlingame, Calif.) and avidin-biotin-alkaline phosphatase complexes (BIOGENEX, San Ramon, Calif.) were added in sequence. Fast Red (BIOGENEX, San Ramon, Calif.), containing levamisol to block endogenous alkaline phosphatase activity, was used as the chromogen and Mayers hematoxylin as the counterstain.

Results

Human and macaque normal lymph node: In both species, staining was limited to 70-80% of lymphocytes within the paracortex and medullary cords, consistent with CXCR3 expression on T lymphocytes.

Human and macaque spleen: In both species, staining was limited to lymphocytes along the periphery of lymphoid follicles of white pulp and scattered lymphocytes within splenic sinusoids. This pattern is consistent with CXCR3 expression on T lymphocytes.

Human thymus: The thymic medulla contained scattered CXCR3 immunoreactive mononuclear cells morphologically consistent with lymphocytes.

This analysis revealed that macaque CXCR3 is recognized by mAb 1C6. Separate studies showed that CXCR3 is upregulated by culturing macaque cells T lymphocytes with concanavalin A and IL-2, macaque T cell blasts can chemotax in response to human IP-10, mAb 1C6 can block this chemotaxis, and prior incubation with human IP-10 desensitizes macaque blasts as assessed by chemotaxis.

In the following discussion, variable numbers of CXCR3 immunoreactive "mononuclear cells" were identified in both normal and inflamed tissues. These mononuclear cells are most likely T lymphocytes for the following reasons: a) flow cytometry revealed that the majority of CXCR3$^+$ cells are T lymphocytes, although CXCR3 has been detected on some B cells and NK cells, but not on other mononuclear cells; b) within the lymph node and spleen, lymphocytes in regions known to be populated by T cells are the only cells that are immunoreactive for CXCR3; and c) the CXCR3 immunoreactive mononuclear cells in the tissues listed below are morphologically consistent with lymphocytes.

Non-inflamed human tissues: In non-inflamed human tissues including heart, liver, kidney, lung, skin, breast, skeletal muscle, salivary gland, pancreas, vagina, uterus, and ovary, CXCR3 expression was limited to rare, scattered interstitial mononuclear cells. In sections of small and large intestine, mononuclear cells expressing CXCR3 were observed within the lamina propria and Peyer's patches. In liver, periductal lymphocytes were also stained and hepatocytes were lightly stained.

Human brain: No staining was observed.

Inflamed human tissues: Several sections of chronically inflamed tissue characterized by interstitial and perivascular accumulation of mononuclear cells were examined for CXCR3 expression. In these tissues, including tissue from human patients with interstitial nephritis (1 case, kidney tissue), ulcerative colitis (1 case, colon tissue), enteritis (1 case, small intestine) and chronic vaginitis (4 cases, vagina), about 50%-90% of mononuclear cells were immunoreactive for CXCR3. Thus, compared to normal tissues, chronically inflamed tissues contained a greater number of interstitial mononuclear cells, and a greater percentage of these cells were immunoreactive for CXCR3.

Analysis of inflamed tissues revealed that about 50-90% of lymphocytes expressed CXCR3, whereas much lower percentages of lymphocytes in the corresponding normal tissue expressed CXCR3. These observations suggest specific recruitment of lymphocytes expressing CXCR3, most likely T lymphocytes expressing CXCR3, to sites of chronic inflammation. CXCR3 appears to mark T cells with a predilection for homing or migration to inflammatory sites.

EQUIVALENTS

Those skilled in the art will be able to recognize, or be able to ascertain, using no more than routine experimentation, many equivalents to the specific embodiments of the invention described herein. Such equivalents are intended to be encompassed by the following claims.

We claim:

1. A method of inhibiting recruitment of leukocytes to an inflammation site in an individual, comprising administering to said individual an effective amount of an antibody or antigen-binding fragment thereof which binds a human CXC Chemokine Receptor 3 (CXCR3) protein having the amino acid sequence of SEQ ID NO:2.

2. The method of claim 1 wherein said leukocytes are T cells.

3. The method of claim 1 wherein said antibody or antigen-binding fragment inhibits T cell activation.

4. The method of claim 1 wherein an antigen-binding fragment is administered, and said antigen-binding fragment is selected from the group consisting of a Fab fragment, a Fab' fragment, a F(ab')$_2$ fragment and a Fv fragment.

5. The method of claim 1 wherein said antibody or antigen-binding fragment is selected from the group consisting of a human antibody or antigen-binding fragment thereof, a humanized antibody or antigen-binding fragment thereof, and a chimeric antibody or antigen-binding fragment thereof.

6. A method of inhibiting recruitment of leukocytes to an inflammation site in an individual, comprising administering to said individual an effective amount of an antibody or antigen-binding fragment thereof which binds a human CXC Chemokine Receptor 3 (CXCR3) protein having the amino acid sequence of SEQ ID NO:2, wherein said antibody or antigen-binding fragment inhibits one or more functions of said human CXCR3 protein selected from the group consisting of binding of a ligand, ligand-induced calcium flux and ligand-induced chemotaxis.

7. The method of claim 6 wherein said leukocytes are T cells.

8. The method of claim 6 wherein said antibody or antigen-binding fragment inhibits T cell activation.

9. The method of claim 6 wherein binding of said antibody or antigen-binding fragment to human CXCR3 is inhibited by a portion of a human CXCR3 corresponding to the N-terminal extracellular segment of SEQ ID NO:2.

10. The method of claim 6 wherein binding of said antibody or antigen-binding fragment to human CXCR3 protein is inhibited by a polypeptide having a sequence which is the same as that of residues 1-15 of SEQ ID NO:2.

11. The method of claim 6 wherein binding of said antibody or antigen-binding fragment to human CXCR3 protein is inhibited by a polypeptide having a sequence which is the same as that of residues 16-30 of SEQ ID NO:2.

12. The method of claim 10 wherein binding of said antibody or antigen-binding fragment to human CXCR3 protein is not inhibited by a polypeptide having a sequence which is the same as that of residues 16-30 of SEQ ID NO:2 or by a polypeptide having a sequence which is the same as that of residues 31-45 of SEQ ID NO:2.

13. The method of claim 6 wherein said antibody or antigen-binding fragment inhibits binding of a ligand to said human CXCR3 protein.

14. The method of claim 13 wherein said ligand is selected from the group consisting of IP-10 and Mig.

15. The method of claim 14 wherein said ligand is human IP-10.

16. The method of claim 14 wherein said ligand is human Mig.

17. The method of claim 13 wherein said antibody or antigen-binding fragment selectively inhibits the binding of IP-10 to said CXCR3 protein.

18. The method of claim 6 wherein said antibody or antigen-binding fragment inhibits a signalling activity or a cellular response function mediated by binding of IP-10 to said CXCR3 protein.

19. The method of claim 6 wherein said antibody or antigen-binding fragment competes with monoclonal antibody 1C6 (ATCC Accession Number HB-12330) for binding to a human CXCR3 protein.

20. The method of claim 6 wherein said antibody or antigen-binding fragment has the epitopic specificity of monoclonal antibody 1C6 (ATCC Accession Number HB-12330).

21. The method of claim 6 wherein an antigen-binding fragment is administered, and said antigen-binding fragment is selected from the group consisting of a Fab fragment, a Fab' fragment, a F(ab')$_2$ fragment and a Fv fragment.

22. The method of claim 6 wherein said antibody or antigen-binding fragment is selected from the group consisting of a human antibody or antigen-binding fragment thereof, a humanized antibody or antigen-binding fragment thereof, and a chimeric antibody or antigen-binding fragment thereof.

23. A method of inhibiting recruitment of leukocytes to an inflammation site in an individual, comprising administering to said individual an effective amount of a humanized antibody or antigen-binding fragment thereof comprising the light chain CDRs (CDR1, CDR2 and CDR3) and the heavy chain CDRs (CDR1, CDR2 and CDR3) of monoclonal antibody 1C6 (ATCC Accession Number HB-12330) and a human framework region, wherein said humanized antibody or antigen-binding fragment thereof has the epitopic specificity of monoclonal antibody 1C6 (ATCC Accession Number HB-12330).

24. The method of claim 23 wherein said leukocytes are T cells.

25. A method of treating an inflammatory disease or condition, comprising administering to an individual in need thereof an effective amount of an antibody or antigen-binding fragment thereof which binds a human CXC Chemokine Receptor 3 (CXCR3) protein having the amino acid sequence of SEQ ID NO:2.

26. The method of claim 25 wherein said antibody or antigen-binding fragment inhibits T cell activation.

27. The method of claim 25 wherein said inflammatory disease or condition is an acute inflammatory disease or condition.

28. The method of claim 25 wherein said inflammatory disease or condition is a chronic inflammatory disease or condition.

29. The method of claim 25 wherein said inflammatory disease or condition is selected from the group consisting of psoriasis, inflammatory bowel disease, nephritis, multiple sclerosis and graft rejection.

30. The method of claim 25 wherein an antigen-binding fragment is administered, and said antigen-binding fragment is selected from the group consisting of a Fab fragment, a Fab' fragment, a F(ab')$_2$ fragment and a Fv fragment.

31. The method of claim 25 wherein said antibody or antigen-binding fragment is selected from the group consisting of a human antibody or antigen-binding fragment thereof, a humanized antibody or antigen-binding fragment thereof, and a chimeric antibody or antigen-binding fragment thereof.

32. A method of treating an inflammatory disease or condition, comprising administering to an individual in need thereof an effective amount of an antibody or antigen-binding fragment thereof which binds a human CXC Chemokine Receptor 3 (CXCR3) protein having the amino acid sequence of SEQ ID NO:2, wherein said antibody or antigen-binding fragment inhibits one or more functions of said human CXCR3 protein selected from the group consisting of binding of a ligand, ligand-induced calcium flux and ligand-induced chemotaxis.

33. The method of claim 32 wherein said antibody or antigen-binding fragment inhibits T cell activation.

34. The method of claim 32 wherein binding of said antibody or antigen-binding fragment to human CXCR3 is inhibited by a portion of a human CXCR3 protein corresponding to the N-terminal extracellular segment of SEQ ID NO:2.

35. The method of claim 32 wherein binding of said antibody or antigen-binding fragment to human CXCR3 protein is inhibited by a polypeptide having a sequence which is the same as that of residues 1-15 of SEQ ID NO:2.

36. The method of claim 32 wherein binding of said antibody or antigen-binding fragment to human CXCR3 protein is inhibited by a polypeptide having a sequence which is the same as that of residues 16-30 of SEQ ID NO:2.

37. The method of claim 35 wherein binding of said antibody or antigen-binding fragment to human CXCR3 protein is not inhibited by a polypeptide having a sequence which is the same as that of residues 16-30 of SEQ ID NO:2 or by a polypeptide having a sequence which is the same as that of residues 31-45 of SEQ ID NO:2.

38. The method of claim 32 wherein said antibody or antigen-binding fragment inhibits binding of a ligand to said human CXCR3 protein.

39. The method of claim 38 wherein said ligand is selected from the group consisting of IP-10 and Mig.

40. The method of claim 39 wherein said ligand is human IP-10.

41. The method of claim 39 wherein said ligand is human Mig.

42. The method of claim 38 wherein said antibody or antigen-binding fragment selectively inhibits the binding of IP-10 to said human CXCR3 protein.

43. The method of claim 32 wherein said antibody or antigen-binding fragment inhibits calcium flux or chemotaxis induced by binding of IP-10 to said human CXCR3 protein.

44. The method of claim 32 wherein said antibody or antigen-binding fragment competes with monoclonal antibody 1C6 (ATCC Accession Number HB-12330) for binding to a human CXCR3 protein.

45. The method of claim 32 wherein said antibody or antigen-binding fragment has the epitopic specificity of monoclonal antibody 1C6 (ATCC Accession Number HB-12330).

46. The method of claim 32 wherein an antigen-binding fragment is administered, and said antigen-binding fragment is selected from the group consisting of a Fab fragment, a Fab' fragment, a F(ab')$_2$ fragment and a Fv fragment.

47. The method of claim 32 wherein said antibody or antigen-binding fragment is selected from the group consisting of a human antibody or antigen-binding fragment thereof, a humanized antibody or antigen-binding fragment thereof, and a chimeric antibody or antigen-binding fragment thereof.

48. The method of claim 32 wherein said inflammatory disease or condition is an acute inflammatory disease or condition.

49. The method of claim 32 wherein said inflammatory disease or condition is a chronic inflammatory disease or condition.

50. The method of claim 32 wherein said inflammatory disease or condition is selected from the group consisting of psoriasis, inflammatory bowel disease, nephritis, multiple sclerosis and graft rejection.

51. A method of treating an inflammatory disease or condition, comprising administering to an individual in need thereof an effective amount of an antibody or antigen-binding fragment thereof that binds a human CXC Chemokine Receptor 3 (CXCR3) protein having the amino acid sequence of SEQ ID NO:2, wherein said antibody or antigen-binding fragment inhibits binding of human IP-10 to said CXCR3 protein and inhibits one or more functions mediated by said CXCR3 protein in response to IP-10 binding selected from the group consisting of calcium flux and chemotaxis.

52. The method of claim 51 wherein said antibody or antigen-binding fragment inhibits T cell activation.

53. The method of claim 51 wherein said inflammatory disease or condition is an acute inflammatory disease or condition.

54. The method of claim 51 wherein said inflammatory disease or condition is a chronic inflammatory disease or condition.

55. The method of claim 51 wherein said inflammatory disease or condition is selected from the group consisting of psoriasis, inflammatory bowel disease, nephritis, multiple sclerosis and graft rejection.

56. A method of treating an inflammatory disease or condition, comprising administering to an individual in need thereof an effective amount of an antibody or antigen-binding fragment thereof which binds a human CXC Chemokine Receptor 3 (CXCR3) protein having the amino acid sequence of SEQ ID NO:2, wherein said antibody or antigen-binding fragment inhibits one or more functions of said human CXCR3 protein selected from the group consisting of binding of a ligand, ligand-induced calcium flux and ligand-induced chemotaxis, and wherein the binding of said antibody or antigen-binding fragment to said human CXCR3 is inhibited by a polypeptide having a sequence which is the same as that of residues 1-15 of SEQ ID NO:2.

57. The method of claim 56 wherein said antibody or antigen-binding fragment inhibits T cell activation.

58. The method of claim 56 wherein said antibody or antigen-binding fragment inhibits binding of human IP-10 to said human CXCR3 protein.

59. The method of claim 56 wherein said antibody or antigen-binding fragment inhibits binding of human Mig to said human CXCR3 protein.

60. The method of claim 56 wherein an antigen-binding fragment is administered, and said antigen-binding fragment is selected from the group consisting of a Fab fragment, a Fab' fragment, a F(ab')$_2$ fragment and a Fv fragment.

61. The method of claim 56 wherein said antibody or antigen-binding fragment is selected from the group consisting of a human antibody or antigen-binding fragment thereof, a humanized antibody or antigen-binding fragment thereof, and a chimeric antibody or antigen-binding fragment thereof.

62. The method of claim 56 wherein said inflammatory disease or condition is an acute inflammatory disease or condition.

63. The method of claim 56 wherein said inflammatory disease or condition is a chronic inflammatory disease or condition.

64. The method of claim 56 wherein said inflammatory disease or condition is selected from the group consisting of psoriasis, inflammatory bowel disease, nephritis, multiple sclerosis and graft rejection.

65. A method of treating an inflammatory disease or condition, comprising administering to an individual in need thereof an effective amount of an antibody or antigen-binding fragment thereof which binds a human CXC Chemokine Receptor 3 (CXCR3) protein having the amino acid sequence of SEQ ID NO:2, wherein said antibody or antigen-binding fragment inhibits one or more functions of said human CXCR3 protein selected from the group consisting of binding of a ligand, ligand-induced calcium flux and ligand-induced chemotaxis, and wherein the binding of said antibody or antigen-binding fragment to said human CXCR3 is inhibited by a polypeptide having a sequence which is the same as that of residues 16-30 of SEQ ID NO:2.

66. The method of claim 65 wherein said antibody or antigen-binding fragment inhibits T cell activation.

67. The method of claim 65 wherein said antibody or antigen-binding fragment inhibits binding of human IP-10 to the human CXCR3 protein.

68. The method of claim 65 wherein said antibody or antigen-binding fragment inhibits binding of human Mig to the human CXCR3 protein.

69. The method of claim 65 wherein an antigen-binding fragment is administered, and said antigen-binding fragment is selected from the group consisting of a Fab fragment, a Fab' fragment, a F(ab')$_2$ fragment and a Fv fragment.

70. The method of claim 65 wherein said antibody or antigen-binding fragment is selected from the group consisting of a human antibody or antigen-binding fragment thereof, a humanized antibody or antigen-binding fragment thereof, and a chimeric antibody or antigen-binding fragment thereof.

71. The method of claim 65 wherein said inflammatory disease or condition is an acute inflammatory disease or condition.

72. The method of claim 65 wherein said inflammatory disease or condition is a chronic inflammatory disease or condition.

73. The method of claim 65 wherein said inflammatory disease or condition is selected from the group consisting of psoriasis, inflammatory bowel disease, nephritis, multiple sclerosis and graft rejection.

74. A method of treating an inflammatory disease or condition, comprising administering to an individual in need thereof an effective amount of a humanized antibody or antigen-binding fragment thereof comprising the light chain CDRs (CDR1, CDR2 and CDR3) and the heavy chain CDRs (CDR1, CDR2 and CDR3) of monoclonal antibody 1C6 (ATCC Accession Number HB-12330) and a human framework region, wherein said humanized antibody or antigen-binding fragment thereof has the epitopic specificity of monoclonal antibody 1C6 (ATCC Accession Number HB-12330).

75. The method of claim 74 wherein said inflammatory disease or condition is an acute inflammatory disease or condition.

76. The method of claim 74 wherein said inflammatory disease or condition is a chronic inflammatory disease or condition.

77. The method of claim 74 wherein said inflammatory disease or condition is selected from the group consisting of psoriasis, inflammatory bowel disease, nephritis, multiple sclerosis and graft rejection.

* * * * *